US008288341B2

(12) United States Patent
Benner et al.

(10) Patent No.: US 8,288,341 B2
(45) Date of Patent: Oct. 16, 2012

(54) CONTROL OF RADIATION INJURY

(75) Inventors: Robbert Benner, Barendrecht (NL); Nisar Ahmed Khan, Rotterdam (NL); Richard Michael Carlton, Washington, NY (US)

(73) Assignee: Biotempt B.V., Koekange (NL)

( * ) Notice: Subject to any disclaimer, the term of this patent is extended or adjusted under 35 U.S.C. 154(b) by 471 days.

(21) Appl. No.: 12/460,317

(22) Filed: Jul. 15, 2009

(65) Prior Publication Data

US 2009/0291901 A1 Nov. 26, 2009

Related U.S. Application Data

(62) Division of application No. 11/715,314, filed on Mar. 7, 2007, now Pat. No. 7,795,226.

(60) Provisional application No. 60/811,878, filed on Jun. 7, 2006, provisional application No. 60/779,896, filed on Mar. 7, 2006.

(30) Foreign Application Priority Data

Jun. 7, 2006 (EP) .................................... 06076181

(51) Int. Cl.
*A61K 38/06* (2006.01)
*A61K 38/07* (2006.01)
*A61K 38/08* (2006.01)

(52) U.S. Cl. ...... 514/9.7; 514/13.2; 514/21.6; 514/21.7; 514/21.8; 514/21.9

(58) Field of Classification Search ........................ None
See application file for complete search history.

(56) References Cited

U.S. PATENT DOCUMENTS 3,855,397 A 12/1974 Hoffman et al.
3,898,328 A 8/1975 Beigler et al.
3,960,830 A 6/1976 Bayer et al.
4,003,989 A 1/1977 Bar-On
4,083,951 A 4/1978 Goudie et al.
4,108,846 A 8/1978 Meienhofer
4,140,760 A 2/1979 Withington
4,265,874 A 5/1981 Bonsen et al.
4,289,750 A 9/1981 Kopp et al.
4,330,466 A 5/1982 Yanaihara et al.
4,351,762 A 9/1982 Verlander et al.
4,427,660 A 1/1984 Schiffman et al.
4,571,336 A 2/1986 Houck et al.
4,753,965 A 6/1988 Stemerick et al.
4,855,285 A 8/1989 Stevens
4,966,848 A 10/1990 Smith et al.
4,977,244 A 12/1990 Muchmore et al.
5,002,961 A 3/1991 Dage et al.
5,010,175 A 4/1991 Rutter et al.
5,055,447 A 10/1991 Palladino et al.
5,070,187 A 12/1991 Gavras et al.
5,102,393 A 4/1992 Sarnoff et al.
5,175,254 A 12/1992 Calas et al.
5,200,507 A 4/1993 Chieng
5,223,397 A 6/1993 Pouletty
5,223,421 A 6/1993 Smith et al.
5,308,834 A 5/1994 Scott et al.
5,380,668 A 1/1995 Herron
5,436,270 A 7/1995 Wang
5,554,378 A 9/1996 Uda et al.
5,610,272 A 3/1997 Wang
5,616,608 A 4/1997 Kinsella et al.
5,677,275 A 10/1997 Lunardi-Iskandar et al.
5,700,781 A 12/1997 Harris
5,801,193 A 9/1998 Ojo-Amaize et al.
5,807,746 A 9/1998 Lin et al.
5,837,218 A 11/1998 Peers et al.
5,837,478 A 11/1998 Gallatin et al.
5,851,997 A 12/1998 Harris
5,854,004 A 12/1998 Czernilofsky et al.
5,856,440 A 1/1999 Wang
5,858,375 A 1/1999 Furminger et al.
5,877,148 A 3/1999 Lunardi-Iskandar et al.
5,942,494 A 8/1999 Ginsberg et al.
5,958,413 A 9/1999 Anagnostopulos et al.
5,966,712 A 10/1999 Sabatini et al.
5,968,513 A 10/1999 Gallo et al.
5,972,924 A 10/1999 Keep et al.

(Continued)

FOREIGN PATENT DOCUMENTS

EP 0 572 688 5/1997
EP 1 138 692 A1 10/2001
EP 1 300 418 4/2003
EP 1 224 212 B1 7/2003
EP 1 466 612 A1 10/2004
GB 2 194 886 A 3/1988
JP 09-176187 A 7/1997
JP 2003516931 5/2003
WO WO 80/02459 11/1980
WO WO 92/20795 A1 11/1992

(Continued)

OTHER PUBLICATIONS

Cohen, Int J. Radiat. Oncol. Biol. Phys., 1987, pp. 251-258, vol. 13.
Hierholzer et al., Essential role of induced nitric oxide in the initiation of the inflammatory response after hemorrhagic shock, J. Exp. Med., Mar. 1998, pp. 917-928, vol. 187, No. 6.
Office Action for U.S. Appl. No. 10/409,032 dated May 17, 2007.

(Continued)

*Primary Examiner* — Jeffrey E Russel
(74) *Attorney, Agent, or Firm* — TraskBritt

(57) ABSTRACT

Methods of treating radiation injury of a subject in need thereof comprising administering to the subject a peptide consisting of an amino acid molecule selected from the group consisting of VVC, LAG, AQG, LQGV, QVVC, MTRV, LAGV, LQAV, PGCP, VGQL, RVLQ, EMFQ, AVAL, FVLS, NMWD, LCFL, FSYA, FWVD, AFTV, LGTL, QLLG, YAIT, APSL, ITTL, QALG, GVLC, NLIN, SPIE, LNTI, LHNL, CPVQ, EVVR, MTEV, EALE, EPPE, LGTL, VGGI, RLPG, LQGA, LCFL, TLAVE, VEGNL, LNEAL, CPRGVNP, MGGTWA, LTCDDP, VCNYRDV, QPLAPLVG, and DINGFLPAL. The invention provides for administration of the peptide prior to and following exposure of the subject to a source of radiation.

9 Claims, 4 Drawing Sheets

U.S. PATENT DOCUMENTS

| | | | |
|---|---|---|---|
| 5,981,486 | A | 11/1999 | Matsushima et al. |
| 5,994,126 | A | 11/1999 | Steinman et al. |
| 5,997,871 | A | 12/1999 | Gallo et al. |
| 6,022,696 | A | 2/2000 | Harding et al. |
| 6,051,596 | A | 4/2000 | Badger |
| 6,075,150 | A | 6/2000 | Wang et al. |
| 6,086,918 | A | 7/2000 | Stern et al. |
| 6,150,500 | A | 11/2000 | Salerno |
| 6,207,145 | B1 | 3/2001 | Tovey |
| 6,211,151 | B1 | 4/2001 | Sikiric et al. |
| 6,235,281 | B1 | 5/2001 | Stenzel et al. |
| 6,271,199 | B2 | 8/2001 | Brand et al. |
| 6,278,794 | B1 | 8/2001 | Parekh et al. |
| 6,309,822 | B1 | 10/2001 | Fodor et al. |
| 6,310,041 | B1 | 10/2001 | Haddox et al. |
| 6,319,504 | B1 | 11/2001 | Gallo et al. |
| 6,329,573 | B1 | 12/2001 | Lightfoot et al. |
| 6,361,992 | B1 | 3/2002 | Szkudlinski et al. |
| 6,379,970 | B1 | 4/2002 | Liebler et al. |
| 6,416,959 | B1 | 7/2002 | Giuliano et al. |
| 6,489,296 | B1 | 12/2002 | Grinnell et al. |
| 6,507,788 | B1 | 1/2003 | Camara y Ferrer et al. |
| 6,518,021 | B1 | 2/2003 | Thastrup et al. |
| 6,539,102 | B1 | 3/2003 | Anderson et al. |
| 6,583,109 | B1 | 6/2003 | Gallo et al. |
| 6,586,403 | B1 | 7/2003 | Mathison et al. |
| 6,596,688 | B1 | 7/2003 | Gallo et al. |
| 6,620,416 | B1 | 9/2003 | Gallo et al. |
| 6,630,138 | B2 | 10/2003 | Gerlitz et al. |
| 6,642,201 | B1 | 11/2003 | Khavinson et al. |
| 6,645,934 | B1 | 11/2003 | Rodemann et al. |
| 6,652,860 | B1 | 11/2003 | Singh et al. |
| 6,699,656 | B2 | 3/2004 | Gallo et al. |
| 6,711,563 | B1 | 3/2004 | Koskas |
| 6,727,227 | B1 | 4/2004 | Khavinson |
| 6,783,757 | B2 | 8/2004 | Brudnak |
| 6,831,057 | B2 | 12/2004 | Baldwin et al. |
| 6,844,315 | B2 | 1/2005 | Khan et al. |
| 6,852,697 | B1 | 2/2005 | Mathison et al. |
| 6,894,028 | B2 | 5/2005 | Lipton et al. |
| 6,921,751 | B1 | 7/2005 | Khan et al. |
| 7,094,760 | B2 | 8/2006 | Mathison et al. |
| 7,135,286 | B2 | 11/2006 | Margus et al. |
| 7,175,679 | B2 | 2/2007 | Khan et al. |
| 7,316,819 | B2 | 1/2008 | Grotts et al. |
| 7,358,330 | B2 | 4/2008 | Khan et al. |
| 7,365,155 | B2 | 4/2008 | Khan et al. |
| 7,368,535 | B2 | 5/2008 | Gorczynski et al. |
| 7,402,322 | B2 | 7/2008 | Khan et al. |
| 7,501,391 | B2 | 3/2009 | Khan et al. |
| 7,517,529 | B2 | 4/2009 | Khan et al. |
| 7,524,820 | B1 | 4/2009 | Khan et al. |
| 7,560,433 | B2 | 7/2009 | Khan et al. |
| 7,576,174 | B2 | 8/2009 | Benner et al. |
| 7,662,776 | B2 | 2/2010 | Khan et al. |
| 7,786,084 | B2 | 8/2010 | Benner et al. |
| 7,795,226 | B2 | 9/2010 | Benner et al. |
| 2002/0041871 | A1 | 4/2002 | Brudnak |
| 2002/0064501 | A1 | 5/2002 | Khan et al. |
| 2002/0147306 | A1 | 10/2002 | Lin et al. |
| 2002/0155106 | A1 | 10/2002 | Hammond |
| 2003/0003545 | A1 | 1/2003 | Ebner et al. |
| 2003/0049273 | A1 | 3/2003 | Gallo et al. |
| 2003/0060505 | A1* | 3/2003 | Reddy et al. ............... 514/461 |
| 2003/0113733 | A1 | 6/2003 | Khan et al. |
| 2003/0119720 | A1 | 6/2003 | Khan et al. |
| 2003/0148955 | A1 | 8/2003 | Pluenneke |
| 2003/0166556 | A1 | 9/2003 | Khan et al. |
| 2003/0186244 | A1 | 10/2003 | Margus et al. |
| 2003/0215434 | A1 | 11/2003 | Khan et al. |
| 2003/0219425 | A1 | 11/2003 | Khan et al. |
| 2003/0220257 | A1 | 11/2003 | Benner et al. |
| 2003/0220258 | A1 | 11/2003 | Benner et al. |
| 2003/0220259 | A1 | 11/2003 | Benner et al. |
| 2003/0220260 | A1 | 11/2003 | Khan et al. |
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |
| 2004/0072246 | A1 | 4/2004 | Martin et al. |
| 2004/0208885 | A1 | 10/2004 | Khan et al. |
| 2005/0037430 | A1 | 2/2005 | Khan et al. |
| 2005/0107314 | A1 | 5/2005 | Gorczynski et al. |
| 2005/0119184 | A1 | 6/2005 | Khan et al. |
| 2005/0214943 | A1 | 9/2005 | Khan et al. |
| 2005/0227925 | A1 | 10/2005 | Benner et al. |
| 2006/0111292 | A1 | 5/2006 | Khan et al. |
| 2006/0142205 | A1 | 6/2006 | Benner et al. |
| 2006/0173162 | A1 | 8/2006 | Djurup et al. |
| 2006/0275255 | A1 | 12/2006 | Gudkov |
| 2007/0054860 | A1 | 3/2007 | Benner et al. |
| 2007/0111948 | A1 | 5/2007 | Turdiev |
| 2007/0197447 | A1 | 8/2007 | Khan et al. |
| 2007/0219138 | A1 | 9/2007 | Benner et al. |
| 2008/0027007 | A1 | 1/2008 | Benner et al. |
| 2008/0076714 | A1 | 3/2008 | Khan et al. |
| 2008/0153755 | A1 | 6/2008 | Khan et al. |
| 2008/0171094 | A1 | 7/2008 | Benner et al. |
| 2008/0176243 | A1 | 7/2008 | Khan et al. |
| 2008/0194489 | A1 | 8/2008 | Khan et al. |
| 2008/0242618 | A1 | 10/2008 | Khan et al. |
| 2008/0242837 | A1 | 10/2008 | Khan et al. |
| 2008/0267936 | A1 | 10/2008 | Khan et al. |
| 2008/0267967 | A1 | 10/2008 | Gorczynski et al. |
| 2008/0306009 | A1 | 12/2008 | Khan et al. |
| 2009/0042807 | A1 | 2/2009 | Khan et al. |
| 2009/0093398 | A1 | 4/2009 | Bollekens et al. |
| 2009/0227505 | A1 | 9/2009 | Khan et al. |
| 2009/0281033 | A1 | 11/2009 | Benner et al. |
| 2009/0291901 | A1 | 11/2009 | Benner et al. |
| 2010/0004172 | A1 | 1/2010 | Khan et al. |
| 2010/0297258 | A1 | 11/2010 | Benner et al. |
| 2011/0009344 | A1 | 1/2011 | Benner et al. |
| 2011/0105415 | A1 | 5/2011 | Khan et al. |
| 2011/0113053 | A1 | 5/2011 | Khan et al. |

FOREIGN PATENT DOCUMENTS

| | | |
|---|---|---|
| WO | WO 96/04008 | 2/1996 |
| WO | WO 96/33218 | 10/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 98/06742 | 2/1998 |
| WO | WO 98/34631 A1 | 8/1998 |
| WO | WO 98/35691 | 8/1998 |
| WO | WO 99/31227 | 6/1999 |
| WO | WO 99/59617 | 11/1999 |
| WO | WO 00/17348 | 3/2000 |
| WO | WO 01/10907 A2 | 2/2001 |
| WO | WO 01/11048 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 02/092781 A2 | 11/2002 |
| WO | WO 03/029292 A2 | 4/2003 |
| WO | WO 2004/093897 | 11/2004 |
| WO | WO 2005/011723 A1 | 2/2005 |
| WO | WO 2005/097163 | 10/2005 |
| WO | WO 2006/069198 A1 | 6/2006 |
| WO | WO2009/126037 A1 | 10/2009 |

OTHER PUBLICATIONS

Office Action for U.S. Appl. No. 10/409,032 dated Jan. 15, 2008.
Office Action for U.S. Appl. No. 10/409,032 dated Aug. 20, 2008.
Office Action for U.S. Appl. No. 10/409,032 dated Jun. 1, 2009.
Office Action for U.S. Appl. No. 11/037,972 dated Oct. 11, 2007.
Office Action for U.S. Appl. No. 11/037,972 dated Jun. 4, 2008.
Office Action for U.S. Appl. No. 11/037,972 dated Dec. 12, 2008.
Office Action for U.S. Appl. No. 11/446,458 dated Jun. 15, 2007.

Office Action for U.S. Appl. No. 11/446,458 dated Jan. 11, 2008.
Office Action for U.S. Appl. No. 11/446,458 dated Jul. 28, 2008.
Office Action for U.S. Appl. No. 11/446,458 dated Sep. 2, 2008.
Office Action for U.S. Appl. No. 11/446,458 dated Mar. 6, 2009.
Office Action for U.S. Appl. No. 11/481,423 dated Jan. 31, 2008.
Office Action for U.S. Appl. No. 11/593,329 dated Apr. 6, 2009.
Office Action for U.S. Appl. No. 11/600,294 dated Apr. 3, 2009.
Office Action for U.S. Appl. No. 11/715,314 dated Feb. 26, 2009.
Office Action for U.S. Appl. No. 11/715,314 dated Aug. 14, 2009.
Office Action for U.S. Appl. No. 11/975,284 dated Dec. 29, 2008.
Office Action for U.S. Appl. No. 11/975,284 dated Oct. 1, 2009.
Office Action for U.S. Appl. No. 11/982,292 dated May 18, 2009.
Office Action for U.S. Appl. No. 11/982,292 dated Aug. 28, 2009.
Endo et al., Plasma endotoxin and cytokine concentrations in patients with hemorrhagic shock, Crit Care Med, 1994, pp. 949-955, vol. 22L.
Hummel et al., Topical and Systemic Antibacterial Agents in the Treatment of Burns, Annals Surg., 1970, pp. 370-384, vol. 173, No. 3.
Lider et al., Suppression of Experimental Autoimmune Diseases and Prolongation of Allograft Survival by Treatment of Animals with Low Doses of Heparin, J. Clin. Invest., 1989, pp. 752-756, vol. 83.
Molina et al., Central Sympathetic Modulation of Tissue Cytokine Response to Hemorrhage, Neuroimmunomodulation, 1999, pp. 193-200, vol. 6.
Morales et al., Reversal by Vasopressin of Intractable Hypotension in the Late Phase of Hemorrhage Shock, Circulation, 1999, pp. 226-229, vol. 100.
Saavedra et al., Targeting Nitric Oxide Delivery in Vivo, J. Medicinal Chemistry, Jun. 20, 1997, pp. 1947-1954, vol. 40, No. 13.
Office Action for U.S. Appl. No. 12/288,935 dated Jun. 13, 2011.
Abeyama et al., A role of NF-κb-dependent gene transactivation in sunburn. The Journal of Clinical Investigation, vol. 105, No. 12, pp. 1751-1759, Jun. 2000.
Abraham, E., Coagulation Abnormalities in Acute Lung Injury and Sepsis, Am. J. Respir. Cell Mol. Biol., 2000, pp. 401-404, vol. 22.
Adib-Conquy et al., NF-κB Expression in Mononuclear Cells in Patients with Sepsis Resembles That Observed in Lipopolysaccharide Tolerance, Am. J. Respir. Crit. Care Med., 2000, pp. 1877-1883, vol. 162.
Agawal et al., Acute Renal Failure, American Family Physician, 2000, pp. 2077-2088, vol. 61, corresponding to web version of p. 1-12.
Albini et al., Old drugs as novel angiogenesis inhibitors: Preclinical studies with NAC, hCG, EGCG and somatostatin, Clinical & Experimental Metastasis, 1999, pp. 739, vol. 17.
Arima et al., IL-2-Induced Growth of CD8+ T Cell Prolymphocytic Leukemia Cells Mediated by NF-kappaB Induction and IL-2 Receptor alpha Expression, Leukemia Research, 1998, pp. 265-273, vol. 22, No. 3.
Baeuerle et al., Function and Activation of NF-κb in the Immune System, Annu. Rev. Immunol., 1994, pp. 141-179, vol. 12.
Barton et al., Protective Role of Interleukin 6 in the Lipopolysaccharide-Galactosamine Septic Shock Model, Infection and Immunity, Apr. 1993, pp. 1496-1499, vol. 61, No. 4.
Bastin et al., Salt Selection and Optimisation Procedures for Pharmaceutical new Chemical Entities, Org. Proc. Res. Develop. 2000, pp. 427-435, vol. 4.
Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.
Bethea et al., Traumatic Spinal Cord Injury Induces Nuclear Factor-κB Activation, The Journal of Neuroscience, May 1, 1998, pp. 3251-3260, vol. 18, No. 9.
Blackwell et al., The Role of Nuclear Factor-κB in Cytokine Gene Regulation, Am. J. Respir. Cell Mol. Biol., 1997, pp. 3-9, vol. 17.
Bodfish et al., Treating the Core Features of Autism: Are We There Yet? Mental Retardation and Developmental Disabilities Research Reviews, 2004, pp. 318-326, vol. 10.
Borchardt, RT, Optimizing oral absorption of peptides using prodrug strategies, Journal of Controlled Release, Nov. 1999, pp. 231-238, vol. 62.
Bradham et al., Activation of nuclear factor-κB during orthotopic liver transplantation in rats is protective and does not require Kuppfer cells, Liver Transplantation and Surgery, Jul. 1999, pp. 282-293, vol. 5, No. 4.
Brown et al., Two Forms of NF-kappaB1 (p105/p50) in Murine Macrophages: Differential Regulation by Lipopolysaccharide, Interleukin-2, and Interferon-gamma, Journal of Interferon and Cytokine Research, 1997, pp. 295-306, vol. 17.
Burdelya et al., An agonist of toll-like receptor 5 has radioprotective activity in mouse and primate models, Abstract, Science, Apr. 11, 2008, pp. 226-230, vol. 320, No. 5873.
Burdelya et al., NF-kappaB activating proteins as radioprotectants: Derivatives of Flagellin from Salmonella protect mice from hematopoietic and gastrointestinal Radiation Syndromes, Cleveland Biolabs, Inc.
Capizzi, Investigational New Drugs, 1996, 14:249-256.
Christman et al., Nuclear factor kappaB: a pivotal role in the systemic inflammatory response syndrome and new target for therapy, Intens Care Med, 1998, pp. 1131-1138, vol. 24.
Clerici et al., Single-cell analysis of cytokine production shows different immune profiles in multiple sclerosis patients with active or quiescent disease. Journal of Neuroimmunology, vol. 121, pp. 33-101, 2001.
Cleveland BioLabs, Inc., Radiation Antidote for Defense, (visited Apr. 16, 2008) <http://www.cbiolabs.com/Applications.php.
Connelly et al., Biphasic Regulation of NF-κb Activity Underlies the Pro- and Anti-inflammatory Actions of Nitric Oxide, The Journal of Immunology, 2001, pp. 3873-3881, 166, The American Association of Immunologists, USA.
Cook et al., Modified total lymphoid irradiation and low dose coricosteroids in progressive multiple sclerosis, Journal of Neurological Sciences, vol. 152, pp. 172-181, 1997.
Corvino et al., Availability, stability and sterility of pralidoxime for mass casualty use, Abstract, Ann Emerg Med., Mar. 2006, pp. 272-277, vol. 47, No. 3.
Cui et al., Am. J. Physiol. Integr. Comp. Physiol., 2004, pp. R699-R709, vol. 286.
Daemen et al., Ischemia-reperfusion-induced IFN-gamma up-regulation: involvement of IL-12 and IL-13, The Journal of Immunology, 1999, pp. 5506-5510, vol. 162.
De Saizieu et al., Journal of Bacteriology, vol. 182, No. 17, pp. 4696-4703, Sep. 2000.
Dechend et al., Oncogene, vol. 18, pp. 3316-3323, 1999.
Dietrich et al., Postischemic hypothermia and IL-10 treatment provide long-lasting neuroprotection of CA1 hippocampus following transient global ischemia in rats. Experimental Neurology, 1999, pp. 444-450, vol. 158.
Donnahoo et al., Early kidney TNF-alpha expression mediates neutrophil infiltration and injury after renal ischemia-reperfusion, American Journal of Physiology, Sep. 1999, pp. R922-R929, vol. 277, No. 3, Pt. 2.
Dwinnell et al., Atlas of Diseases of the Kidney, Blackwell Sciences, 1999, pp. 12.1-12.12, Ch. 12.
Eckardt et al., Hypoxia-induced accumulation of erythropoietin mRNA in isolated hepatocytes is inhibited by protein kinase C, Pflugers Archiv., 1994, pp. 21-30, vol. 426.
Emmel et al., Cyclosporin A Specifically Inhibits Function of Nuclear Proteins Involved in T Cell Activation, Science, Dec. 22, 1989, pp. 1617-1620, vol. 246.
Engles et al., Exogenous human recombinant interleukin-10 attenuates hindlimb ischemia-reperfusion injury, Journal of Surgical Research, 1997, pp. 425-428, vol. 69.
Epinat et al., Diverse agents act at multiple levels to inhibit the Rel/NF-kappaB signal transduction pathway, Oncogene, 1999, pp. 6896-6909, vol. 18.
Fassio et al., Transforming Growth Factor Alpha and Its Receptor in Neural Retina, Investigative Ophthalmology & Visual Science, Sep. 1989, pp. 1916-1922, vol. 30, No. 9.
Faust et al., Disseminated intravascular coagulation and purpura fulminans secondary to infection, Bailliere's Clinical Haematology, 2000, 179-197, vol. 13. No. 2.

Flores et al., NFkappaB and AP-1 DNA binding activity in patients with multiple sclerosis. J. Neuroimmunol. vol. 135, No. 1-2, pp. 141-147, Feb. 2003.

Friedlander, Tackling anthrax, Nature, Nov. 8, 2001, pp. 160-161, vol. 414.

Garkavtsev et al., Suppression of the novel growth inhibitor p33ING1 promotes neoplastic transformation, Nature Publishing Group, Dec. 14, 1996, pp. 415-420.

Garkavtsev et al., The candidate tumour suppressor p33ING1 cooperates with p53 in cell growth control, Nature, Jan. 15, 1998, pp. 295-298, vol. 391.

GenBank Accession No. NP_000728, GI: 4502789, publicly available Apr. 2007.

Gould, Salt selection for basic drugs, Int. J. Pharm., 1986, pp. 201-217, vol. 33.

Gudkov et al., The role of p53 in determining sensitivity to radiotherapy, Nature Reviews, Feb. 2003, pp. 117-129, vol. 3.

Gudkov, Andrei V., Cancer drug discovery: the wisdom of imprecision, Nature Medicine, Dec. 2004, 1298-00, vol. 10, No. 12.

Gudkov, Andrei V., Converting p53 from a killer into a healer, Nature Medicine, Nov. 2002, pp. 1196-1198, vol. 8, No. 11.

Han et al., Cholecystokinin induction of mob-1 chemokine expression in pancreatic acinar cells requires NF-kappaB activation, American Journal of Physiology, Jul. 1999, vol. 277, pp. C74-C82.

http://www.rxlist.com/cgi/generic/chorionic.htm—RX List.com entry for hCG/Pregnyl, (2008).

Huang et al., Ischemia-reperfusion and immediate T cell responses, Cellular Immunology, 2007, pp. 4-11, vol. 248.

Husek et al., Rapid screening of urinary proline-hydroxyproline dipeptide in bone turnover studies, Abstract, J. Chromatogr B Analyt Technol Biomed Life Sci., Feb. 5, 2002, pp. 169-174, vol. 767, No. 1.

Ichiyama et al., Systemically administered alpha-melanocyte-stimulating peptides inhibit NF-kappaB activation in experimental brain inflammation, Brain Research, Jul. 1999, pp. 31-37, vol. 836.

Ivanov et al., Hemoglobin as a Source of Endogenous Bioactive Peptides: The Concept of Tissue-Specific Peptide Pool, Biopolymers, 1997, pp. 171-188, vol. 39.

Iyer et al., The transcriptional program in the response of human fibroblasts to serum, Science, Jan. 1999, pp. 83-87, vol. 283, No. 5398.

Jimenez-Garza et al., Early Effects of Modulating Nuclear factor-kappaB Activation on Traumatic Spinal Cord Injury in Rats, Ann. N.Y Acad. Sci., 2005, pp. 148-150, vol. 1053.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kachra et al., Low Molecular Weight Components but Not Dimeric HCG Inhibit Growth and Down-Regulate AP-1 Transcription Factor in Kaposi's Sarcoma Cells, Endocrinology, 1997, pp. 4038-4041, vol. 138, No. 9.

Kalns et al., Biochem. Biophys. Res. Comm., 2002, pp. 41-44, vol. 292.

Kalns et al., Biochem. Biophys. Res. Comm., 2002, pp. 506-509, vol. 297.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Kato et al., Reduced hepatic ischemia/reperfusion injury by IL-4: potential anti-inflammatory role of STAT6, Inflammation Research, Jun. 2000, pp. 275-279, vol. 49, No. 6.

Keeton and Gould, Biological Science, 5th Ed., New York, W.W. Norton & Company, Inc. 1993, p. 4.

Keller et al., Human Chorionic Gonadotropin (hCG) is a Potent Angiogenic Factor for Uterine Endothelial Cells in Vitro, Placenta, Jul. 1999, pp. A37, vol. 20, No. 5-6.

Khan et al., Inhibition of Diabetes in NOD Mice by Human Pregnancy Factor, Human Immunology, Dec. 2001, pp. 1315-1323, vol. 62, No. 12.

Khan et al., Inhibition of Septic Shock in Mice by an Oligopeptide From the β-Chain of Human Chorionic Gonadotrophin Hormone, Human Immunology, Jan. 2002, pp. 1-7, vol. 63, No. 1.

Khavinson et al, Gerontological Aspects of Genome Peptide Regulation, 2005, S. Karger AG, Basel, Switzerland.

Khavinson et al., Effects of Livagen Peptide on Chromatin Activation in Lymphocytes from Old People, Bulletin of Experimental Biology and Medicine, Oct. 2002, pp. 389-392, vol. 134, No. 4.

Khavinson et al., Effects of Short Peptides on Lymphocyte Chromatin in Senile Subjects, Bulletin of Experimental Biology and Medicine, Jan. 2004, pp. 78-81, vol. 137, No. 1.

Khavinson et al., Epithalon Peptide Induces Telomerase Activity and Telomere Elongation in Human Somatic Cells, Bulletin of Experimental Biology and Medicine, Jun. 2003, pp. 590-592, vol. 135, No. 6.

Khavinson et al., Inductive Activity of Retinal Peptides, Bulletin of Experimental Biology and Medicine, Nov. 2002, pp. 482-484, vol. 134, No. 5.

Khavinson et al., Mechanisms Underlying Geroprotective Effects of Peptides, Bulletin of Experimental Biology and Medicine, Jan. 2002, pp. 1-5, vol. 133, No. 1.

Khavinson et al., Peptide Promotes Overcoming of the Division Limit in Human Somatic Cell, Bulletin of Experimental Biology and Medicine, May 2004, pp. 503-506, vol. 137, No. 5.

Kidd et al., Autism, An Extreme Challenge to Integrative Medicine. Part II: Medical Management, Alternative Medicine Review, 2002, pp. 472-499, vol. 7, No. 6.

Kronfol et al., Cytokines and the Brain: Implications for Clinical Psychiatry, Am. J. Psychiatry, May 2000, pp. 683-694, vol. 157, No. 5.

Lane et al., Interleukin-10 reduces the systemic inflammatory response in a murine model of intestinal ischemia/reperfusion, Surgery, 1997, pp. 288-294, vol. 122, No. 2.

Lang et al., Induction of apoptosis in Kaposi's sarcoma spindle cell cultures by the subunits of human chorionic gonadtropin, AIDS, 1997, pp. 1333-1340, vol. 11, No. 11.

Le Moine et al., Cold liver ischemia-reperfusion injury critically depends on liver T cells and is improved by donor pretreatment with interleukin 10 in mice, Hepatology, 2000, pp. 1266-1274, vol. 31, No. 6.

Li et al., NF-kappaB Regulation in the Immune System, Nature Reviews/Immunology, Oct. 2002, pp. 725-734, vol. 2.

Lin et al., The Journal of Biological Chemistry, vol. 270, No. 24, pp. 14255-14258, Jun. 1995.

Lunardi-Iskandar et al., Effects of a urinary factor from women in early pregnancy on HIV-a, SIV and associated disease, Nature Medicine, Apr. 1998, pp. 428-434, vol. 4, No. 4.

Lutterova et al., Marked difference in tumor necrosis factor-alpha expression in warm ischemia- and cold ischemia-reperfusion of the rat liver, Cryobiology, 2000, pp. 301-314, vol. 41.

Malek-Ahmadi, P., Role of Cytokines in Psychopathology: Therapeutic Implications, Drug News Prospects, Jun. 1998, pp. 271-276, vol. 11, No. 5.

Malyak et al., Characterization of a Low Molecular Weight Isoform of IL-1 Receptor Antagonist, The Journal of Immunology, 1998, pp. 1997-2003, vol. 161.

Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

McBean et al., Rodent Models of Global Cerebral Ischemia: A Comparison of Two-Vessel Occlusion and Four-Vessel Occlusion, Gen. Pharmac., 1998, pp. 431-434, vol. 30, No. 4.

McDonald et al., Interleukin-15 (IL-15) Induces NF-kappaB Activation and IL-8 Production in Human Neutrophils, Blood, Dec. 15, 1998, pp. 4828-4835, vol. 92, No. 12.

MedlinePlus, Medical Encyclopedia: autoimmune disorders (www.nlm.gov/medlineplus/ency/article/000816.htm), (2005).

Medzhitov, Toll-like Receptors and Innate Immunity, Nature Reviews/Immunology, Nov. 2001, pp. 135-145, vol. 1.

Merck Index, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Morozov et al., Natural and Synthetic Thymic Peptides as Therapeutics for Immune Dysfunction, Int. J. Immunopharmac., 1997, pp. 501-505, vol. 19, No. 9/10.
Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.
Muchmore et al., Purification and Characterization of a Mannose-Containing Disaccharide Obtained from Human Pregnancy Urine, Journal of Experimental Medicine, Dec. 1984, pp. 1672-1685, vol. 160.
NCBI Accession No. AAI06724, version Oct. 6, 2006.
Neely et al., Then and now: Studies using a burned mouse model reflect trends in burn research over the past 25 years, Burns, 1999, pp. 603-609, vol. 25.
Ngo et al., The protein folding problem and tertiary structure prediction, 1994, pp. 492-494.
Ohlsson et al., Interleukin-1 Receptor Antagonist Reduces Mortality from Endotoxin Shock, Nature, Dec. 6, 1990, pp. 550-552, vol. 348.
Oka et al., Immunosuppression in organ transplantation, Japanese Journal of Pharmacology, vol. 71, No. 2, pp. 89-100, Jun. 1996.
Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.
Padmos et al., A discriminating messenger RNA signature for bipolar disorder formed by an aberrant expression of inflammatory genes in monocytes, Arch Gen Psychiatry, Apr. 2008, pp. 395-407, vol. 65, No. 4.
Pan et al., Bradykinin Stimulates NF-κb Activation and Interleukin 1β Gene Expression in Cultured Human Fibroblasts, J. Clin. Invest., Nov. 1996, pp. 2042-2049, vol. 98, No. 9, The American Society for Clinical Investigation, Inc.
Partial European Search Report for 02 763 111.8 dated Nov. 23, 2007.
Patil et al., The Study of the Effect of Human Chorionic Gonadotrophic (HCG) Hormone on the Survival of Adrenal Medulla Transplant in Brain. Preliminary Study, Acta Neurochir (WIEN), 1987, pp. 76-78, vol. 87.
PCT International Search Report and Written Opinion, PCT/NL2007/050092, dated Jul. 6, 2007.
PCT International Search Report, International Application No. PCT/NL02/00639, mailed Aug. 4, 2003.
PCT International Search Report, PCT/CA97/00568, dated Apr. 30, 1998.
PCT International Search Report, PCT/EP2005/003707, dated Jul. 5, 2005.
PCT International Search Report, PCT/NL01/00259, dated Dec. 18, 2001.
Pellizzari et al., FEBS Letters, 1999, pp. 199-204, vol. 462.
Qin et al., Nuclear Factor κB Nuclear Translocation Upregulates c-Myc and p53 Expression during NMDA Receptor-Mediated Apoptosis in Rat Striatum, The Journal of Neuroscience, May 15, 1999, pp. 4023-4033, vol. 19, No. 10.
Quillan et al., Combinatorial diffusion assay used to identify topically active melanocyte-stimulating hormone receptor antagonists, PNAS, Mar. 1995, pp. 2894-2898, vol. 92, USA.
"RDT&E Budget item justification sheet" StartDateMarker 1999, EndDateMarker Retrieved from the Internet: URL:http://www.dtic.mil/descriptivesum/Y2000/OSD/PE0602787D.pdf>.
Redon et al., Global variation in copy number in the human genome, Nature, Nov. 23, 2006, pp. 444-454, vol. 444.
Riera et al., Neutrophils accentuate renal cold ischemia-reperfusion injury. Dose-dependent protective effect of platelet-activating factor receptor antagonist, The Journal of Pharmacology and Experimental Therapeutics, 1997, pp. 786-794, vol. 280, No. 2.
Rodriguez et al., Expression of human HLA-B27 transgene alters susceptibility to murine theiler's virus-induced demylenination, 1991, vol. 146, pp. 2596-2602.
Rohrig et al., Growth-stimulating Influence of Human Chorionic Gonadotropin (hCG) on *Plasmodium falciparum* in vitro, Zentralblatt Bakt, 1999, pp. 89-99, vol. 289.

Samaniego et al., Induction of Programmed Cell Death in Kaposi's Sarcoma Cells by Preparations of Human Chorionic Gonadotropin, Journal of the National Cancer Institute, Jan. 20, 1999, pp. 135-143, vol. 91, No. 2.
Selzman et al., Interleukin-10 inhibits postinjury tumor necrosis factor-mediated human vascular smooth muscle proliferation, Journal of Surgical Research, 1998, pp. 352-356, vol. 80.
Sharma, Septic Shock, (visited Sep. 27, 2007 <http://www.emedicine.com/MED/topic2101.htm>.
Slater et al., Decreased Mortality of Murine Graft-Versus-Host Disease by Human Chorionic gonadotropin, Transplantation, Jan. 1977, pp. 103-104, vol. 23, No. I.
Smith et al., Recent developments in drug therapy for multiple sclerosis, Multiple Sclerosis, 1999, pp. 110-120, vol. 5.
Sovak et al., Aberrant nuclear factor-kappa B/Rel expression and the pathogenesis of breast cancer, The Journal of Clinical Investigation, Dec. 1997, pp. 2952-2960, vol. 100, No. 12.
Strom et al., Small-molecule inhibitor of p53 binding to mitochondria protects mice from gamma radiation, Nature Chemical Biology, Sep. 2006, pp. 474-479, vol. 2, No. 9.
Szinicz, L., History of chemical and biological warfare agents, Abstract, Toxicology, Oct. 30, 2005, pp. 167-181, vol. 214, No. 3.
Tak et al., NF-kappaB: a key role in inflammatory diseases, J Clin Invest., 2001, pp. 7-11, vol. 107.
Tan et al., The role of activation of nuclear factor-kappa B of rat brain in the pathogenesis of experimental allergic encephalomyelitis, Acta Physiol Sinica, 2003, pp. 58-64, vol. 55.
Thibonnier et al., Cytoplasmic and nuclear signaling pathways of VI-vascular vasopressin receptors, Regulatory Peptides, 1993, pp. 79-84, vol. 45.
Tovey et al., Mucosal Cytokine Therapy: Marked Antiviral and Antitumor Activity, J. Interferon Cytokine Res., 1999, pp. 911-921, vol. 19.
Traystman, R., Animal Models of Focal and Global Cerebral Ischemia, ILAR Journal, 2003, pp. 85-95, vol. 44, No. 2.
Valore et al., Human b-Defensin-1: An antimicrobial Peptide of Urogenital Tissues, J. Clin. Invest., Apr. 1998, pp. 1633-1642, vol. 101, No. 8.
Wallraff et al., Urinary Excretion of Amino Acids in Pregnancy, J. Clinc. Invest., 1950, pp. 1542-1544, vol. 29.
Weinberger et al., Mechanisms Mediating the Biologic Activity of Synthetic Proline, Glycine, and Hydroxyproline Polypeptides in Human Neurophils, Mediators of Inflammation, 2005, pp. 31-38, vol. 1.
Wu et al., Gonadotropin-Releasing Hormone (GNRH) Cleavage Products are Involved in the Regulation of GNRH Gene Expression in the GT1-7 Neuronal Cell Line, Society for Neuroscience Abstracts, Nov. 4, 2000, pp. 7.8, XP009091566, vol. 26, No. 1-2.
Wulczyn et al., The NF-κB/Rel and 1kB gene families: mediators of immune response and inflammation, J. Mol. Med., 1996, pp. 749-769, vol. 74, No. 12.
Yamamoto et al., Role of the NF-κB Pathway in the Pathogenesis of Human Disease States, Current Molecular Medicine, Jul. 2001, pp. 287-296, vol. 1, No. 3.
Yang et al., Increased cortical nuclear factor κb (NF-κB) DNA binding activity after traumatic brain injury in rats, Neuroscience Letters, 1995, pp. 101-104, vol. 197.
Zhou et al., Transplantation tolerance in NF-κB-impaired mice is not due to regulation but is prevented by transgenic expression of Bcl-xL. The Journal of Immunology, vol. 174, No. 6, pp. 3447-3453, Mar. 2005.
U.S. Appl. No. 10/028,075, filed Dec. 21, 2001, Khan et al., Gene Regulator.
U.S. Appl. No. 10/409,032, filed Apr. 8, 2003, Benner et al., Treatment of Trauma.
U.S. Appl. No. 10/409,642, filed Apr. 8, 2003, Benner et al., Treatment of Ischemic Events.
U.S. Appl. No. 10/817,756, filed Apr. 2, 2004, Khan et al., Gene Regulatory Peptides.
U.S. Appl. No. 10/821,240, filed Apr. 8, 2004, Khan et al., Methods and Uses for Protein Breakdown Products.
U.S. Appl. No. 10/821,256, filed Apr. 8, 2004, Benner et al., Compositions Capable of Reducing Elevated Blood Urea Concentration.

U.S. Appl. No. 11/037,972, filed Jan. 18, 2005, Khan et al., Immunoregulator.
U.S. Appl. No. 11/346,450, filed Feb. 2, 2006, Benner et al., Compositions Capable of Reducing Elevated Blood Urea Concentration.
U.S. Appl. No. 11/446,458, filed Jun. 2, 2006, Drexhage et al., Method to Diagnose or Screen for Inflammatory Diseases.
U.S. Appl. No. 11/481,423, filed Jul. 5, 2006, Khan et al., Treatment for Tumors.
U.S. Appl. No. 11/593,329, filed Nov. 6, 2006, Benner et al., Treatment of Ischemic Events.
U.S. Appl. No. 11/600,294, filed Nov. 15, 2006, Khan et al., Oligopeptide Acetate and Formulations Thereof.
U.S. Appl. No. 11/715,314, filed Mar. 7, 2007, Benner et al., Control of Radiation Injury.
U.S. Appl. No. 11/859,265, filed Sep. 21, 2007, Khan et al., Immunoregulatory Compositions.
U.S. Appl. No. 11/975,284, filed Oct. 17, 2007, Khan et al., Treatment for Tumors.
U.S. Appl. No. 11/981,491, filed Oct. 30, 2007, Khan et al., Treatment of Iatrogenic Disease.
U.S. Appl. No. 11/981,505, filed Oct. 30, 2007, Benner et al., Treatment of Burns.
U.S. Appl. No. 11/982,170, filed Oct. 31, 2007, Khan et al., Administration of Gene-Regulatory Peptides.
U.S. Appl. No. 11/982,292, filed Oct. 31, 2007, Khan et al., Treatment of Neurological Disorders.
U.S. Appl. No. 11/982,293, filed Oct. 31, 2007, Khan et al., Stratification.
U.S. Appl. No. 11/986,043, filed Oct. 30, 2007, Khan et al., Peptide Compositions.
U.S. Appl. No. 12/001,035, filed Dec. 6, 2007, Khan et al., Gene Regulator.
U.S. Appl. No. 12/069.401, filed Feb. 8, 2008, Khan et al., Immunoregulatory Compositions.
U.S. Appl. No. 12/069,741, filed Feb. 12, 2008, Khan et al., Treatment of Trauma-Hemorrhage With Short Oligopeptides.
U.S. Appl. No. 12/074,020, filed Feb. 29, 2008, Khan et al., Oligopeptide Treatment of Ischemia-Reperfusion Injury.
U.S. Appl. No. 12/083,472, filed Apr. 11, 2008, Drexhage et al., Method to Diagnose or Screen for Inflammatory Diseases.
U.S. Appl. No. 12/288,935, filed Oct. 24, 2008, Benner et al., Control of Radiation Injury.
U.S. Appl. No. 12/383,849, filed Mar. 27, 2009, Khan et al., Compositions for Mucosal and Oral Administration Comprising HCG Fragments.
U.S. Appl. No. 12/386,061, filed Apr. 9, 2009, Khan et al., Methods and Uses for Protein Breakdown Products.
U.S. Appl. No. 12/386,135, filed Apr. 14, 2009, Khan et al., Gene Regulator.
Altuvia et al., A structure-based approach for prediction of MHC-binding peptides, Methods, 2004, pp. 454-459, vol. 34.
Austin et al., C-terminal motif prediction in eukaryotic proteomes using comparative genomics and statistical over-representation across protein families, BMC Genomics, 2007, 8:191.
Kunik et al., Functional Representation of Enzymes by Specific Peptides, PLOS Computational Biology, Aug. 2007, pp. e167; vol. 3, No. 8.

Altavilla, et al., Tumour necrosis factor-α as a target of melanocortins in haemorrhagic sheok, in the anaesthetized rat. British Journal of Pharmacology. 1998. pp. 1587-1590. vol. 24. No. 8.
Audran, M., Iatrogenic Demineralizing osteophathies. Presse Med. Feb. 12, 1994: 23(6): 271-3.
Babu, V.V. Suresh (Synthetic Communications 29(1), 79-91, 1999).
Bardin, et al., Nephrogenic systemic fibrosis, Current Opinion in Rheumatology 2010, 22:54-58.
Chiao, et al., α-Melanocyte-stimulating Honnone Protects Against Renal Injury after Ischenia in Mice and Rats, The Amercian Society for Clincial Investigation, Inc., vol. 99, No. 6; Mar. 1997, 1165-1172.
Hunsinger, et al., Is there a basis for novel pharmacotherapy of autism?. Life Sciences 67 (2000) 1667-1682.
Invernizzi, et al. Osteoporosis in Parkinson's disease. Parkinsonism Relat Disord. Jun. 2009: 15(5): 339-346.
Jensen, et al. Xerostomia and hypofunction of the salivary glands in cancer therapy, Support Care Cancer (2003) 11:207-225.
Kintzel, PE., Anticancer drug-induced kidney disorders, Drug Saf. Jan. 2001; 24(1): 19-38.
Lyons, II, et al., Diabetes Management: Current Diagnostic Criteria, Drug Therapies, and State Legislation: The American Journal of Managed Care vol. 3 No. 10: Oct. 1997; pp. 1599-1612.
Manna,e t al.. α-Melanocyte-Stimulating Hormone Inhibits the Nuclear Transcription Factor NF-κB Activation Induced by Various Inflammatory Agents, The American Association of the Immunologists. pp. 2873-2880, (1998).
Rizzo et al., Wild-type p53 differentially affects tumorigenic and metastatic potential of murine metastatic cell variants, Clin. Exp. Metastasis, 1993, pp. 368-376, vol. 11.
Roice, M. (Tetrahedron 56(23), 3725-3734, 2000).
Toyooka, et al., Iatrogenic neuropathies. Current Opinion in Neurology 2009; 22:475-479.
Van Holde, Physical Biochemistry. pp. 3947. Prentice-Hall. 1971.
Waldum, et al., Antiulcer Drugs and Gastric Cancer, Digestive Diseases and Sciences, vol. 50 Supplement I (Oct. 2005): pp. S39-S44.
Will, Robert G. Acquired prion disease: Iatrogenci CJD, variant CJD, kuru, British Medical Bulletin 2003: 66: 255-265.
Yoshida, International Journal of Pharmaceutics, 2007, pp. 142-147, vol. 337, No. 1-2.
Office Action for U.S. Appl. No. 11/481,423 dated Jan. 31, 2008
Office Action for U.S. Appl. No. 11/481,423 dated Apr. 16, 2009.
Office Action for U.S. Appl. No. 11/481,423 dated Jul. 24, 2008.
Office Action for U.S. Appl. No. 11/593,329 dated Mar. 5, 2010.
Office Action for U.S. Appl. No. 11/600,294 dated Dec. 17, 2009.
Office Action for U.S. Appl. No. 11/975,284 dated Apr. 16, 2010.
Office Action for U.S. Appl. No. 11/981,505 dated May 27, 2009.
Office Action for U.S. Appl. No. 11/981,505 dated Sep. 29, 2009.
Office Action for U.S. Appl. No. 11/986,043 dated Nov. 20, 2009.
Office Action for U.S. Appl. No. 11/986,043 dated Feb. 18, 2010.
Notice of Allowance for U.S. Appl. No. 11/715,314 dated Apr. 12, 2010.
Notice of Allowance for U.S. Appl. No. 11/981,505 dated Mar. 25, 2010.

* cited by examiner

FIG. 4

CONTROL OF RADIATION INJURY

CROSS-REFERENCE TO RELATED APPLICATIONS

This application is a divisional of U.S. patent application Ser. No. 11/715,314, filed Mar. 7, 2007, now U.S. Pat. No. 7,795,226, which application claims the benefit under 35 U.S.C. §119(e) of U.S. Provisional Patent Application Ser. No. 60/811,878, filed Jun. 7, 2006, and U.S. Provisional Patent Application Ser. No. 60/779,896, filed Mar. 7, 2006, and claims priority to European Patent Application Serial No. EP 06076181.4, filed Jun. 7, 2006, the contents of the entirety of each of which are hereby incorporated herein by this reference.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing.txt," which is 23 KB and created on Sep. 21, 2007.

TECHNICAL FIELD

The invention relates to the field of drug development against acute radiation injury caused by exposure to high-energy electromagnetic waves (X-rays, gamma rays) or particles (alpha particles, beta particles, neutrons). To date, there is no effective drug to ameliorate radiation injury after accidental exposure to ionizing irradiation.

BACKGROUND

Radiation injury is damage to tissues caused by exposure to radiation. Herein, "radiation" refers to ionizing radiation caused by high-energy electromagnetic waves (X-rays, gamma rays) or particles (alpha particles, beta particles, neutrons). Such radiation is emitted by radioactive substances (radioisotopes), such as uranium, radon, and plutonium. Such radiation is also produced by man-made sources, such as x-ray and radiation therapy machines. Radiation dose is measured in several different units, but all relate to the amount of energy deposited. The units include the roentgen (R), the gray (Gy), and the sievert (Sv). The sievert and gray are similar, except the sievert takes into account the biologic effects of different types of radiation. The two main types of radiation exposure are irradiation and contamination. Many radiation accidents expose a person to both.

Irradiation is exposure to radiation waves that pass directly through the body from outside the body. Irradiation can make a person sick immediately (acute radiation illness). Additionally, irradiation, particularly in high doses, can damage a person's genetic material (DNA), causing chronic (delayed) disorders, such as cancer and birth defects. However, irradiation does not make the person or his tissues radioactive. Contamination is contact with and retention of radioactive material, typically in the form of a dust or liquid. The radioactive material may stay on the skin, where it can fall or be rubbed off, contaminating other people and objects. The material also may be absorbed by the body through the lungs, digestive tract, or breaks in the skin. The absorbed material is transported to various sites in the body, such as the bone marrow, where it continues to release radiation. This internalized radiation does not only cause acute radiation illness, such as internal bleeding, but may produce chronic disorders, such as cancer, as well.

People are constantly exposed to low levels of natural radiation (background radiation). Radiation comes from outer space (cosmic radiation), although much of it is blocked by the earth's atmosphere. Exposure to cosmic radiation is greater for people living or working at high radioactive elements, particularly radon gas, which are also present in many rocks and minerals. These elements end up in a variety of substances, including food and construction materials. In addition, people are exposed to radiation from man-made sources, including the environmental radiation that results from nuclear weapons testing and radiation from various medical tests and treatments. The average person receives a total of about three to four mSv (1 mSv=$\frac{1}{1000}$ Sv) per year from natural radiation and man-made sources. People who work with radioactive materials and with x-ray sources are at risk of exposure to higher levels of radiation. People who are receiving radiation treatments for cancer may receive very high levels of radiation. Nuclear weapons release massive amounts of radiation. These weapons have not been used against people since 1945. However, a number of nations now possess nuclear weapons, and several terrorist groups have also tried to obtain them, raising the possibility that these weapons could once again be used.

The damaging effects of radiation depend on several factors, including the amount (dose) and duration of exposure. A single, rapid dose of radiation to the entire body can be fatal, but the same total dose given over a period of weeks or months may have much less effect. For a given dose, genetic damage is more likely with rapid exposure. The effects of radiation also depend on how much of the body is exposed. For example, more than 6 Gy generally causes death when the radiation is distributed over the entire body; however, when concentrated in a small area, as in radiation therapy for cancer, three or four times this amount can be given without serious harm to the subject as a whole.

The distribution of radiation is also important, because certain parts of the body are more sensitive to radiation. Organs and tissues in which cells are multiplying quickly, such as the intestines and bone marrow, are harmed more easily by radiation than those in which cells multiply more slowly, such as muscles and tendons. The genetic material of sperm and egg cells can be damaged by radiation. During radiation therapy for cancer, therefore, every attempt is made to shield the more vulnerable parts of the body from radiation so that high doses can be delivered primarily to the cancer.

Radiation exposure produces two types of injury: acute (immediate) and chronic (delayed). Acute radiation injury triggers inflammation through vascular endothelial damage leading to leaking vessels. A vascular response and a cellular response follow. Ionizing radiation depresses immunity and damages intestinal epithelium, both of which promote microbial translocation from the intestines.

Radiation therapy for cancer mainly produces symptoms in the part of the body that receives radiation. For example, in radiation therapy for rectal cancer, abdominal cramping and diarrhea are common because of the effects of radiation on the small intestine.

The search for non-toxic radioprotective agents that can protect normal tissue against radiation damage began soon after World War II. Extensive radiobiological research yielded numerous agents which, when given before radiation exposure, protected animals (primarily rodents) against radiation injuries (K. N. Prasad, *Handbook of Radiobiology*, 2nd ed. Boca Raton, Fla.; CRC Press, 1995). From these studies, it became clear that agents, which scavenge free radicals and/or cause hypoxia, may be of radioprotective value. Unfortunately, most of these compounds at radioprotective doses were found to be toxic to humans. With the decreased risk of nuclear confrontation experienced during the evolution of the cold war and later, the interest in the study of radioprotective agents markedly decreased. Due to rapid growth of X-ray-based diagnostic equipments and increased use of radiological procedures in the early diagnosis of disease, concerns are being raised about increased frequency of somatic and heritable mutations that can enhance the risk of gene-linked diseases in present and future generations. Therefore, it has become imperative that normal tissues be protected against potential radiation damage no matter how small that damage might be.

Commonly, radioprotective agents are defined as compounds that are administered before exposure to ionizing radiation to reduce its damaging effects, including radiation-induced lethality (H. B. Stone et al., "Models for evaluating agents intended for the prophylaxis, mitigation and treatment of radiation injuries," Report of an NCI Workshop, Dec. 3-4, 2003, *Radiat. Res.* 162:711-728). They have applications in radiological terrorism, military scenarios, clinical oncology, space travel, radiation site cleanup. R. H. Johnson, "Dealing with the terror of nuclear terrorism," *Health Phys.* 87:S3-7; F. A. J. Mettler, G. L. Voelz, "Major radiation exposure—what to expect and how to respond," *N. Engl. J. Med.* 346:1554-1561 (2001); C. K. Nair, D. K. Parida, T. Nomura, "Radioprotectors in radiotherapy," *J. Radiat. Res.* (Tokyo) 42:21-37; J. K. Waselenko, T. J. MacVittie, W. F. Blakely, N. Pesik, A. L. Wiley, W. E. Dickerson, H. Tsu, D. L. Confer, C. N. Coleman, T. Seed, P. Lowry, J. O. Armitage, N. Dainiak, "Medical management of the acute radiation syndrome: Recommendations of the Strategic National Stockpile Radiation Working Group," *Ann. Intern. Med.* 140:1037-1051. Recently, the U.S. Office of Science and Technology Policy and the Homeland Security Council have made the development of new radioprotectors a top research priority. Although synthetic radioprotectors, such as the aminothiols, have yielded the highest protective factors, typically they are more toxic than naturally occurring protectors. In general, the best radioprotective agents have also been reported to result in the highest behavioral toxicity.

In a military radiation scenario, the effective mitigation of radiation-induced health consequences and performance-degrading effects can reduce the casualty load at medical treatment facilities, sustain a more effective operational force after a radiation exposure event, allow commanders to conduct operations in radiation field environments with reduced risk of decremented performance due to acute tissue injury, and reduce the negative psychological impact on personnel tasked to operate in contaminated environments. The ideal radioprotectant would be nontoxic, would not degrade performance, and would be effective after a single administration, particularly when expedited entry is required into an area with potential external radiation hazards.

In a paper (Landauer et al., NATO RTG-099 2005) presented at the NATO Human Factors and Medicine Panel Research Task Group 099 "Radiation Bioeffects and Countermeasures" meeting, held in Bethesda, Md., USA, Jun. 21-23, 2005, and published in AFRRI CD 05-2, genisteine was forwarded as giving prevention of gamma radiation-induced mortality in mice, having a "Dose reduction Factor" (DRF) at the best dose (200 mg/kg; which resulted in the highest survival rate when administered to mice 24 hours before irradiation) of 1.16. When given at one hour prior to whole body irradiation (WBI), no radioprotection was observed. Other studies describing the radiation protection activity of a drug code-named ON-01210 that were presented at the 51st Radiation Research Society (April, 2004), show that this particular drug ON-01210 (like other drugs that are currently under investigation for radiation exposure) is protective only if it is given pre-radiation exposure. This particular drug has a sulfhydryl component (4-carboxystyrl-4-chlorobenzylsulfone) that works as an antioxidant, scavenging the free radicals that are generated as the radiation damages the cells.

Also, as stated in the annual report to the Congress of the U.S. Department of Defense (March 2005; on the world wide web at medchembio.amedd.army.mil/docs/CBDP_Report_To_Congress.pdf), currently, there are no commercially available non-toxic pharmaceutical agents or diagnostic capabilities suitable for use in military operational environments. An aminothiol compound, amifostine, is FDA approved for use in patients receiving chemotherapy or radiation therapy, but its performance-degrading toxic side effects prohibit its use in a fit fighting force, and its intravenous route of administration requires that medical professionals be available. Other pharmacologic agents, such as hematopoietic cytokines for treating bone marrow injury, may be used off-label on a case-by-case basis by an individual physician, but regulatory restrictions for such use make it impractical for treating large numbers of casualties during military operations. Antibiotics are commonly used to treat the infectious sequelae of radiological injuries, but they must be appropriately selected to effectively treat exogenous and endogenous systemic infections while only little affecting beneficial intestinal anaerobic bacteria.

In addressing the issue of currently limited medical countermeasure alternatives, a novel compound, 5-androstenediol (5-AED; Whitnall et al., *Experimental Biology and Medicine* 226:625-627 (2001)), has been under study at the Armed Forces Radiobiology Research Institute (AFRRI). Again, the compound showed good efficacy as a radioprotectant when administered prior to irradiation challenge in a mouse model. Improvements in survival were observed when AED was administered by sc injection between 24 hours before and 2 hours after gamma-irradiation of mice. A dose reduction factor of 1.3 was calculated from probit survival curves for the administration prior to WBI. Protection was observed in both male and female mice, with and without subsequent inoculation with lethal doses of *Klebsiella pneumoniae*. No protection was observed with a number of other steroids: dehydroepiandrosterone (DHEA), 5-androstene-3B,7B, 17B-triol (AET), androstenedione, or estradiol. However, expanded studies in a nonhuman primate (NHP) model during the past year in preparation for the IND application proved 5-AED is far less effective than in the mouse model when administered as a radioprotectant but yielded good efficacy in the NHP model when administered therapeutically in serial doses shortly following irradiation.

Acute Radiation Illness

Acute radiation illness generally occurs in people whose entire body has been exposed to radiation. Acute radiation illness progresses through several stages, beginning with early symptoms (prodrome) and followed by a symptom-free period (latent stage). Various syndromes (patterns of symptoms) follow, depending on the amount of radiation the person received. The greater the amount of radiation, the more severe the symptoms and the quicker the progression from the early symptoms to the actual syndrome. The symptoms and time course are consistent from person to person for a given amount of radiation exposure. Doctors can predict a person's radiation exposure from the timing and nature of the symptoms. Doctors divide acute radiation syndromes into three groups based on the main organ system affected, although there is overlap among these groups.

The hematopoietic syndrome is caused by the effects of radiation on the bone marrow, spleen, and lymph nodes—the primary sites of blood cell production (hematopoiesis). Loss of appetite (anorexia), lethargy, nausea, and vomiting begin 2 to 12 hours after exposure to 2 Gy or more of radiation. These symptoms resolve within 24 to 36 hours after exposure, and the person feels well for a week or more. During this symptom-free period, the blood-producing cells in the bone marrow, spleen, and lymph nodes begin to waste away and are not replaced, leading to a severe shortage of white blood cells, followed by a shortage of platelets and then red blood cells. The shortage of white blood cells can lead to severe infections. The shortage of platelets may cause uncontrolled bleeding. The shortage of red blood cells (anemia) causes fatigue, weakness, paleness, and difficulty breathing during physical exertion. After four to five weeks, if the person survives, blood cells begin to be produced once more, but the person feels weak and tired for months.

The gastrointestinal syndrome is due to the effects of radiation on the cells lining the digestive tract. Severe nausea, vomiting, and diarrhea begin 2 to 12 hours after exposure to 4 Gy or more of radiation. The symptoms may lead to severe dehydration, but they resolve after two days. During the next four or five days, the person feels well, but the cells lining the digestive tract, which normally act as a protective barrier, die and are shed. After this time, severe diarrhea—often bloody—returns, once more resulting in dehydration. Bacteria from the digestive tract invade the body, producing severe infections. People who have received this much radiation also likely develop the hematopoietic syndrome, which results in bleeding and infection and increases their risk of death.

The cerebrovascular (brain) syndrome occurs when the total dose of radiation exceeds 20 to 30 Gy. A person rapidly develops confusion, nausea, vomiting, bloody diarrhea, and shock. Within hours, blood pressure falls, accompanied by seizures and coma. The cerebrovascular syndrome is considered always fatal.

Chronic Effects of Radiation

Chronic effects of radiation result from damage to the genetic material in dividing cells. These alterations may cause abnormalities of cell growth, such as cancer. In severely irradiated animals, damage to reproductive cells has been shown to lead to defective offspring (birth defects). However, little deformities resulting from irradiation have been observed in the offspring of survivors of the nuclear blasts in Japan. It may be that radiation exposure below a certain (unknown) level does not alter genetic material enough to cause birth defects.

Irradiation injury is suspected when a person becomes ill after receiving radiation therapy or being exposed to radiation in an accident. No specific tests are available to diagnose the condition, although certain tests may be used to detect infection, low blood count, or organ malfunction. To determine the severity of radiation exposure, doctors measure the number of lymphocytes (a type of white blood cell) in the blood. The lower the lymphocyte count 48 hours after exposure, the worse the radiation exposure.

Radioactive contamination, unlike irradiation, can be determined by surveying a person's body with a Geiger counter, a device that detects radiation. Swabs from the nose, throat, and any wounds also are checked for radioactivity.

The outcome of radiation injury depends on the dose, dose rate (how quickly the exposure has occurred), and distribution over the body as well as on the person's underlying state of health. In general, most people who have received more than 6 Gy of WBI die of gastrointestinal syndrome. Because doctors are unlikely to know the exact amount of radiation a person has received, they usually judge outcome by the person's symptoms. The cerebrovascular syndrome is fatal within hours to a few days. The gastrointestinal syndrome generally is fatal within three to ten days, although some people survive for a few weeks. Many people who receive proper medical care survive the hematopoietic syndrome, depending on their total amount of radiation; those who do not survive typically die after 8 to 50 days.

Irradiation has no current emergency treatment, but doctors closely monitor the person for the development of the various syndromes and treat the symptoms as they arise. Also, and unfortunately, very few medical products exist to counter the variety of acute and long-term toxicities that can result from nuclear or radiological attacks. Contamination requires immediate removal of the radioactive material to prevent it from being taken up by the body. Skin contaminated by radioactive materials should be scrubbed immediately with large amounts of soap and water or with a solution designed for this purpose, when available. Small puncture wounds should be cleaned vigorously to remove all radioactive particles, even though scrubbing may cause pain. Contaminated hair is clipped off, not shaved—shaving may abrade the skin and allow contamination to enter the body. Scrubbing continues until the Geiger counter shows that the radioactivity is gone. If a person has recently swallowed radioactive material, vomiting is induced. Some radioactive materials have specific antidotes that can prevent absorption of swallowed material. Most such antidotes are given only to people exposed to significant radioactive contamination, such as from a major reactor accident or nuclear explosion. Potassium iodide prevents the thyroid gland from absorbing radioactive iodine and lowers the risk of thyroid cancer. Other drugs, such as diethylene triamine pentaacetic acid (DTPA), ethylenediamine tetraacetic acid (EDTA), and penicillamine, can be given intravenously to remove certain radioactive elements after they have been absorbed.

When contamination is not suspected, nausea and vomiting can be reduced by taking drugs to prevent vomiting (antiemetics); such drugs are routinely given to people undergoing radiation therapy. Dehydration is treated with fluids given intravenously.

People with the gastrointestinal or hematopoietic syndrome are kept isolated so that they do not contact infectious microorganisms. Blood transfusions and injections of growth factors (such as erythropoietin and colony-stimulating factor) that stimulate blood cell production are given to decrease bleeding and increase blood counts. If the bone marrow is severely damaged, these growth factors are ineffective, and sometimes bone marrow transplantation is performed, although the success rate is low.

People with the gastrointestinal syndrome require antiemetics, fluids given intravenously, and sedatives. Some people may be able to eat a bland diet. Antibiotics, such as neomycin, are given to kill bacteria in the intestine that may invade the body. Antibiotics, as well as antifungal and antiviral drugs, are given intravenously when necessary. Treatment for the cerebrovascular syndrome is geared toward providing comfort by relieving pain, anxiety, and breathing difficulties. Drugs are given to control seizures.

People with chronic effects of radiation or disorders caused by radiation therapy receive treatment directed at their symptoms. Sores or ulcers can be removed or repaired surgically and can be helped to heal with the use of high-pressure (hyperbaric) oxygen therapy. Radiation-induced leukemia is treated with chemotherapy. Blood cells can be replaced through transfusions. No treatment can reverse sterility, but low levels of sex hormones as a result of abnormal ovarian and testicular functioning can be treated with replacement hormones. Investigators are currently exploring ways to prevent or reduce radiation-induced normal tissue injury using cytokines, growth factors, and various other therapies. Amifostine or pilocarpine-HCl have been shown to decrease the severity of dry mouth (xerostomia) in people with head and neck cancer treated with radiation therapy.

Clinical and experimental studies of the acute and late effects of radiation on cells have enhanced our knowledge of radiotherapy and have led to the optimization of radiation treatment schedules and to more precise modes of radiation delivery. However, as both normal and cancerous tissues have similar response to radiation exposure, radiation-induced injury on normal tissues may present either during, or after the completion of, the radiotherapy treatment. Studies on both NSAIDs and prostaglandins have indeed shown some evidence of radioprotection. Both have the potential to increase the survival of cells but by entirely different mechanisms. Studies of cell kinetics reveal that cells in the mitotic (M) and late G2 phases of the cell cycle are generally most sensitive to radiation compared with cells in the early S and G1/G0 phases. Furthermore, radiation leads to a mitotic delay in the cell cycle. Thus, chemical agents that either limit the proportion of cells in the M and G2 phases of the cell cycle or enhance rapid cell growth could, in principle, be exploited for their potential use as radioprotectors to normal tissue during irradiation.

NSAIDs have been shown to exert anti-cancer effects by causing cell-cycle arrest, shifting cells towards a quiescence state (G0/G1). The same mechanism of action was observed in radioprotection of normal tissues. An increase in arachidonic acid concentrations after exposure to NSAIDs also leads to the production of an apoptosis-inducer ceramide. NSAIDs also elevate the level of superoxide dismutase in cells. Activation of heat shock proteins by NSAIDs increases cell survival by alteration of cytokine expression. A role for NSAIDs with respect to inhibition of cellular proliferation possibly by an anti-angiogenesis mechanism has also been suggested. Several in vivo studies have provided evidence suggesting that NSAIDs may protect normal tissues from radiation injury.

Prostaglandins do not regulate the cell cycle, but they do have a variety of effects on cell growth and differentiation. PGE2 mediates angiogenesis, increasing the supply of oxygen and nutrients essential for cellular survival and growth. Accordingly, PGE2 at sufficiently high plasma concentrations may enhance cellular survival by inhibiting pro-inflammatory cytokines such as TNF-α and IL-1β. Thus, PGE2 acts as a modulator, rather than a mediator, of inflammation. Prospective studies have suggested the potential use of misoprostol, a PGE1 analogue, before irradiation, in prevention of radiation-induced side effects. The current understanding of the pharmacology of NSAIDs and prostaglandins shows some potential to minimize the adverse effects of radiation on normal tissue when used preventively.

In addition to transiently inhibiting cell-cycle progression and sterilizing those cells capable of proliferation, irradiation disturbs the homeostasis affected by endogenous mediators of intercellular communication (humoral component of tissue response to radiation). Changes in the mediator levels may modulate radiation effects either by assisting a return to normality (e.g., through a rise in H-type cell lineage-specific growth factors) or by aggravating the damage. The latter mode is illustrated with reports on changes in eicosanoid levels after irradiation and on results of empirical treatment of radiation injuries with anti-inflammatory drugs. Prodromal, acute and chronic effects of radiation are accompanied by excessive production of eicosanoids (prostaglandins, prostacycline, thromboxanes and leukotrienes). These endogenous mediators of inflammatory reactions may be responsible for the vasodilatation, vasoconstriction, increased microvascular permeability, thrombosis and chemotaxis observed after radiation exposure. Glucocorticoids inhibit eicosanoid synthesis primarily by interfering with phospholipase A2 whilst non-steroidal anti-inflammatory drugs prevent prostaglandin/thromboxane synthesis by inhibiting cyclooxygenase. When administered after irradiation on empirical grounds, drugs belonging to both groups tend to attenuate a range of prodromal, acute and chronic effects of radiation in man and animals.

U.S. Pat. No. 5,380,668 to Herron (Jan. 10, 1995), the contents of the entirety of which are incorporated by this reference, discloses, among other things, various compounds having the antigenic binding activity of hCG. The oligopeptides disclosed therein are disclosed generally for use in diagnostic methods. Various patents and patent applications to Gallo et al. (e.g., U.S. Pat. No. 5,677,275 (corresponding to WO 96/04008 A1), U.S. Pat. No. 5,877,148 (also corresponding to WO 96/04008 A1), WO 97/49721 A1, U.S. Pat. No. 6,319,504 (corresponding to WO 97/49373), U.S. Patent Application 2003/0049273 A1 (also corresponding to WO 97/49373), U.S. Pat. No. 5,968,513 (corresponding to WO 97/49418), U.S. Pat. No. 5,997,871 (corresponding to WO 97/49432), U.S. Pat. No. 6,620,416, U.S. Pat. No. 6,596,688, WO 01/11048 A2, WO 01/10907 A2, and U.S. Pat. No. 6,583,109) relate to various oligopeptides and their use in, among other things, "inhibiting HIV infection," "treating or preventing HIV infection," "treating or preventing cancer," "treating or preventing a condition characterized by loss of body cell mass," "treating or preventing a condition associated with pathological angiogenesis," "treating or preventing hematopoietic deficiency," "ex vivo gene therapy," "expanding blood cells in vitro," and/or "providing blood cells to a subject." As described in PCT International Publication No. WO 03/029292 A2 (published Apr. 10, 2003), PCT International Publication No. WO 01/72831 A2 (published Oct. 4, 2001), and U.S. Patent Application Publications 20020064501 A1 (published May 30, 2002), 20030119720 A1 (published Jun. 26, 2003), 20030113733 A1 (published Jun. 19, 2003), and 20030166556 A1 (published Sep. 4, 2003), U.S. patent application Ser. No. 11/249,541, filed on Oct. 13, 2005, International Application No. PCT/EP2005/003707, filed on Apr. 8, 2005, U.S. patent application Ser. No. 10/821,256, filed on Apr. 8, 2004, U.S. patent application Ser. No. 10/262,522, filed on Sep. 30, 2002, International Application No. PCT/NL01/00259 (International Publication No. WO 01/72831 A2) filed Mar. 3, 2001, U.S. Pat. No. 6,844,315 and U.S. Pat. No. 6,921,751, the contents of all of which are incorporated by this reference, compositions containing some of the oligopeptides described herein have immunoregulatory activity useful in, for example, the treatment of sepsis and other disease states and conditions.

The current invention relates to the body's innate way of modulating important physiological processes and builds on insights reported in PCT International Publications WO 99/59617 and WO 01/72831 and PCT International Application PCT/NL02/00639, the contents of the entirety of all of which are incorporated herein by this reference. These applications describe small gene-regulatory peptides that are present in pregnant women and are derived from proteolytic breakdown of placental gonadotropins, such as hCG. These breakdown products are often only about two to six amino acids long and were shown to have unsurpassed immunological activity that is exerted by regulating expression of genes encoding inflammatory mediators such as cytokines. Surprisingly, it was found that breakdown of hCG provides a cascade of peptides that helps maintain a pregnant woman's immunological homeostasis. These peptides balance the immune system to assure that the mother stays immunologically sound while her fetus does not get prematurely rejected during pregnancy, but instead is safely carried until its time of birth.

Furthermore, the current invention relates to U.S. patent application Ser. No. 10/821,240, which provides methods for screening and identifying further small gene-regulatory peptides and using the results from such screens, for example, with peptides derived from a reference peptide. For example, peptides to be analyzed were derived from C-Reactive Protein (CRP) (e.g., human CRP), such peptides include, LTSL (SEQ ID NO:1), FVLS (SEQ ID NO:2), NMWD (SEQ ID NO:3), LCFL (SEQ ID NO:4), MWDF (SEQ ID NO:5), FSYA (SEQ ID NO:6), FWVD (SEQ ID NO:7), AFTV (SEQ ID NO:8), and WDFV (SEQ ID NO:9); peptides derived from Beta-catenin (e.g., human CTNB), such as GLLG (SEQ ID NO:10), TAPS (SEQ ID NO:11), VCQV (SEQ ID NO:12), CLWT (SEQ ID NO:13), VHQL (SEQ ID NO:14), GALH (SEQ ID NO:15), LGTL (SEQ ID NO:16), TLVQ (SEQ ID NO:17), QLLG (SEQ ID NO:18), YAIT (SEQ ID NO:19), LCEL (SEQ ID NO:20), GLIR (SEQ ID NO:21), APSL (SEQ ID NO:22), ITTL (SEQ ID NO:23), QALG (SEQ ID NO:24), HPPS (SEQ ID NO:25), GVLC (SEQ ID NO:26), LCPA (SEQ ID NO:27), LFYA (SEQ ID NO:28), NIMR (SEQ ID NO:29), NLIN (SEQ ID NO:30), LHPP (SEQ ID NO:31), LTEL (SEQ ID NO:32), SPIE (SEQ ID NO:33), VGGI (SEQ ID NO:34), QLLY (SEQ ID NO:35), LNTI (SEQ ID NO:36), LWTL (SEQ ID NO:37), LYSP (SEQ ID NO:38), YAMT (SEQ ID NO:39), LHNL (SEQ ID NO:40), TVLR (SEQ ID NO:41), and LFYA (SEQ ID NO:42); peptides derived from beta-hCG (e.g., human CG), such as GLLLLLLLS (SEQ ID NO:43), MGGTWA (SEQ ID NO:44), TWAS (SEQ ID NO:45), TLAVE (SEQ ID NO:46), RVLQ (SEQ ID NO:47), VCNYRDV (SEQ ID NO:48), FESI (SEQ ID NO:49), RLPG (SEQ ID NO:50), PRGV (SEQ ID NO:51), NPVVS (SEQ ID NO:52), YAVALS (SEQ ID NO:53), LTCDDP (SEQ ID NO:54), EMFQ (SEQ ID NO:55), PVVS (SEQ ID NO:56), VSYA (SEQ ID NO:57), GVLP (SEQ ID NO:58), FQGL (SEQ ID NO:59), and AVAL (SEQ ID NO:60); peptides derived from Bruton's tyrosine kinase (e.g., human BTK), such as LSNI (SEQ ID NO:61), YVFS (SEQ ID NO:62), LYGV (SEQ ID NO:63), YVVC (SEQ ID NO:64), FIVR (SEQ ID NO:65), NILD (SEQ ID NO:66), TIMY (SEQ ID NO:67), LESI (SEQ ID NO:68), FLLT (SEQ ID NO:69), VFSP (SEQ ID NO:70), FILE (SEQ ID NO:71), TFLK (SEQ ID NO:72), FWID (SEQ ID NO:73), MWEI (SEQ ID NO:74), QLLE (SEQ ID NO:75), PCFW (SEQ ID NO:76), VHKL (SEQ ID NO:77), LYGV (SEQ ID NO:63), LESI (SEQ ID NO:68), LSNI (SEQ ID NO:61), YVFS (SEQ ID NO:78), IYSL (SEQ ID NO:79), and NILD (SEQ ID NO:66); and peptides derived from matrix metalloproteinase-2 (e.g., human MM02), such as FKGA (SEQ ID NO:80), FFGL (SEQ ID NO:81), GIAQ (SEQ ID NO:82), LGCL (SEQ ID NO:83), YWIY (SEQ ID NO:84), AWNA (SEQ ID NO:85), ARGA (SEQ ID NO:86), PFRF (SEQ ID NO:87), APSP (SEQ ID NO:88), CLLS (SEQ ID NO:89), GLPQ (SEQ ID NO:90), TFWP (SEQ ID NO:91), AYYL (SEQ ID NO:92), FWPE (SEQ ID NO:93), CLLG (SEQ ID NO:94), FLWC (SEQ ID NO:95), RIIG (SEQ ID NO:96), WSDV (SEQ ID NO:97), PIIK (SEQ ID NO:98), GLPP (SEQ ID NO:99), RALC (SEQ ID NO:100), LNTF (SEQ ID NO:101), LSHA (SEQ ID NO:102), ATFW (SEQ ID NO:103), PSPI (SEQ ID NO:104), AHEF (SEQ ID NO:105), WRTV (SEQ ID NO:106), FVLK (SEQ ID NO:107), VQYL (SEQ ID NO:108), KFFG (SEQ ID NO:109), FPFR (SEQ ID NO:110), IYSA (SEQ ID NO:111), and FDGI (SEQ ID NO:112), and others.

DISCLOSURE OF THE INVENTION

The invention relates to the field of developing drugs against acute radiation injury caused by exposure to high-energy electromagnetic waves (x-rays/photons and/or natural gamma rays) and/or other high energy ionizing particles (alpha particles, beta particles, neutrons, protons, pi-mesons). To date, there is no effective drug to ameliorate radiation injury after accidental exposure to ionizing irradiation, or after damage to healthy tissues during therapeutic radiation or radio-mimetic agents; nor is there an effective prophylactic drug to prevent or minimize such injuries when administered before the event (for example, to first responders).

The present inventors surprisingly observed that relatively small, non-toxic peptides can be effective as drugs against radiation damage. Importantly, the anti-radiation peptides of the invention are not only useful as prophylactic agents but can also protect when administered several hours after exposure to radiation. This makes them extremely suitable for use in a military radiation scenario, e.g., when dealing with the terror of nuclear terrorism. Accordingly, the invention provides a method of preventing or treating radiation injury of a subject in need thereof comprising administering to the subject a peptide, or functional analogue thereof, of smaller than 30 amino acids. Preferably, the peptide or functional analogue thereof is administered to the subject post-radiation, i.e., following exposure of the subject to a source of radiation.

Furthermore, the invention provides use of a peptide, or functional analogue thereof, of smaller than 30 amino acids for the production of a pharmaceutical composition for the treatment of a subject suffering from or believed to be suffering from radiation injury. In particular, the invention provides anti-radiation peptides having a dose reduction factor (DRF) against acute whole body irradiation of at least 1.10, the DRF determinable by testing which dose of whole body irradiation (WBI) results in 50% mortality at 30 days (LD50/30) in a test group of experimental rodents (e.g., mice) treated with the peptide immediately or up to 72 hours after WBI, versus the dose of WBI that results in 50% mortality at 30 days (LD50/30) in an untreated control group, and wherein the DRF is calculated by dividing the LD50/30 radiation dose of the peptide-treated animals by the LD50/30 radiation dose of the vehicle-treated animals.

The invention provides a method for treating a subject suffering from or believed to be suffering from radiation injury, the method comprising providing the subject with a pharmaceutical composition comprising an anti-radiation peptide of smaller than 30 amino acids. Current radioprotection agents are of a non-peptide nature or comprise large proteins, such as cytokines. The present invention discloses that peptides, such as MTRVLQGVLPALPQVVC (SEQ ID NO:113), that are smaller than 30 amino acids are useful for protection against and treatment of radiation injury. For the first time, it is shown that a peptide drug is capable of reducing damaging effects of radiation when it is administered after exposure to radiation has taken place. For example, the anti-radiation peptide consists of up to 29, up to 28, up to 27, up to 26, up to 25, up to 24, up to 23, up to 22, up to 21, up to 20, up to 19, up to 18, up to 17, up to 16 or up to 15 amino acids.

It is, however, preferred that the peptide is smaller than 15 amino acids. For example, the anti-radiation peptide preferably consists of up to 14, up to 13, up to 12, up to 11, up to 10, up to 9 or up to 8 amino acids. Some examples of useful peptides are LPGCPRGVNPVVS (SEQ ID NO:114), DING-FLPAL (SEQ ID NO:115) and QPLAPLVG (SEQ ID NO:116). However, when peptides are used for self-medication, for example, as is provided herein with an autoinjector, from a safety viewpoint, it is preferred that the peptide is smaller than seven amino acids. Such a peptide will generally not bind to the MHC receptors, thereby decreasing the risk of the development of autoimmunity initiated by an immune response against administered peptide.

This size of smaller than seven amino acids (aa) is also particularly preferred because it was determined (when comparing peptides derived from the human proteome with those derived from pathogen proteomes, in particular, of viruses or bacteria (Burroughs et al., *Immunogenetics*, 2004, 56:311-320)) that with a peptide size of seven amino acids, only 3% overlap between self or non-self is found. For peptides of six amino acids, that overlap in human self with pathogen non-self was determined to be 30%; for peptides of five amino acids, 90%; and for four amino acids long (and smaller) peptides, 100% overlap between the peptides present in the human proteome and the peptides present in the proteome of pathogens was determined. Based on these data, it is now herein recognized that when the self-non-self difference is not present, risk of adverse immune reactions, such as anaphylactic shock, is greatly diminished, which is a distinct advantage when non-medically trained persons administer any drug to themselves or to others.

From the viewpoint of preventing adverse reactions, such as anaphylactic shock, it is thus preferred that the peptide consists of two to six amino acids, more preferably consists of three to five amino acids, and most preferably consists of three or four amino acids. From the viewpoint of activity, based on a general insight that activity is broader with increasing peptide size, if only to withstand full proteolysis longer whereby metabolic fragments of three amino acids still have activity, it is herein preferred that the peptide consists of four amino acids. The above- and below-described compositions are preferably used for the treatment of acute radiation injury.

The use of peptides to protect against radiation injury has been proposed in the art. Japanese patent applications JP09157291 and JP09157292 describe specific 6-mer and 9-mer peptide sequences having an in vitro-inhibiting effect on activated oxygen, scavenging actions of activated oxygen free radicals and antioxidizing activity. It is speculated that the peptides are useful in vivo to suppress the adverse effects of various types of events known to be associated with active oxygen formation, including radiation damage. No in vivo radiation experiments were conducted.

JP09176187 teaches a histidine-containing 6-mer peptide analog having active oxygen-scavenging activity. Peritoneal administration of a peptide at 660 mg/kg of body weight 20 minutes prior to irradiation increased the survival rate of mice from 10% in the control group to 70% in the treated group. No in vivo post-radiation experiments were conducted.

WO2006/032269 describes a homogenate of blood cells from which components having a molecular weight of more than 3 kDa have been removed. The homogenate is reported to be suitable for improving the cellular immune response in a subject. Among a long list of diverse immunological diseases and pathological conditions, it is proposed that the homogenate can be administered to a patient in a prophylactic fashion in a treatment using chemotherapeutical agents and/or radiation in order to optimize the patient's general condition. It is noted that the study does not involve any radiation experiments. Furthermore, although the homogenate likely comprises among others a mixture of proteins, the identity of the active component(s) is not clear at all and they may well be of non-proteinaceous nature. At any rate, no distinct peptides have been isolated or identified therein.

EP 0572688 discloses a specific peptide comprising 14 amino acid residues that at 20 mg/kg body weight was found to confer protection in mice against whole body radiation. The effect was only observed when the compound was applied one hour before radiation. However, no difference relative to control data was observed when peptide was administered one hour after exposure to irradiation.

These prior art disclosures are in marked contrast to the present invention; the anti-radiation peptides as disclosed herein can provide protection even if administered several hours after whole body irradiation.

Subjects having received sub-lethal radiation doses will already benefit from the anti-inflammatory properties of some of the small peptides identified herein, but surprisingly, most benefit will come from the anti-gastrointestinal syndrome activity of the small peptides, notably of the 3- and 4-mer peptides at dosages above 1 mg/kg, preferably above 5 mg/kg, and more preferably above 10 mg/kg bodyweight. Considering the low immunogenic nature of the small peptides (i.e., those of three to four amino acids), dosing to up to 100 mg/kg with small peptides, and in some cases when need for treatment is determined to be acute considering the condition of the subject in need of treatment, of up to 200 mg/kg, 500 mg/kg or even 1 g/kg will be possible. Consequently, the treatment of subjects who have radiation injury that comprises damage of the lining of the intestinal tract of the subject, the so-called gastrointestinal syndrome, has now been made possible; the peptides allowing the epithelial lining to slowly recover.

For a better activity of peptides under high radiation dosage, it is preferred to select a peptide for inclusion in a pharmaceutical composition of the invention or for inclusion in an autoinjector according to the invention that has a dose reduction factor (DRF) against acute gamma irradiation of at least 1.10, the DRF determinable by testing which dose of radiation results in 50% mortality at 30 days (LD50/30) after whole body radiation (WBI) in a test group of mice treated with the peptide at 72 hours after WBI and, testing which dose of radiation results in 50% mortality at 30 days (LD50/30) after whole body radiation (WBI) in a control group of mice treated only with the vehicle of the peptide at 72 hours after WBI and, wherein the DRF is calculated by dividing the LD50/30 of the peptide-treated animals by the LD50/30 of the vehicle-treated animals.

It is even more preferred to use a peptide having a dose reduction factor (DRF) of at least 1.20, more preferably of at least 1.25, especially when the radiation injury is irradiation injury. Such peptides as identified herein are also called anti-radiation peptides. The invention provides a method and pharmaceutical composition for the treatment of irradiation injury irrespective of whether the radiation is emitted by radioactive substances (radioisotopes), such as uranium, radon, and plutonium, or is produced by man-made sources, such as x-ray and radiation therapy machines.

The invention also provides use of a peptide of smaller than 30 amino acids for the production of a pharmaceutical composition for the treatment a subject suffering from, or believed to be suffering from, radiation injury. As above, it is preferred that the peptide be smaller than 15 amino acids, and, for self-medication or for administration by laymen, it is even more preferred that the peptide be smaller than seven amino acids. Several useful 3-mer peptides for use in the production of a pharmaceutical composition for treatment of radiation injury are identified herein as VVC, LAG, and AQG.

Similarly, several useful 4-mer peptides for treatment of radiation injury are LQGV (SEQ ID NO:117), QVVC (SEQ ID NO:118), MTRV (SEQ ID NO:119), AQGV (SEQ ID NO:120), LAGV (SEQ ID NO:121), LQAV (SEQ ID NO:122), PGCP (SEQ ID NO:123), VGQL (SEQ ID NO:124), RVLQ (SEQ ID NO:125), EMFQ (SEQ ID NO:126), AVAL (SEQ ID NO:127), FVLS (SEQ ID NO:2), NMWD (SEQ ID NO:3), LCFL (SEQ ID NO:4), FSYA (SEQ ID NO:6), FWVD (SEQ ID NO:7), AFTV (SEQ ID NO:8), LGTL (SEQ ID NO:16), QLLG (SEQ ID NO:18), YAIT (SEQ ID NO:19), APSL (SEQ ID NO:22), ITTL (SEQ ID NO:23), QALG (SEQ ID NO:24), GVLC (SEQ ID NO:26), NLIN (SEQ ID NO:30), SPIE (SEQ ID NO:33), LNTI (SEQ ID NO:36), LHNL (SEQ ID NO:40), CPVQ (SEQ ID NO:128), EVVR (SEQ ID NO:129), MTEV (SEQ ID NO:130), EALE (SEQ ID NO:131), EPPE (SEQ ID NO:132), LGTL (SEQ ID NO:133), VGGI (SEQ ID NO:134), RLPG (SEQ ID NO:135), LQGA (SEQ ID NO:136), and LCFL (SEQ ID NO:137); useful 5-mer peptides for treatment of radiation injury are TLAVE (SEQ ID NO:46), VEGNL (SEQ ID NO:138), and LNEAL (SEQ ID NO:139); useful 6-mer peptides for treatment of radiation injury are VLPALP (SEQ ID NO:140), MGGTWA (SEQ ID NO:44); LTCDDP (SEQ ID NO:54); useful 7-mer peptides for treatment of radiation injury are VLPAPLQ (SEQ ID NO:141), VCNYRDV (SEQ ID NO:48), and CPRGVNP (SEQ ID NO:142); a useful 8-mer peptide for treatment of radiation injury is QPLAPLVG (SEQ ID NO: 116); and a useful 9-mer peptide for treatment of radiation injury is DINGFLPAL (SEQ ID NO:115).

Other peptides, especially 3- or 4-mer peptides, can be found by testing for anti-cell-cycle activity in proliferation assays, for example, by using the plant growth assay as provided herein. Use of a peptide for the production of a pharmaceutical composition for the treatment of a subject suffering from, or believed to be suffering from, radiation injury wherein the peptide consists of two to six amino acids is herein particularly provided. Again, from the viewpoint of preventing adverse reactions such as anaphylactic shock, it is thus preferred that the pharmaceutical composition is made with a peptide that consists of two to six amino acids, more preferably consists of three to five amino acids, and most preferably consists of three or four amino acids. If only from the viewpoint of activity, based on a general insight that activity is broader with increasing peptide size, if only to withstand full proteolysis (after administration) longer whereby metabolic fragments of three amino acids still have activity, it is herein preferred that the peptide consists of four amino acids.

Furthermore, it is particularly useful that subjects in need of treatment for radiation injury can now be treated via a mere subcutaneous or intramuscular injection, thereby allowing self-treatment with an autoinjector or treatment by non-trained or non-medical personnel, thereby greatly facilitating the organization of help in emergency scenarios where thousands of people may need to be treated. If only intravenous or similarly risky intraperitoneal injections had been found to be useful, subjects in need of treatment would be harder to help, when compared now to the situation that simple administration tools such as autoinjectors are provided herein.

In particular, the invention also provides use of a peptide smaller than 30 amino acids for the production of a pharmaceutical composition for the treatment of radiation injury, wherein the pharmaceutical composition is contained in an autoinjector. An autoinjector is a medical device designed to deliver a single dose of a particular (typically life-saving) drug, sometimes also described as a pre-filled syringe for self-injection or injection by non-medical personnel or laymen. As used herein, the term "autoinjector" does not refer to an injector for the automated application of a biological (e.g., peptide) sample in an analytical system, such as a chromatography apparatus, as is described, for example, in Husek et al. (*J. of Chromatography B: Biomedical Sciences & Applications*, Elsevier, Amsterda, Vol. 767, no. 1 (2002), pg. 169-174).

By design, autoinjectors are easy to use and are intended for self-administration by patients or administration by laymen to patients. The site of injection typically is into the thigh or the buttocks, wherein the treatment comprises subcutaneous or intramuscular injection with the peptide. Because autoinjectors may be designed to automatically and reliably deliver a desired dose of medicament, they facilitate quick, convenient, and accurate delivery of medicaments. In particular, autoinjectors are well suited for use by subjects who must self-administer therapeutic substances or by healthcare workers who must inject multiple subjects over a relatively short period of time, for instance, in an emergency situation. Moreover, autoinjectors incorporating a needled injection mechanism may be designed so that the needle is hidden from view before, during, and even after an injection operation, thereby reducing or eliminating any anxiety associated with the act of penetrating a visible needle into the subject's tissue. Though their precise specifications vary widely, needled autoinjectors generally include a body or housing, a needled syringe or similar device, and one or more drive mechanisms for inserting a needle into the tissue of the subject and delivering a desired dose of liquid medicament through the inserted needle. The drive mechanisms included in state of the art needled autoinjectors generally include a source of energy capable of powering the drive mechanism. This energy source may be, for example, mechanical (i.e., spring-loaded), pneumatic, electromechanical, or chemical, as described in U.S. Pat. Nos. 6,149,626, 6,099,504, 5,957,897, 5,695,472, 5,665,071, 5,567,160, 5,527,287, 5,354,286, 5,300,030, 5,102,393, 5,092,843, 4,894,054, 4,678,461, and 3,797,489, the contents of each such patent being incorporated herein by reference. International Publications numbered WO 01/17593, WO 98/00188, WO 95/29720, WO 95/31235, and WO 94/13342 also describe various injectors including different drive mechanisms. Most autoinjectors are (optionally spring-loaded) syringes. An autoinjector of the present invention, in particular, the body or housing thereof that is in direct contact with the peptide, is preferably made of a material that has a minimal affinity for peptides. This can reduce unwanted adhesion or sticking of peptides to the autoinjector to a minimum. A very suitable material is polypropylene, in particular, essentially pure polypropylene.

Autoinjectors were initially designed to overcome the hesitation associated with self-administration of needle-based drugs. Examples of such autoinjectors are Epipen® or the recently introduced Twinject®, which is often prescribed to persons who are at risk for anaphylaxis. Another example of an autoinjector is the Rebiject® for interferon beta used to treat Multiple Sclerosis. Autoinjectors are often used in the military to protect personnel from chemical warfare agents. In the United States Military, an autoinjector is part of every Biological or Chemical Weapons Response kit. It is issued to every soldier in the event they may face Biological or Chemical Weapons. The needle automatically injects the person once you activate it, piercing any clothes (even multiple layers) one may be wearing. An autoinjector herein not only comprises the above-described injection devices that usually are spring-driven, whereby the skin penetration and/or the injection of the drug takes place automatically, but also comprises pre-filled syringes, or autoinjector cartridges and the like.

The invention provides such an autoinjector useful for the treatment of (ir)radiation injury irrespective of whether the radiation is emitted by radioactive substances (radioisotopes), such as uranium, radon, and plutonium, or is produced by man-made sources, such as x-ray and radiation therapy machines. The invention also provides an autoinjector comprising a pharmaceutical composition consisting of a peptide of smaller than 30 amino acids (herein also called anti-radiation peptide) and a suitable excipient. Suitable excipients are known in the art. See, for example, *The Handbook of Pharmaceutical Manufacturing Formulations* (edited by Sarfaraz K. Niazi; ISBN:0849317460) and incorporated herein by reference.

Suitable excipients, for example, are composed of water, propylene glycol, ethyl alcohol, sodium benzoate and benzoic acid as buffers, and benzyl alcohol as preservative; or of mannitol, human serum albumin, sodium acetate, acetic acid, sodium hydroxide, and water for injections. Other exemplary compositions for parenteral administration via an autoinjector include injectable solutions or suspensions that may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

In one embodiment, an autoinjector comprises as an active ingredient an anti-radiation peptide (or functional analog thereof) that is capable of reducing adverse effects of radiation in a subject when administered after the subject has been exposed to radiation. Preferably, the peptide can confer at least a partial protection against radiation damage if administered at least 30 minutes, more preferably at least one hour, most preferably at least several hours or even several days (e.g., three days) post-irradiation. This type of autoinjector is also referred to as an "emergency-autoinjector," reflecting its applicability in unexpected emergency situations.

In one embodiment, the invention provides an autoinjector containing a sterile solution packaged within a syringe-like device that delivers its entire 5 mL contents automatically upon activation. Each mL contains 100 mg, preferably 200 mg, anti-radiation peptide compounded with an excipient, such as an excipient comprising propylene glycol, ethyl alcohol, sodium benzoate and benzoic acid as buffers, and benzyl alcohol as preservative. In a preferred embodiment, the autoinjector for the treatment of radiation injury carries an anti-radiation peptide smaller than 15 amino acids, more preferably smaller than seven amino acids.

Preferred are autoinjectors for the treatment of acute radiation injury carrying a peptide of three to four amino acids in length, preferably a peptide that has a dose reduction factor (DRF) against acute gamma irradiation of at least 1.10, the DRF determinable by testing which dose of radiation results in 50% mortality at 30 days (LD50/30) after whole body radiation (WBI) in a test group of mice treated with the peptide at 72 hours after WBI and, testing which dose of radiation results in 50% mortality at 30 days (LD50/30) after whole body radiation (WBI) in a control group of mice treated only with the vehicle of the peptide at 72 hours after WBI and, wherein the DRF is calculated by dividing the LD50/30 of the peptide-treated animals by the LD50/30 of the control animals.

Even more preferred is an autoinjector carrying a peptide that has a dose reduction factor (DRF) of at least 1.20, more preferably of at least 1.25. Suitable peptides for inclusion in an autoinjector are also those that have anti cell-cycle activity in plants, as determined herein. Very suitable peptides for use in an autoinjector of the invention are VVC, LAG, AQG, LQGV (SEQ ID NO:117), QVVC (SEQ ID NO:118), MTRV (SEQ ID NO:119), AQGV (SEQ ID NO:120), LAGV (SEQ ID NO:121), LQAV (SEQ ID NO:122), PGCP (SEQ ID NO:123), VGQL (SEQ ID NO:124), RVLQ (SEQ ID NO:125), EMFQ (SEQ ID NO:126), AVAL (SEQ ID NO:127), FVLS (SEQ ID NO:2), NMWD (SEQ ID NO:3), LCFL (SEQ ID NO:4), FSYA (SEQ ID NO:6), FWVD (SEQ ID NO:7), AFTV (SEQ ID NO:8), LGTL (SEQ ID NO:16), QLLG (SEQ ID NO:18), YAIT (SEQ ID NO:19), APSL (SEQ ID NO:22), ITTL (SEQ ID NO:23), QALG (SEQ ID NO:24), GVLC (SEQ ID NO:26), NLIN (SEQ ID NO:30), SPIE (SEQ ID NO:33), LNTI (SEQ ID NO:36), LHNL (SEQ ID NO:40), CPVQ (SEQ ID NO:128), EVVR (SEQ ID NO:129), MTEV (SEQ ID NO:130), EALE (SEQ ID NO:131), EPPE (SEQ ID NO:132), LGTL (SEQ ID NO:133), VGGI (SEQ ID NO:134), RLPG (SEQ ID NO:135), LQGA (SEQ ID NO:136), LCFL (SEQ ID NO:137), TLAVE (SEQ ID NO:46), VEGNL (SEQ ID NO:138), or LNEAL (SEQ ID NO:139).

The invention also provides a pharmaceutical composition for the treatment of a subject suffering from, or believed to be suffering from, radiation injury, the pharmaceutical composition comprising: a pharmacologically effective amount of anti-radiation peptide, or a functional analogue thereof, or pharmaceutical composition as identified herein, together with a pharmaceutically acceptable diluent. The invention herewith provides a method of treating or preventing radiation injury in a subject in need thereof or in potential need thereof, the method comprising: administering to the subject a pharmaceutical composition comprising: means for treating or preventing radiation injury, and a pharmaceutically acceptable excipient, wherein the means comprise an anti-radiation peptide or pharmaceutical composition as identified herein, in particular wherein the radiation injury comprises irradiation injury.

In one embodiment, the invention provides a method of treating radiation injury of a subject in need thereof comprising administering to the subject a composition comprising an oligopeptide obtainable or derivable from the peptide MTRVLQGVLPALPQVVC (SEQ ID NO:113) or from the peptide LPGCPRGVNPVVS (SEQ ID NO:114). It is preferred that the oligopeptide is selected from the group consisting of MTR, MTRV (SEQ ID NO:119), LQG, LQGV (SEQ ID NO:117), VLPALP (SEQ ID NO:140), VLPALPQ (SEQ ID NO:143), QVVC (SEQ ID NO:118), VVC, AQG, AQGV (SEQ ID NO:120), LAG, LAGV (SEQ ID NO:121), and any combination thereof.

In another embodiment, it is preferred that the oligopeptide is selected from the group consisting of LPGC (SEQ ID NO:144), CPRGVNP (SEQ ID NO:142) and PGCP (SEQ ID NO:123). Such oligopeptides are particularly useful when the radiation injury comprises irradiation injury.

The invention also provides a pharmaceutical composition for the treatment of radiation injury comprising an oligopeptide obtainable or derivable from the peptide MTRVLQGVLPALPQVVC (SEQ ID NO:113) or from the peptide LPGCPRGVNPVVS (SEQ ID NO:114), such as an oligopeptide selected from the group of MTR, MTRV (SEQ ID NO:119), LQG, LQGV (SEQ ID NO:117), VLPALP (SEQ ID NO:140), VLPALPQ (SEQ ID NO:143), QVVC (SEQ ID NO:118), VVC, AQG, AQGV (SEQ ID NO:120), LAG, LAGV (SEQ ID NO:121), LPGC (SEQ ID NO:144), CPRGVNP (SEQ ID NO:142) and PGCP (SEQ ID NO:123), and combinations of any thereof and use of such oligopeptide(s) for the production of a pharmaceutical composition for the treatment of radiation injury.

Earlier, we reported inhibition of septic shock in mice by a 6-mer oligopeptide (VLPALP (SEQ ID NO:140)) derived from the beta-chain of human chorionic gonadotropin hormone. Also, we showed that several other short (from trimeric peptides up) peptides derived from loop 2 of the beta chain of hCG (residues 41-57), and modifications of some of the peptides obtained by alanine substitution of single amino acids, have similar anti-inflammatory activity. Furthermore, we provide our rationale for selecting several of these for continuing development towards a therapeutic compound for treatment of acute inflammatory conditions after accidental exposure to ionizing irradiation.

Human chorionic gonadotropin (hCG) is a heterodimeric placental glycoprotein hormone required in pregnancy. In human pregnancy urine and in commercial hCG preparations, it occurs in a variety of forms, including breakdown products. Several investigators have studied the effects of heterodimeric hCG and its variants on the immune system because of their putative role in preventing the rejection of the fetal allograft during pregnancy. Several reports have suggested modulation of the immune system by intact hormone, but such effects of breakdown products have not been reported. Earlier, we (Khan et al., Hum. Immunol. January 2002, 63(1):1-7), reported inhibition of septic shock in mice by a 6-mer oligopeptide (VLPALP (SEQ ID NO:140)) derived from the beta-chain of human chorionic gonadotropin hormone. A single treatment with this hexapeptide after high dose lipopolysaccharide (LPS) injection inhibited septic shock in mice. Benner and Khan (Scand. J. Immunol. July 2005, 62 Suppl 1:62-6) studied the possible immunological activity of the in vivo-liberated peptide fragments originating from nicking of the sequence MTRVLQGVLPALPQVVC (SEQ ID NO:113) (residues 41-57) of loop 2 of the beta-subunit of hCG. Here, it is reported that several of the three to seven amino acid-long peptides taken from loop 2 of the beta-subunit—and alanine-replacement peptides derived of some—displayed significant anti-inflammatory activity as measured by the inhibition of septic shock syndrome in mice and are beyond that considered useful for treatment of radiation injury, in particular, of radiation injury comprising gastrointestinal syndrome and for the production of a pharmaceutical composition for the treatment of radiation injury, in particular, of radiation injury comprising gastrointestinal syndrome.

The invention also provides a pharmaceutical composition having anti-cell-cycle activity. The cell cycle is an ordered set of events, culminating in cell growth and division into two daughter cells. The stages of the cell cycle are G1-S-G2-M. The G1 stage stands for "GAP 1." The S stage stands for "Synthesis." This is the stage when DNA replication occurs. The G2 stage stands for "GAP 2." The M stage stands for "mitosis," and is when nuclear (chromosomes separate) and cytoplasmic (cytokinesis) division occur. The term "anti-cell-cycle activity," as used herein, is meant to indicate that the peptide is capable of altering cell-cycle dynamics. For example, it comprises altering, i.e., increasing or reducing, the frequency of cell division. In one embodiment, it refers to an anti-proliferative activity.

Provided is a pharmaceutical composition having anti-cell-cycle activity comprising PGCP (SEQ ID NO:123), a pharmaceutical composition having anti-cell-cycle activity comprising VGQL (SEQ ID NO:124), a pharmaceutical composition having anti-cell-cycle activity comprising RVLQ (SEQ ID NO:125), a pharmaceutical composition having anti-cell-cycle activity comprising EMFQ (SEQ ID NO:126), a pharmaceutical composition having anti-cell-cycle activity comprising AVAL (SEQ ID NO:127), a pharmaceutical composition having anti-cell-cycle activity comprising FVLS (SEQ ID NO:2), a pharmaceutical composition having anti-cell-cycle activity comprising NMWD (SEQ ID NO:3), a pharmaceutical composition having anti-cell-cycle activity comprising LCFL (SEQ ID NO:4), a pharmaceutical composition having anti-cell-cycle activity comprising FSYA (SEQ ID NO:6), a pharmaceutical composition having anti-cell-cycle activity comprising FWVD (SEQ ID NO:7), a pharmaceutical composition having anti-cell-cycle activity comprising AFTV (SEQ ID NO:8), a pharmaceutical composition having anti-cell-cycle activity comprising LGTL (SEQ ID NO:16), a pharmaceutical composition having anti-cell-cycle activity comprising QLLG (SEQ ID NO:18), a pharmaceutical composition having anti-cell-cycle activity comprising YAIT (SEQ ID NO:19), a pharmaceutical composition having anti-cell-cycle activity comprising APSL (SEQ ID NO:22), a pharmaceutical composition having anti-cell-cycle activity comprising ITTL (SEQ ID NO:23), a pharmaceutical composition having anti-cell-cycle activity comprising QALG (SEQ ID NO:24), a pharmaceutical composition having anti-cell-cycle activity comprising GVLC (SEQ ID NO:26), a pharmaceutical composition having anti-cell-cycle activity comprising NLIN (SEQ ID NO:30), a pharmaceutical composition having anti-cell-cycle activity comprising SPIE (SEQ ID NO:33), a pharmaceutical composition having anti-cell-cycle activity comprising LNTI (SEQ ID NO:36), a pharmaceutical composition having anti-cell-cycle activity comprising LHNL (SEQ ID NO:40), a pharmaceutical composition having anti-cell-cycle activity comprising CPVQ (SEQ ID NO:128), a pharmaceutical composition having anti-cell-cycle activity comprising EVVR (SEQ ID NO:129), a pharmaceutical composition having anti-cell-cycle activity comprising MTEV (SEQ ID NO:130), a pharmaceutical composition having anti-cell-cycle activity comprising EALE (SEQ ID NO:131), a pharmaceutical composition having anti-cell-cycle activity comprising EPPE (SEQ ID NO:132), a pharmaceutical composition having anti-cell-cycle activity comprising LGTL (SEQ ID NO:133), a pharmaceutical composition having anti-cell-cycle activity comprising VGGI (SEQ ID NO:134), a pharmaceutical composition having anti-cell-cycle activity comprising RLPG (SEQ ID NO:135), a pharmaceutical composition having anti-cell-cycle activity comprising LQGA (SEQ ID NO:136), a pharmaceutical composition having anti-cell-cycle activity comprising LCFL (SEQ ID NO:137), a pharmaceutical composition having anti-cell-cycle activity comprising TLAVE (SEQ ID NO:46), a pharmaceutical composition having anti-cell-cycle activity comprising VEGNL (SEQ ID NO:138), a pharmaceutical composition having anti-cell-cycle activity comprising LNEAL (SEQ ID NO:139), a pharmaceutical composition having anti-cell-cycle activity comprising MGGTWA (SEQ ID NO:44), a pharmaceutical composition having anti-cell-cycle activity comprising LTCDDP (SEQ ID NO:54), a pharmaceutical composition having anti-cell-cycle activity comprising VCNYRDV (SEQ ID NO:48), a pharmaceutical composition having anti-cell-cycle activity comprising CPRGVNP (SEQ ID NO:142), and a pharmaceutical composition having anti-cell-cycle activity comprising DINGFLPAL (SEQ ID NO:115).

"WBI" stands for Whole Body Irradiation. Radiation damage protection in vivo was assessed after WBI (6.5 to 9.8 Gy, Philips MG 30 at 81 cGy/min) on anesthetized C57B1/6 mice, and survival differences were measured by Kaplan-Meirer analysis. All groups of mice got the first injection with peptide or vehicle (control animals) three hours after the WBI. The group that got a placebo injection experienced 80% mortality, as predicted in this model. The dose of radiation of 8.6 Gray (=8.6 Gy) is known, in this species, to cause about an 80% mortality, so it is called the LD80 (lethal dose for 80%). The deaths started around Day 10, which is typical for what happens in WBI to animals or humans. By around Day 10, the gut lining is so damaged and leaky from the radiation that bacteria get into the circulation and cause gastrointestinal syndrome, and the bone marrow is so damaged that there is an insufficient number of white blood cells to fight the infection ("Bone Marrow Syndrome"), and death ensues. The group with "x" as the symbol got the first injection IV, and the second injection subcutaneously (SC) three hours after that first injection. 100% of these animals survived. What the graph does not show is that they did not show any signs of sickness at all. To an outside observer, they would look like perfectly normal mice. The group with the triangle symbol got its first injection of the peptide via the SC route. Then it got additional SC injections every 48 hours, for a total of three doses (in addition to the first dose), meaning, on Day 3, Day 5, and Day 7. Note that only one of these animals died. The group with the square symbol was identical in procedures to the group with the triangle symbol, except that the 48 hour SC injections continued on until a total of six doses had been injected (in addition to the first dose). So the dosing continued on until Day 13. Note that this prolonging of the treatment was associated with complete protection (no mortality whatsoever in this group). The animals in this group showed no signs of sickness. What we can conclude from this data is that when the animals got two doses of peptide in the first day (with the first one being IV), there was complete protection against a highly-lethal dose of WBI. When the animals got lower-level treatment (SC only), if the treatment was prolonged until the second week, here again, there was complete protection.

Figure 2:
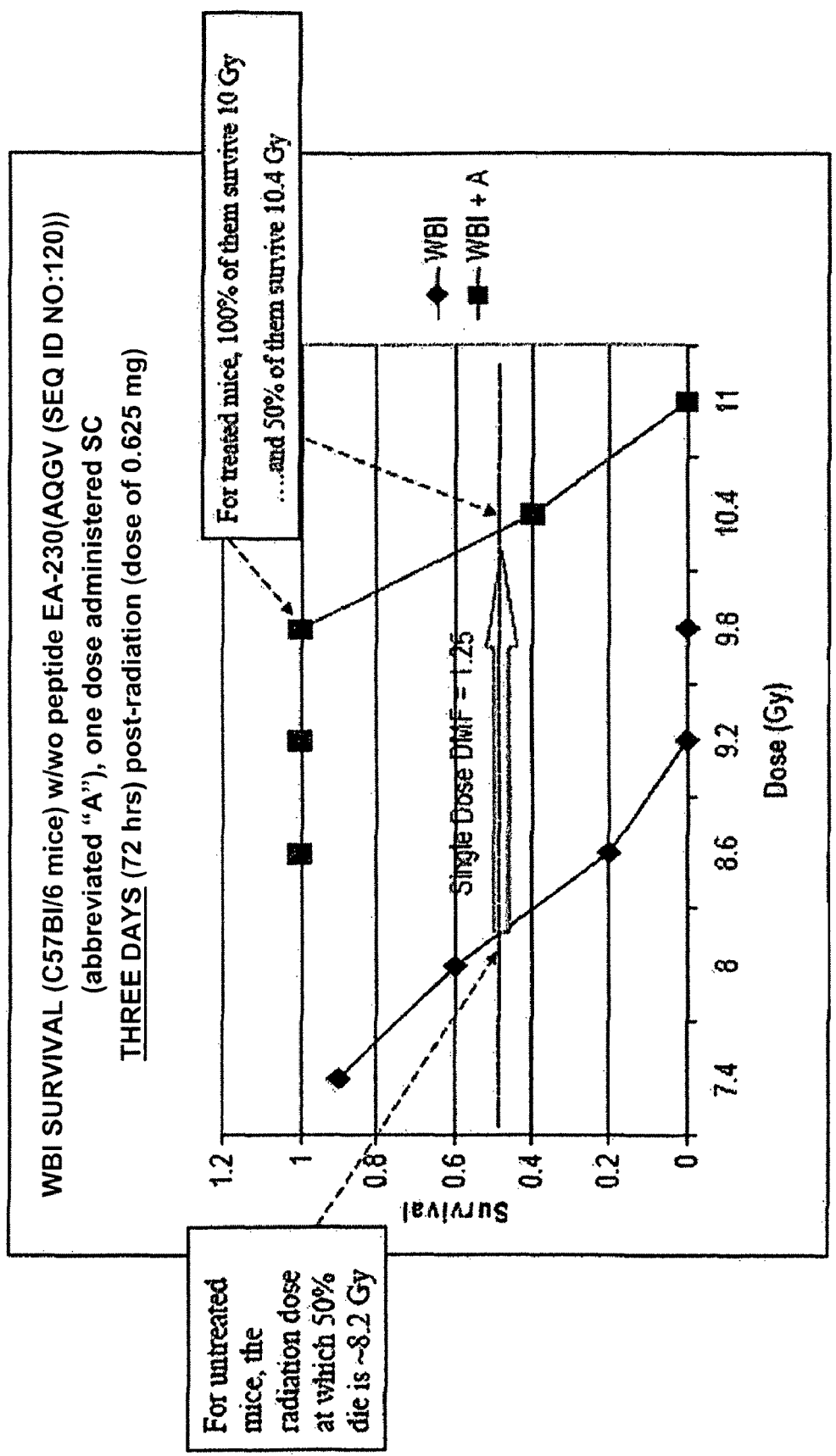

FIG. 2: Second set of radioprotection experiments with peptide AQGV (SEQ ID NO:120).

Escalating doses of Whole Body Irradiation (WBI), with one single exposure given to any particular cohort, and the exposure dose going progressively higher, for each subsequent cohort. A single dose of peptide EA-230 (AQGV (SEQ ID NO:120)) was administered subcutaneously, but with treatment delayed until three days (72 hours) after the WBI. The test is called the Dose Reduction Factor ("DRF"), which is defined as ratio between the LD50 of the treated group to the LD50 of the control group. The LD50 refers to that dose which is lethal to 50% of the animals tested. An acceptable DRF value is 1.20. To pass the test, at Day 30 after WBI, a candidate drug must have an LD50 at a radiation dose that is at least 20% higher (an increase by a factor of 1.20) than the LD50 dose for the control animals. If, e.g., the LD50 for the control animals is 8.2 Gy, then, the LD50 for a candidate drug would have to be at least 20% higher, which in this case, would mean a dose of 8.2×1.20=10.4 Gy.

Figure 3:
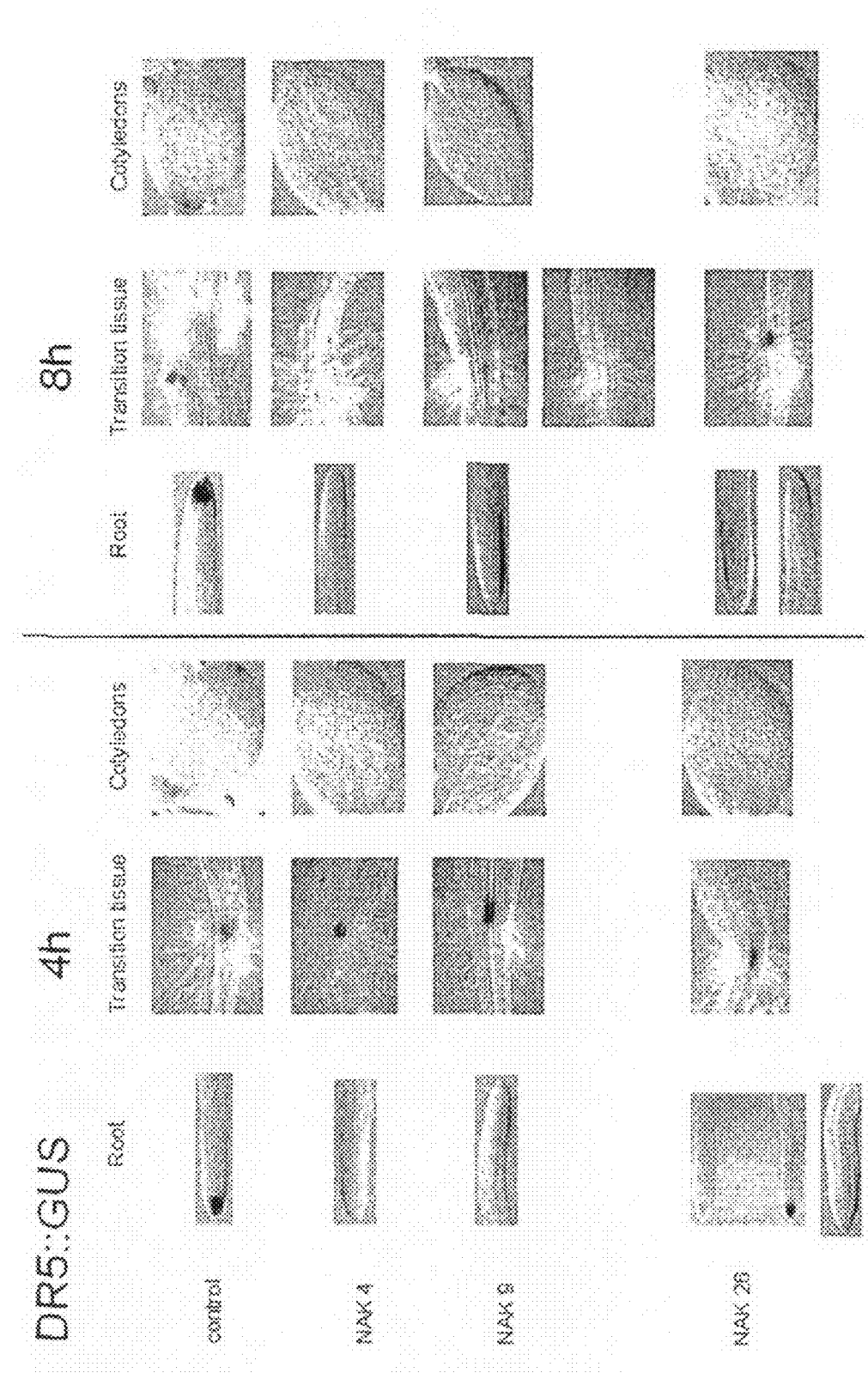

FIG. 3: An example of the effect of oligopeptides in *Arabidopsis thaliana* cell-cycle analysis. Compounds NAK 4 (LQGV (SEQ ID NO:117)) and NAK 9 (VVC) show a clear effect on the tested markers. For the cell-cycle marker (pCDG), a clear effect was observed, for both time points, in the roots. In the transition zone and cotyledons, the effect was observed in a time- and/or dose-dependent manner. In the case of the auxin-responsive marker (DR5::GUS), the same was observed as with the cell-cycle marker. NAK 26 (DINGFLPAL (SEQ ID NO:115)) shows less consistent and time-dependent effect. An effect was only observed in time in the roots. No effect was observed in the transition zone and cotyledons.

Figure 4:
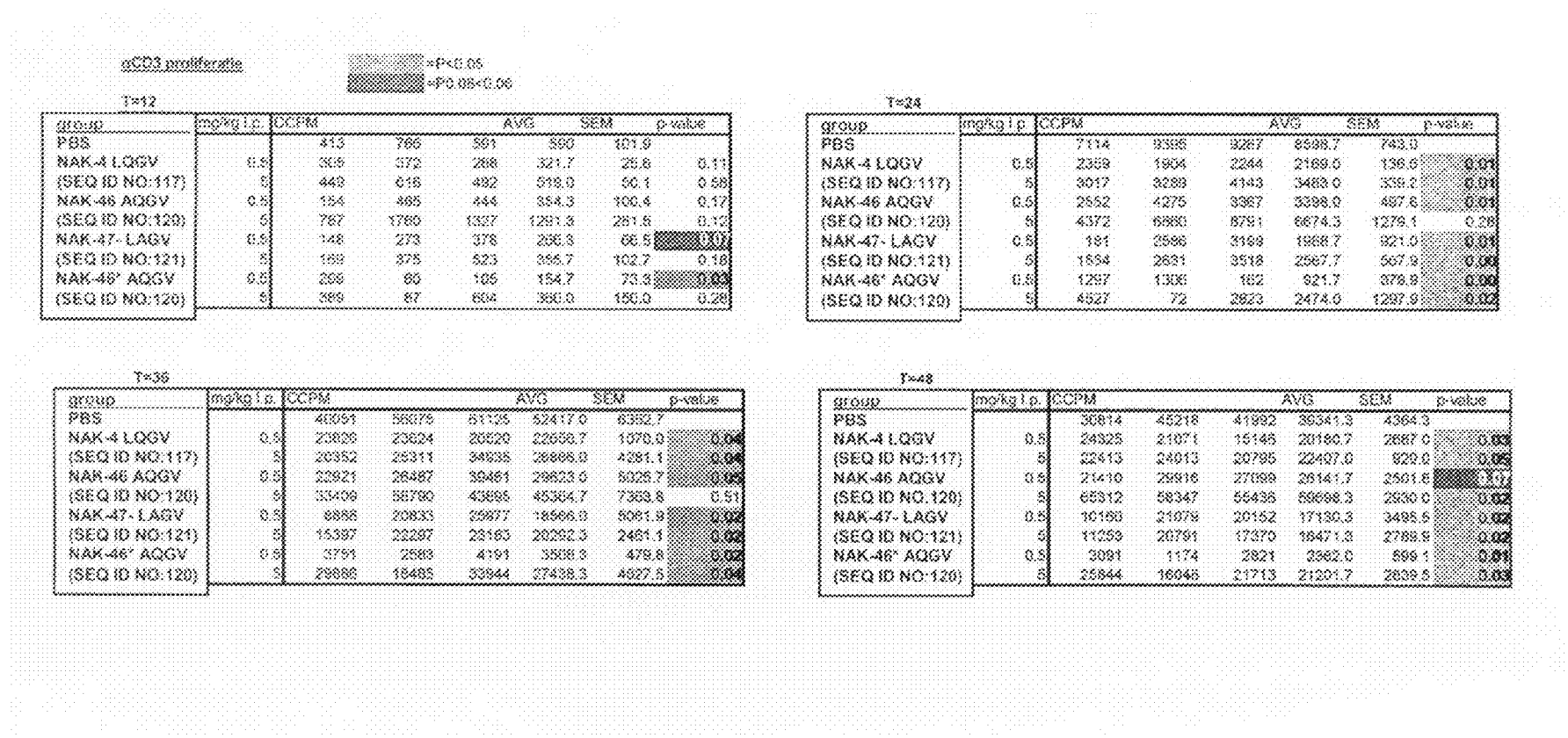

FIG. 4: A test on representative oligopeptides for their effect on proliferation during rapid growth of murine monocytes induced by CD3 when avid cell division occurs. Mice (n=5) were treated i.p. PBS, Nak4 (LQGV (SEQ ID NO:117)), Nak47 (LAGV (SEQ ID NO:121)), Nak46 (AQGV (SEQ ID NO:120)) provided by Ansynth BV, The Netherlands, or Nak46* (AQGV (SEQ ID NO:120) provided by Diosynth BV, The Netherlands). Mice were treated with 0.5 mg/kg of 5 mg/kg peptide for one hour, after which, spleens were isolated and spleen cell suspensions were made. Spleen cell suspensions were pooled per group and cultured in vitro (in three-fold) in the presence of PBS or of anti-CD3 antibody and proliferation was tested at 0, 12, 24 and 48 hours after culture.

DETAILED DESCRIPTION OF THE INVENTION

As used herein, a "purified, synthetic or isolated" peptide is one that has been purified from a natural or biotechnological source or, more preferably, is synthesized as described herein.

"Composition," as used herein, refers to chemical compounds that contain or consist of the oligopeptide. The oligopeptide is preferably isolated before inclusion within the composition. The oligopeptide preferably consists of two (2) to six (6) amino acids, most preferably of three (3) to four (4) amino acids.

For instance, a preferred compound could, in one embodiment be: NT AQGV (SEQ ID NO:120) CT wherein NT at the N-terminus is selected from the group of H—, CH3-, an acyl group, or a general protective group; and CT at the C-terminus is selected from the group of small (e.g., one to five amino acids) peptides, —OH, —OR$^1$, —NH$_2$, —NHR$^1$, —NR$^1$R$^2$, or —N(CH$_2$)$_{1-6}$NR$^1$R$^2$, wherein R$^1$ and R$^2$, when present, are independently selected from H, alkyl, aryl, (ar)alkyl, and wherein R$^1$ and R$^2$ can be cyclically bonded to one another.

"Alkyl," as used herein, is preferably a saturated branched or unbranched hydrocarbon having one to six carbon atoms, for example, methyl, ethyl, and isopentyl.

"Aryl," as used herein, is an aromatic hydrocarbon group, preferably having six to ten carbon atoms, such as phenyl or naphthyl.

"(Ar)alkyl," as used herein, is an arene group (having both aliphatic and aromatic portions), preferably having seven to thirteen carbon atoms such as benzyl, ethylbenzyl, n-propylbenzyl, and isobutylbenzyl.

"Oligopeptide," as used herein, are peptides having from two to twelve amino acids joined together by peptide bonds. Equivalent to oligopeptides are compounds having the same or equivalent side chains as the particular amino acids used in an oligopeptide, and arranged sequentially in the same order as the peptides, but joined together by non-peptide bonds, e.g., by isosteric linkages such as the keto isostere, hydroxy isostere, diketo isostere, or the keto-difluoromethylene isostere.

"Composition" also includes, for example, an acceptable salt of the oligopeptide or a labeled oligopeptide. As used herein, "acceptable salt" refers to salts that retain the desired activity of the oligopeptide or equivalent compound, but preferably do not detrimentally affect the activity of the oligopeptide or other component of a system in which uses the oligopeptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt).

Such a pharmaceutical composition may be administered to the subject parenterally or orally. Such a pharmaceutical composition may consist essentially of oligopeptide and PBS. It is preferred that the oligopeptide is of synthetic origin. Suitable treatment, for example, entails administering the oligopeptide in the pharmaceutical composition to the patient intravenously in an amount of from about 0.1 to about 35 mg/kg body mass of the subject. It may be useful that the pharmaceutical composition consists essentially of from one to three different oligopeptides.

The thus developed chemical entity can be administered and introduced in vivo systemically, topically, or locally. The peptide, or its modification, can be administered as the entity as such or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in situ as a conjugate or be released locally after reaching a targeted tissue or organ.

A "substitution" with regard to the various amino acids generally relate to substituting a group such as alkoxy, halogen, hydroxy, nitro, or lower alkyl onto an aromatic ring for hydrogen that would usually be present. Substitutions can also be made on the alkyl chain connecting the aromatic portion to the peptide backbone with, for instance, lower alkyl groups substituting for hydrogen. Still further substitutions can be made at the alpha position of an amino acid, also using an alkyl group.

Preferred substitutions involve the use of fluorine or chlorine as a halogen, and methoxy as an alkoxy group. With regard to alkyl and lower alkyl, generally alkyl groups having fewer (one to three) carbon atoms are preferred.

The compounds according to the general formula may be prepared in a manner conventional for such compounds. To that end, suitably N-alpha-protected (and side-chain protected if reactive side-chains are present) amino acid analogs or peptides are activated and coupled to suitably carboxyl-protected amino acid or peptide derivatives, either in solution or on a solid support. Protection of the alpha-amino functions generally takes place by urethane functions such as the acid-labile tertiary-butyloxycarbonyl group ("Boc"), benzyloxy-carbonyl ("Z") group and substituted analogs or the base-labile 9-fluoremyl-methyloxycarbonyl ("Fmoc") group. The Z group can also be removed by catalytic hydrogenation. Other suitable protecting groups include the Nps, Bmv, Bpoc, Aloc, MSC, etc. A good overview of amino-protecting groups is given in *The Peptides, Analysis, Synthesis, Biology*, Vol. 3, E. Gross and J. Meienhofer, eds. (Academic Press, New York, 1981). Protection of carboxyl groups can take place by ester formation, for example, base-labile esters like methyl or ethyl, acid labile esters like tert. butyl or, substituted benzyl esters or hydrogenolytically. Protection of side-chain functions like those of lysine and glutamic or aspartic acid can take place using the aforementioned groups. Protection of thiol, and although not always required, of guanidino, alcohol and imidazole groups, can take place using a variety of reagents such as those described in *The Peptides, Analysis, Synthesis, Biology*, id., or in *Pure and Applied Chemistry*, 59(3), 331-344 (1987). Activation of the carboxyl group of the suitably protected amino acids or peptides can take place by the azide, mixed anhydride, active ester, or carbodiimide method especially with the addition of catalytic- and racemization-suppressing compounds like 1-N—N-hydroxybenzotriazole, N-hydroxysuccinimide, 3-hydroxy-4-oxo-3,4-dihydro-1,2,3,-benzotriazine, N-hydroxy-5 norbornene-2,3-dicar-boxyimide. Also the anhydrides of phosphorus-based acids can be used. See, e.g., *The Peptides, Analysis, Synthesis, Biology*, supra, and *Pure and Applied Chemistry*, 59(3), 331-344 (1987).

It is also possible to prepare the compounds by the solid phase method of Merrifield. Different solid supports and different strategies are known; see, e.g. Barany and Merrifield in *The Peptides, Analysis, Synthesis, Biology*, Vol. 2, E. Gross and J. Meienhofer, eds. (Acad. Press, New York, 1980); Kneib-Cordonier and Mullen, *Int. J. Peptide Protein Res.*, 30, 705-739 (1987); and Fields and Noble, *Int. J. Peptide Protein Res.*, 35, 161-214 (1990). The synthesis of compounds in which a peptide bond is replaced by an isostere can, in general, be performed using the previously described protecting groups and activation procedures. Procedures to synthesize the modified isosteres are described in the literature, e.g., for the —$CH_2$—NH— isostere and for the —CO—$CH_2$— isostere.

Removal of the protecting groups and, in the case of solid phase peptide synthesis, the cleavage from the solid support, can take place in different ways, depending on the nature of those protecting groups and the type of linker to the solid support. Usually, deprotection takes place under acidic conditions and in the presence of scavengers. See, e.g. volumes 3, 5 and 9 of the series on *The Peptides Analysis, Synthesis, Biology*, supra.

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds. (Acad. Press, New York, 1987).

Although possibly not desirable from an economic point of view, oligopeptides according to the invention could also be made according to recombinant DNA methods. Such methods involve the preparation of the desired oligopeptide thereof by means of expressing a recombinant polynucleotide sequence that codes for one or more of the oligopeptides in question in a suitable microorganism as host. Generally, the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eukaryotic or prokaryotic host cell, and culturing the host cell thus transformed. When a eukaryotic host cell is used, the compound may include a glycoprotein portion.

As used herein, a "functional analogue" of a peptide includes an amino acid sequence, or other sequence monomers, that has been altered such that the functional properties of the sequence are essentially the same in kind, not necessarily in amount.

The functionality of a peptide or a functional analogue thereof can be determined using in vivo and/or in vitro testing. In vitro testing is preferred. In one embodiment, a functional peptide analogue is subjected to comparative testing using a reference or control peptide, for instance, a peptide analog consisting solely of L-amino acids. A suitable test comprises determining the capability of the candidate peptide to affect cell-cycle dynamics. For example, the effect on cell-cycle progression may be determined using a plant model system, e.g., the *Arabidopsis* system exemplified herein below, or using cultured (mammalian) cells. In a further aspect, it involves determining the ability of the candidate peptide to inhibit apoptosis, for example, by inducing a (temporary) G2-M cell-cycle arrest.

An analogue can be provided in many ways, for instance, through "conservative amino acid substitution." Also, peptidomimetic compounds can be designed that functionally or structurally resemble the original peptide taken as the starting point but that are, for example, composed of non-naturally occurring amino acids or polyamides. With "conservative amino acid substitution," one amino acid residue is substituted with another residue with generally similar properties (size, hydrophobicity), such that the overall functioning is likely not to be seriously affected. However, it is often much more desirable to improve a specific function. An analogue can also be provided by systematically improving at least one desired property of an amino acid sequence. This can, for instance, be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

An analogue can also be, for instance, generated by substitution of an L-amino acid residue with a D-amino acid residue. This substitution, leading to a peptide that does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics. It has been shown in the art that peptides that are protected by D-amino acids at either one or both termini were found to be more stable than those consisting of L-amino acids only. Other types of modifications include those known in the art of peptide drug development to have beneficial effects for use of the peptide in a pharmaceutical composition. These effects may include improved efficacy, altered pharmacokinetics, increasing stability resulting in a longer shelf-life and less stringent cold chain handling requirements.

In one embodiment of the invention, an anti-radiation peptide comprises a sequence of amino acids joined together in a chain by peptide bonds between their amino and carboxylate groups, wherein at least one amino acid is a D-amino acid. For example, the anti-radiation peptide is selected from the group consisting of VVC, LAG, AQG, LQGV (SEQ ID NO:117), QVVC (SEQ ID NO:118), MTRV (SEQ ID NO:119), AQGV (SEQ ID NO:120), LAGV (SEQ ID NO:121), LQAV (SEQ ID NO:122), PGCP (SEQ ID NO:123), VGQL (SEQ ID NO:124), RVLQ (SEQ ID NO:125), EMFQ (SEQ ID NO:126), AVAL (SEQ ID NO:127), FVLS (SEQ ID NO:2), NMWD (SEQ ID NO:3), LCFL (SEQ ID NO:4), FSYA (SEQ ID NO:6), FWVD (SEQ ID NO:7), AFTV (SEQ ID NO:8), LGTL (SEQ ID NO:16), QLLG (SEQ ID NO:18), YAIT (SEQ ID NO:19), APSL (SEQ ID NO:22), ITTL (SEQ ID NO:23), QALG (SEQ ID NO:24), GVLC (SEQ ID NO:26), NLIN (SEQ ID NO:30), SPIE (SEQ ID NO:33), LNTI (SEQ ID NO:36), LHNL (SEQ ID NO:40), CPVQ (SEQ ID NO:128), EVVR (SEQ ID NO:129), MTEV (SEQ ID NO:130), EALE (SEQ ID NO:131), EPPE (SEQ ID NO:132), LGTL (SEQ ID NO:133), VGGI (SEQ ID NO:134), RLPG (SEQ ID NO:135), LQGA (SEQ ID NO:136), LCFL (SEQ ID NO:137), TLAVE (SEQ ID NO:46), VEGNL (SEQ ID NO:138), LNEAL (SEQ ID NO:139), VLPALP (SEQ ID NO:140), MGGTWA (SEQ ID NO:44), LTCDDP (SEQ ID NO:54), VLPAPLQ (SEQ ID NO:141), VCNYRDV (SEQ ID NO:48), CPRGVNP (SEQ ID NO:142), QPLAPLVG (SEQ ID NO:116) and DINGFLPAL (SEQ ID NO:115), wherein at least one of the amino acid residues indicated by the standard one-letter code is a D-amino acid.

A person skilled in the art is well able to generate analogous compounds of an amino acid sequence. This can, for instance, be done through screening of a peptide library. Such an analogue has essentially the same functional properties of the sequence in kind, not necessarily in amount. Also, peptides or analogues can be circularized, for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation. Synthetic versions of these oligopeptides as described above, and functional analogues or breakdown products, are herein provided to be used in methods of the treatment of radiation injury and subsequent disease.

As used herein, a "functional analogue" of a peptide is preferably smaller than the peptide from which it is derived and thus rather made by deletions and/or substitutions than by additions in size. Also, as used herein, a "functional analogue" of a peptide does not refer to a larger protein or peptide merely containing an amino acid sequence identified as an anti-radiation peptide that is flanked by more amino acids at one or both sides.

The term "pharmaceutical composition," as used herein, is intended to cover both the active composition of the invention alone or a composition containing the composition of the invention together with a pharmaceutically acceptable carrier, diluent or excipient. Of course, a pharmaceutical composition may comprise a mixture of at least two anti-radiation peptides or analogs as disclosed herein. Acceptable diluents of an oligopeptide as described herein in the detailed description are, for example, physiological salt solutions or phosphate-buffered salt solutions. In one embodiment, an oligopeptide or composition is administered in an effective concentration to an animal or human systemically, for example, by intravenous, intra-muscular or intraperitoneal administration. Another way of administration comprises perfusion of organs or tissue, be it in vivo or ex vivo, with a perfusion fluid comprising an oligopeptide or composition according to the invention. The administration may be done as a single dose, as a discontinuous sequence of various doses, or continuously for a period of time sufficient to permit substantial modulation of gene expression. In the case of a continuous administration, the duration of the administration may vary depending upon a number of factors that would readily be appreciated by those skilled in the art.

The administration dose of an active molecule may be varied over a fairly broad range. The concentrations of an active molecule that can be administered are typically limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

The active molecule may be administered directly in a suitable vehicle, such as, for example, phosphate-buffered saline ("PBS") or solutions in alcohol or DMSO. Pursuant to preferred embodiments of the present invention, however, the active molecule is administered through a single dose delivery using a drug-delivery system. A suitable drug-delivery system would be pharmacologically inactive or at least tolerable. It should preferably not be immunogenic nor cause inflammatory reactions, and should permit release of the active molecule so as to maintain effective levels thereof over the desired time period. Alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers and implants; and polymeric delivery materials, such as polyethylene oxide/polypropylene oxide block copolymers, polyesters, cross-linked polyvinyl alcohols, polyanhydrides, polymethacrylate and polymethacrylamide hydrogels, anionic carbohydrate polymers, etc. Useful delivery systems are well known in the art.

One formulation to achieve the active molecule release comprises injectable microcapsules or microspheres made from a biodegradable polymer, such as poly(dl-lactide), poly (dl-lactide-co-glycolide), polycaprolactone, polyglycolide, polylactic acid-co-glycolide, poly(hydroxybutyric acid), polyesters or polyacetals. Injectable systems comprising microcapsules or microspheres having a diameter of about 50 to about 500 micrometers offer advantages over other delivery systems. For example, they generally use less active molecules and may be administered by paramedical personnel. Moreover, such systems are inherently flexible in the design of the duration and rate of separate drug release by selection of microcapsule or microsphere size, drug loading and dosage administered. Further, they can be successfully sterilized by gamma irradiation.

The design, preparation, and use of microcapsules and microspheres are well within the reach of persons skilled in the art and detailed information concerning these points is available in the literature. Biodegradable polymers (such as lactide, glycolide and caprolactone polymers) may also be used in formulations other than microcapsules and microspheres; e.g., pre-made films and spray-on films of these polymers containing the active molecule would be suitable for use in accordance with the present invention. Fibers or filaments comprising the active molecule are also contemplated as within the scope of the present invention.

Another highly suitable formulation for a single-dose delivery of the active molecule in accordance with the present invention involves liposomes. The encapsulation of an active molecule in liposomes or multilamellar vesicles is a well-known technique for targeted drug delivery and prolonged drug residence. The preparation and use of drug-loaded liposomes is well within the reach of persons skilled in the art and well documented in the literature.

Yet another suitable approach for single-dose delivery of an active molecule in accordance with the present invention involves the use of viscous instillates. In this technique, high molecular weight carriers are used in admixture with active molecule(s), giving rise to a structure that produces a solution with high viscosity. Suitable high molecular weight carriers include, but are not limited to, the following: dextrans and cyclodextrans; hydrogels; (cross-linked) viscous materials, including (cross-linked) viscoelastics; carboxymethylcellulose; hyaluronic acid; and chondroitin sulfate. The preparation and use of drug-loaded viscous instillates is well known to persons skilled in the art.

Pursuant to yet another approach, active molecule(s) may be administered in combination with absorbable mechanical barriers such as oxidized regenerated cellulose. The active molecule may be covalently or non-covalently (e.g., ionically) bound to such a barrier, or it may simply be dispersed therein.

The invention is further explained with the aid of the following illustrative examples.

EXAMPLES

Peptide Selection

Selection was based on the known preferential cleavage sites of the sequence MTRVLQGVLPALPQVVC (SEQ ID NO:113) (residues 41-57) of loop 2 of the beta-subunit of hCG (Cole et al., 30 *J. Clin. Enclocr. Metab.* 1993; 76:704-710; H. Alfthan, U. H. Stenman, *Mol. Cell. Endocrinol.* 1996; 125:107-120; A. Kardana, et al., *Endocrinology* 1991; 129: 1541-1550; Cole et al., *Endocrinology* 1991; 129:1559-1567; S. Birken, Y. Maydelman, M. A. Gawinowicz, *Methods* 2000; 21:3-14), and on amino acid sequences taken from C-Reactive Protein (CRP) (Beta-catenin, e.g., human CTNB), Bruton's tyrosine kinase (e.g., human BTK), matrix metalloproteinase-2 and p-53.

Peptide Synthesis

Peptides mentioned here were prepared commercially by a proprietary process (Diosynth BV) or by solid-phase synthesis (Ansynth BV) using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H₂O/triisopropylsilane (TIS) 95:2.5:2.5. After 30 minutes, TIS was added until decolorization. The solution was evaporated in vacuo and the peptide precipitated with diethyl ether. The crude peptides were dissolved in water (50 to 100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/minute; absorbance was detected from 190 to 370 nm. There were different gradient systems used. For example, for peptides LQG and LQGV (SEQ ID NO:117): ten minutes 100% A followed by linear gradient 0 to 10% B in 50 minutes. For example, for peptides VLPALP (SEQ ID NO:140) and VLPALPQ (SEQ ID NO:143): five minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

Example 1 and Example 2

In the first experiment, 12-week-old female BALB/c mice were treated intraperitoneally with a single injection of either PBS (n=9) or with a peptide (LQGV (SEQ ID NO:117), VLPALP (SEQ ID NO:140), LPGCPRGVNPVVS (SEQ ID NO:114), MTRVLQGVLPALPQVVC (SEQ ID NO:113); n=8, 10 mg/kg). One and a half hours after the treatment, mice were exposed whole body to a single dose of 10 Gy $^{137}$Cs-γ-irradiation. In the second experiment, 12-week-old female BALB/c mice were first exposed whole body to a single dose of 10 Gy $^{137}$Cs-γ-irradiation and then 1.5 hours after the irradiation treated intraperitoneally with a single injection of either PBS (n=9) or with a peptide (n=8 or 9, 10 mg/kg). During the experiment, mortality and clinical signs (e.g., watery eyes indicating conjunctivitis and weight loss) were observed at different time points. As can be seen from Table 2, all peptides tested had good effect on reducing conjunctivitis in the treated mice, however, no effects were seen on mortality, leading us to select a peptide most suited to combat acute inflammation for testing at a later phase with repeated doses and lowered irradiation.

TABLE 1

Effects of intraperitoneal treatment with peptide (10 mg/kg) in 12-week-old female BALB/c mice 1.5 hours before whole body exposure to (10 Gy) γ-irradiation.

| Mortality | Days after irradiation | | | | | |
|---|---|---|---|---|---|---|
| | 0 | 3 | 4 | 5 | 6 | 7 |
| PBS | 0/9 | 0/9 | 0/9 | 0/9 | 5/9 | 9/9 |
| LQGV (SEQ ID NO: 117) | 0/8 | 0/8 | 0/8 | 0/8 | 7/8 | 8/8 |
| VLPALP (SEQ ID NO: 140) | 0/8 | 0/8 | 0/8 | 0/8 | 7/8 | 8/8 |
| LPGCPRGVNPVVS (SEQ ID NO: 114) | 0/8 | 0/8 | 0/8 | 0/8 | 4/8 | 8/8 |
| MTRVLQGVLPALPQVVC (SEQ ID NO: 113) | 0/8 | 0/8 | 0/8 | 0/8 | 7/8 | 8/8 |

TABLE 1-continued

Effects of intraperitoneal treatment with peptide (10 mg/kg) in 12-week-old female BALB/c mice 1.5 hours before whole body exposure to (10 Gy) γ-irradiation.

| | Days after irradiation | | Weight | Days after irradiation | |
|---|---|---|---|---|---|
| Watery eyes | 0 | 4 | loss | 0 | 4 |
| PBS | 0/9 | 0/9 | | 0/9 | 9/9 |
| LQGV (SEQ ID NO: 117) | 0/8 | 0/8 | | 0/8 | 8/8 |
| VLPALP (SEQ ID NO: 140) | 0/8 | 0/8 | | 0/8 | 8/8 |
| LPGCPRGVNPVVS (SEQ ID NO: 114) | 0/8 | 1/8 | | 0/8 | 8/8 |
| MTRVLQGVLPALPQVVC (SEQ ID NO: 113) | 0/8 | 1/8 | | 0/8 | 1/8 |

TABLE 2

Effects of intraperitoneal treatment with peptide (10 mg/kg) in 12-week-old female BALB/c mice 1.5 hours after whole body exposure to (10 Gy) γ-irradiation.

| Mortality | Days after irradiation | | | | | |
|---|---|---|---|---|---|---|
| | 0 | 3 | 4 | 5 | 6 | 7 |
| PBS | 0/9 | 0/9 | 0/9 | 0/9 | 6/9 | 9/9 |
| LQGV (SEQ ID NO: 117) | 0/9 | 0/9 | 0/9 | 1/9 | 6/9 | 9/9 |
| VLPALP (SEQ ID NO: 140) | 0/9 | 0/9 | 0/9 | 0/9 | 3/9 | 9/9 |
| LPGCPRGVNPVVS (SEQ ID NO: 114) | 0/8 | 0/8 | 0/8 | 0/8 | 6/8 | 8/8 |
| MTRVLQGVLPALPQVVC (SEQ ID NO: 113) | 0/9 | 0/9 | 0/9 | 0/9 | 5/9 | 9/9 |

| | Days after irradiation | | Weight | Days after irradiation | |
|---|---|---|---|---|---|
| Watery eyes | 0 | 4 | loss | 0 | 4 |
| PBS | 0/9 | 6/9 | | 0/9 | 9/9 |
| LQGV (SEQ ID NO: 117) | 0/9 | 3/9 | | 0/9 | 9/9 |
| VLPALP (SEQ ID NO: 140) | 0/9 | 0/9 | | 0/9 | 9/9 |
| LPGCPRGVNPVVS (SEQ ID NO: 114) | 0/8 | 0/8 | | 0/8 | 8/8 |
| MTRVLQGVLPALPQVVC (SEQ ID NO: 113) | 0/9 | 0/9 | | 0/9 | 9/9 |

Example 3

Six oligopeptides (i.e., A: LAGV (SEQ ID NO:121); B: AQGV (SEQ ID NO:120); C: LAG; D: AQG; E: MTR; and F: MTRV (SEQ ID NO:119)) were tested and compared with PBS (control) in a double blind animal study for each peptide's relative ability to aid recovery in a mouse renal ischemia reperfusion test. In this test, the mice were anesthetized, and one kidney from each mouse was removed. The other kidney was tied off for 25 minutes, and the serum urea levels were allowed to increase. Both before and after tying off, each of the separate peptides was administered to thirty (30) different mice (5 mg oligopeptide/kg body mass intravenously), after which, the mortality of the mice was determined for each oligopeptide as well as was the BUN concentration at two hours, 24 hours and 72 hours. The results are shown in Table 3 below (excluding the results of peptide A (LAGV (SEQ ID NO:121)) obtained in Example 3).

Under inhalation anesthesia, the left kidney with its artery and vein was isolated and occluded for 25 minutes using a microvascular clamp. During surgery, animals were placed on a heating pad to maintain body temperature at 37° C. Five minutes before placing the clamp, and five minutes before releasing the clamp, 5 mg/kg of peptide dissolved in 0.1 mL of sterile saline, was administered intravenously. After reperfusion of the left kidney, the right kidney was removed. Kidney function was assessed by measuring blood urea nitrogen before clamping, and at 2, 24, and 72 hours after reperfusion.

TABLE 3

Results (mortality at 72 hours post-reperfusion)

| PBS | A (LAGV) (SEQ ID NO: 121) | B (AQGV) (SEQ ID NO: 120) | C (LAG) | D (AQG) | E (MTR) | F (MTRV) (SEQ ID NO: 119) |
|---|---|---|---|---|---|---|
| 6/10 | 6/10 | 0/10 | 4/10 | 4/10 | 4/10 | 2/10 |
| *P < (vs PBS) | NS | 0.01 | 0.01 | 0.01 | 0.01 | 0.01 |

*2 × 2 Chi-square test. df = 1

Peptide A (SEQ ID NO:121) was the first peptide administered in the renal ischemia reperfusion test. The personnel who performed the experiments went through a learning curve while working with peptide A. During administration of the peptide in the inferior caval vein, some animals experienced moderate blood loss from the site of injection, whereas others did not. Inadvertently the animals were returned to the stable without drinking water present in their cages the first night after surgery. Also, by mistake, the animals that were intended to be sacrificed at 72 hours were killed 48 hours after reperfusion. None of these or other problems were encountered during the experiments with peptides B-F.

As can be seen, mice administered the oligopeptides MTRV (SEQ ID NO:119) and especially AQGV (SEQ ID NO:120) did much better in terms of both survival (a significant reduction in mortality versus the PBS control group) and reduced BUN concentration than the control group (PBS) or the group administered the other oligopeptides, with more mice surviving and the serum urea levels being much lower than in the other groups. However, the oligopeptides LAG, AQG, and MTR, in this experiment having no reducing effect on BUN concentration, each caused a significant reduction of mortality compared to the PBS control, where MTR did significantly raise BUN levels in the tested mice at 72 hours.

Example 4

One oligopeptide (A) (SEQ ID NO:121) was retested for its capacity to reduce BUN levels in the mice test for the reasons as described above. The results are shown in Table 4 below. As can be seen, mice administered the oligopeptide LAGV (SEQ ID NO:121) now did much better in terms of both survival (a significant reduction in mortality versus the PBS control group) and reduced BUN concentration than the control group (PBS).

Example 5

Four additional oligopeptides (G (VLPALPQ (SEQ ID NO:143)), H (VLPALP (SEQ ID NO:140)), I (LQGV (SEQ ID NO:117)) and J (LQG)) were tested for their capacity to reduce BUN levels in the mice test as described above. The results are shown in Table 4 below. As can be seen, mice administered the oligopeptide LQG did show reduced BUN concentration early in the experiment (at 24 hours post-reperfusion) and mice administered VLPALPQ (SEQ ID NO:143) did much better in terms of reduced BUN concentration late in the experiment (at 72 hours post-reperfusion) than the control group (PBS) or the group administered the other oligopeptides, with more mice surviving and the serum urea levels being much lower than in the other groups.

TABLE 4

BUN after 25 minutes renal ischemia tested in mice with peptides A-J

| Peptide | | t = 0 hr | 2 hours | 24 hours | 72 hours | | C-term: CARBOXYL N-term: FREE | |
|---|---|---|---|---|---|---|---|---|
| A | Mean | 8.166667 | 14.03333 | 38.86364 | 32.8875 | NMPF-47 | LAGV (SEQ ID NO: 121) | |
|  | sd | 1.774658 | 1.011599 | 14.54711 | 14.31228 | | | |
|  | N | 18 | 3 | 11 | 8 | | | |
| B | Mean | 9.713333 | 16.62 | 26.36 | 22.31 | NMPF-46 | AQGV (SEQ ID NO: 120) | |
|  | sd | 1.882722 | 2.185203 | 20.62105 | 15.96444 | | | |
|  | N | 30 | 10 | 20 | 10 | | | |
| C | Mean | 10.15185 | 18.13333 | 59.24375 | 74.4 | NMPF-44 | LAG | |
|  | SD | 1.789794 | 1.88326 | 16.19662 | 33.12546 | | | |
|  | N | 29 | 6 | 16 | 6 | | | |
| D | Mean | 9.303846 | 17.7 | 66.75625 | 91.18333 | NMPF-43 | AQG | |
|  | SD | 1.502127 | 1.561135 | 24.50445 | 51.22154 | | | |
|  | N | 26 | 8 | 16 | 6 | | | |
| E | mean | 8.403846 | 17.13 | 66.23333 | 104.0167 | NMPF-12 | MTR | |
|  | SD | 1.739076 | 1.625526 | 17.55069 | 48.97193 | | | |
|  | N | 26 | 10 | 6 | 6 | | | |
| F | mean | 7.462963 | 15.08571 | 34.57368 | 39.8375 | NMPF-11 | MTRV (SEQ ID NO: 119) | |
|  | SD | 1.338526 | 1.422941 | 15.18083 | 21.45973 | | | |
|  |  | 30 | 7 | 18 | 8 | | | |
| G | mean | 8.256667 | 13.58 | 37.79375 | 37.6375 | NMPF-7 | VLPALPQ (SEQ ID NO: 143) | |
|  | SD | 1.304021 | 1.927462 | 18.33007 | 29.32872 | | | |
|  | N | 30 | 7 | 18 | 8 | | | |

TABLE 4-continued

BUN after 25 minutes renal ischemia tested in mice with peptides A-J

| Peptide | | t = 0 hr | 2 hours | 24 hours | 72 hours | C-term: CARBOXYL N-term: FREE | |
|---|---|---|---|---|---|---|---|
| H | mean | 8.423333 | 16.24 | 62.4 | 47.05 | NMPF-6 | VLPALP (SEQ ID NO: 140) |
| | SD | 1.255521 | 1.370482 | 13.33867 | 20.92728 | | |
| | N | 30 | 10 | 9 | 7 | | |
| I | mean | 7.518182 | 17.53333 | 56.08333 | 73.17778 | NMPF-4 | LQGV (SEQ ID NO: 117) |
| | SD | 1.537356 | 2.956913 | 14.53573 | 23.3083 | | |
| | N | 22 | 3 | 18 | 9 | | |
| J | mean | 7.82069 | 16.75 | 26.74 | 83.95714 | NMPF-3 | LQG |
| | SD | 1.330515 | 1.44123 | 15.51796 | 40.32129 | | |
| | N | 29 | 8 | 9 | 8 | | |
| PBS control | mean | 8.172414 | 15.0875 | 56.81 | 82.075 | | |
| | SD | 1.549169 | 2.215167 | 22.4659 | 34.82713 | | |
| | N | 29 | 8 | 15 | 4 | | |

At two hours post-reperfusion statistical analyses revealed P-values of:

| A | p = 0.0491 NMPF-47 | LAGV (SEQ ID NO: 121) |
| B | p = 0.0008 NMPF-46 | AQGV (SEQ ID NO: 120) |
| C | p = 0.9248 NMPF-44 | LAG |
| D | p = 0.4043 NMPF-43 | AQG |
| E | p = 0.1848 NMPF-12 | MTR |
| F | p = 0.0106 NMPF-11 | MTRV (SEQ ID NO: 119) |
| G | p = 0.1389 NMPF-7 | VLPALPQ (SEQ ID NO: 143) |
| H | p = 0.5613 NMPF-6 | VLPALP (SEQ ID NO: 140) |
| I | p = 0.9301 NMPF-4 | LQGV (SEQ ID NO: 117) |
| J | p = 0.0030 NMPF-3 | LQG |

At 24 hours post-reperfusion, statistical analyses revealed P-values of:

| A | p = 0.0017 NMPF-47 | LAGV (SEQ ID NO: 121) |
| B | p < 0.0001 NMPF-46 | AQGV (SEQ ID NO: 120) |
| C | p = 0.8186 NMPF-44 | LAG |
| D | p = 0.2297 NMPF-43 | AQG |
| E | p = 0.0242 NMPF-12 | MTR |
| F | p = 0.0021 NMPF-11 | MTRV (SEQ ID NO: 119) |
| G | p = 0.0049 NMPF-7 | VLPALPQ (SEQ ID NO: 143) |
| H | p = 0.3297 NMPF-6 | VLPALP (SEQ ID NO: 140) |
| I | p = 0.8328 NMPF-4 | LQGV (SEQ ID NO: 117) |
| J | p = 0.9445 NMPF-3 | LQG |

P values were calculated by Mann Whitney U-test (SPSS for Windows).

Example 6

To determine dose-response relationships, two peptides, D (AQG, having a good effect on mortality on the mice tested in Example 3) and B (AQGV (SEQ ID NO:120), also having superior effect on BUN of the mice tested in Example 3), were also tested in a dose-response manner in the mouse renal failure test as described above. Peptides were tested at 0.3, 1, 3, 10 and 30 mg/kg dosages given as described in Example 3. P values (calculated by Mann Whitney U-test (SPSS for Windows)) of serum urea levels of PBS compared to peptide D groups at 72 hours post-clamping were at 0.3 mg/kg 0.001, at 1 mg/kg 0.009, at 3 mg/kg 0.02, at 10 mg/kg 0.000, and at 30 mg/kg 0.23; for peptide B (SEQ ID NO:120) groups, these P-values were 0.88, 0.054, 0.000, 0.001 and 0.003. As can be seen, peptide D (AQG) did reduce BUN levels surprisingly well at the lower dosages tested, as compared with peptide B (AQGV (SEQ ID NO:120)), while the beneficial effect on mortality was also still notable at the lower dosages tested.

TABLE 5

Mortality in dose-response experiment

| | 24 hours | 72 hours |
|---|---|---|
| PBS | 0-9 | 4-8 |
| AQG 0.3 mg/kg | 0-10 | 2-8 |
| AQG 1.0 mg/kg | 0-10 | 1-8 |
| AQG 3.0 mg/kg | 0-10 | 0-10 |
| AQG 10.0 mg/kg | 0-8 | 1-10 |
| AQG 30.0 mg/kg | 0-8 | 1-8 |
| AQGV (SEQ ID NO: 120) 0.3 mg/kg | 0-9 | 2-10 |
| AQGV (SEQ ID NO: 120) 1.0 mg/kg | 0-10 | 1-8 |
| AQGV (SEQ ID NO: 120) 3.0 mg/kg | 1-10 | 0-10 |
| AQGV (SEQ ID NO: 120) 10.0 mg/kg | 0-10 | 0-8 |
| AQGV (SEQ ID NO: 120) 30.0 mg/kg | 0-8 | 3-10 |

TABLE 6

Urea levels in dose-response experiment

| | 24 hours | 72 hours |
|---|---|---|
| PBS | 57.8 | 85.4 |
| Peptide D (AQG) 0.3 mg/kg | 38.4 | 30.4 |
| Peptide D (AQG) 1.0 mg/kg | 48.4 | 38.4 |
| Peptide D (AQG) 3.0 mg/kg | 39.3 | 40.3 |
| Peptide D (AQG) 10.0 mg/kg | 46.8 | 25.8 |
| Peptide D (AQG) 30.0 mg/kg | 52.8 | 58.9 |
| Peptide B (AQGV) (SEQ ID NO: 120) 0.3 mg/kg | 62.4 | 86.7 |
| Peptide B (AQGV) (SEQ ID NO: 120) 1.0 mg/kg | 50.0 | 52.6 |
| Peptide B (AQGV) (SEQ ID NO: 120) 3.0 mg/kg | 37.4 | 19.6 |
| Peptide B (AQGV) (SEQ ID NO: 120) 10.0 mg/kg | 41.2 | 37.1 |
| Peptide B (AQGV) (SEQ ID NO: 120) 30.0 mg/kg | 47.8 | 38.0 |
| standard error | | |
| PBS | 7.1 | 14.7 |
| Peptide D (AQG) 0.3 mg/kg | 8.6 | 3.5 |
| Peptide D (AQG) 1.0 mg/kg | 7.2 | 10.2 |
| Peptide D (AQG) 3.0 mg/kg | 3.5 | 10.7 |
| Peptide D (AQG) 10.0 mg/kg | 8.0 | 3.4 |
| Peptide D (AQG) 30.0 mg/kg | 9.5 | 12.9 |
| Peptide B (AQGV) (SEQ ID NO: 120) 0.3 mg/kg | 10.8 | 14.1 |
| Peptide B (AQGV) (SEQ ID NO: 120) 1.0 mg/kg | 11.7 | 14.3 |
| Peptide B (AQGV) (SEQ ID NO: 120) 3.0 mg/kg | 7.6 | 2.6 |
| Peptide B (AQGV) (SEQ ID NO: 120) 10.0 mg/k | 8.5 | 6.9 |
| Peptide B (AQGV) (SEQ ID NO: 120) 30.0 mg/kg | 5.8 | 7.8 |

TABLE 7 statistical significance/p values (Mann Whitney U-Test) of serum urea levels in dose-response experiment 72 hours post-clamping. PBS control compared to peptide administered groups.

|  | 72 hours |
|---|---|
| PBS | NA |
| AQG 0.3 mg/kg | 0.001 |
| AQG 1.0 mg/kg | 0.009 |
| AQG 3.0 mg/kg | 0.02 |
| AQG 10.0 mg/kg | 0.000 |
| AQG 30.0 mg/kg | 0.23 |
| AQGV (SEQ ID NO: 120) 0.3 mg/kg | 0.88 |
| AQGV (SEQ ID NO: 120) 1.0 mg/kg | 0.054 |
| AQGV (SEQ ID NO: 120) 3.0 mg/kg | 0.000 |
| AQGV (SEQ ID NO: 120) 10.0 mg/kg | 0.001 |
| AQGV (SEQ ID NO: 120) 30.0 mg/kg | 0.003 |

Septic shock experiments were set up to determine which peptide was best suited to battle acute inflammation.

Mice used in sepsis or septic shock experiments: Female BALB/c mice of eight to twelve weeks of age were used for all experiments. The animals were bred in our facility under specific pathogen-free conditions according to the protocols described in the Report of European Laboratory Animal Science Associations (FELASA) Working group on Animal Health (*Laboratory Animals* 28:1-24, 1994).

Injection protocols: For the endotoxin model, BALB/c mice were injected i.p. with 150-300 µg LPS (*E. coli* 026:B6; Difco Lab., Detroit, Mich., USA). Control groups were treated with PBS i.p. only. To test the effect of peptides, they were dissolved in PBS and injected i.p. at predetermined points in time after LPS treatment.

Mice were scored for sickness severity using the following measurement scheme:

0 No abnormalities.
1 Percolated fur, but no detectable behavior differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund, sacrificed).
D Dead.

A first set of septic shock experiments were set up to determine which of the peptides LQG, LQGV (SEQ ID NO:117), VLPALP (SEQ ID NO:140), VLPALPQ (SEQ ID NO:143), MTR, MTRV (SEQ ID NO:119), VVC or QVVC (SEQ ID NO:118) were capable of inhibiting lipopolysaccharide (LPS)-induced septic shock in mice by treating mice with a single dose of peptide at two hours after LPS treatment. Peptides were used at 5 mg/kg bodyweight. BALB/c mice were injected i.p. with escalating doses LPS (*E. coli* 026:B6; Difco Lab., Detroit, Mich., USA), predetermined to be leading to 80 to 100% mortality in 24 to 72 hours. Control groups were treated with PBS i.p. only and showed no mortality.

A second set of septic shock experiments were set up to determine which of the peptides LQG, LQGV (SEQ ID NO:117), VLPALP (SEQ ID NO:140), VLPALPQ (SEQ ID NO:143), MTR, MTRV (SEQ ID NO:119), VVC or AQG, AQGV (SEQ ID NO:120), LAG and LAGV (SEQ ID NO:121) were capable of inhibiting high dose LPS-induced septic shock in mice by treating mice with a double dose of peptide at two and 24 hours after LPS treatment. At each treatment, peptides were used at 5 mg/kg bodyweight. BALB/c mice were injected i.p. with high doses LPS (*E. coli* 026:B6; Difco Lab., Detroit, Mich., USA), predetermined to be leading to 80 to 100% mortality in 24 to 72 hours. Control groups were treated with PBS i.p. only and showed no mortality.

A further set of septic shock experiments were set up to determine which of the peptides LQG, LQGV (SEQ ID NO:117), VLPALP (SEQ ID NO:140), VLPALPQ (SEQ ID NO:143), MTR, MTRV (SEQ ID NO:119), VVC or AQGV (SEQ ID NO:120) under study were most suited to be used early and/or late after or throughout the development of shock. For determining the percent of endotoxin shock survival after late or early treatment with peptide, BALB/c mice were injected i.p. with 300 µg LPS (*E. coli* 026:B6; Difco Lab., Detroit, Mich., USA), predetermined to be leading to 100% mortality in 48 hours without peptide treatment. Control groups were treated with PBS i.p. only and showed no mortality.

A comparative trial was set up to compare peptide MTR and AQGV (SEQ ID NO:120), each obtained from two commercial sources. The comparative trial comprised six groups of six animals; two groups (1A and 1B) receiving placebo (PBS), one group (2) receiving peptide MTR (source Pepscan), one group (3) receiving peptide MTR (source Ansynth), one group (4) receiving peptide AQGV (SEQ ID NO:120) (source Pepscan) and one group (5) receiving peptide AQGV (SEQ ID NO:120) (source Ansynth). Peptide/placebo in these groups was administered two hours after LPS. LPS (source) was used at 10 to 11 mg/kg. Sickness scores were done at 0, 2, 22, 26, 42, and 48 hours after LPS injection.

Results

Peptide Selection

We selected for synthesis the peptides MTR, MTRV (SEQ ID NO:119), LQG, LQGV (SEQ ID NO:117), VLPALP (SEQ ID NO:140) and VLPALPQ (SEQ ID NO:143), as well as QVVC (SEQ ID NO:118) and VVC. In a later phase of the study, we also selected for synthesis alanine-replacement peptides variants derived from LQG and LQGV (SEQ ID NO:117), whereby a single substitution of one amino acid with alanine was made; four (AQG, AQGV (SEQ ID NO:120), LAG, and LAGV (SEQ ID NO:121)) of which the results are presented here.

Septic Shock Experiments

To test the effect of peptide early in the development of shock, mice were treated at two hours or at 24 hours after treatment with varying doses of LPS by i.p. injection with test peptide at 5 mg/kg bodyweight. All LPS doses resulted in 100% mortality at 48 to 72 hours in the non-peptide treated mice. The results are shown in Table 8. Of the seven peptides tested, peptide VLPALP (SEQ ID NO:140) and LQGV (SEQ ID NO:117) showed a marked protective effect against LPS-induced sepsis.

TABLE 8

| Peptide tested | LPS dose | n | \multicolumn{6}{c|}{single dose administration 5 mg/kg} | | | | | | | | |
|---|---|---|---|---|---|---|---|---|---|---|---|---|---|---|---|
| | | | \multicolumn{7}{c|}{effect at t = 24 hours} | \multicolumn{7}{c|}{effect at t = 48 hours} |
| | | | 0 | 1 | 2 | 3 | 4 | 5 | D | 0 | 1 | 2 | 3 | 4 | 5 | D |
| LQG | 7* | 6 | | | | 3 | 3 | | | | | | | | 2 | 4 |
| | 7** | 6 | | | | 3 | 2 | 1 | | | | | 1 | | | 5 |
| | 8 | 6 | | 2 | 1 | 3 | | | | | | 1 | 2 | 3 | | |
| | 8 | 6 | | | | 1 | 4 | 1 | | | | | | | | 6 |
| | 10 | 6 | | | | 2 | 4 | | | | | | | | 2 | 4 |
| | 10 | 6 | | | 1 | 2 | 3 | | | | | 1 | 2 | 3 | | |
| LQGV (SEQ ID NO: 117) | 7* | 6 | | 2 | 4 | | | | | | 6 | | | | | |
| | 7** | 6 | 6 | | | | | | | | 6 | | | | | |
| | 8 | 6 | | | 5 | 1 | | | | | | 5 | 1 | | | |
| | 8 | 6 | | 3 | 3 | | | | | 4 | 2 | | | | | |
| | 10 | 6 | | | 6 | | | | | | 6 | | | | | |
| | 10 | 6 | | 2 | 2 | 1 | 1 | | | | 4 | 1 | | | | 1 |
| VLPALP (SEQ ID NO: 140) | 7* | 6 | | 4 | 2 | | | | | | 5 | 1 | | | | |
| | 7** | 6 | | 5 | 1 | | | | | | 5 | 1 | | | | |
| | 8 | 6 | | | 5 | 1 | | | | | 3 | 2 | 1 | | | |
| | 8 | 6 | | 3 | 3 | | | 2 | | | 3 | 1 | | | | |
| | 8 | 6 | | | 2 | 4 | | | | | 5 | 1 | | | | |
| | 8 | 6 | | 2 | 4 | | | | | | 5 | 1 | | | | |
| | 9 | 5 | | | 3 | 1 | 1 | | | | 1 | 2 | 1 | | 1 | |
| | 9 | 6 | | 2 | 4 | | | | | | 5 | 1 | | | | |
| | 9 | 6 | | | 3 | 2 | 1 | | | | 2 | 1 | 1 | | 2 | |
| | 10 | 6 | | | 3 | | 3 | | | | 3 | | 2 | 1 | | |
| | 10 | 6 | | | 4 | | 2 | | | | 2 | 2 | | | | 2 |
| VLPALPQ (SEQ ID NO: 143) | 7* | 6 | | | | 3 | 3 | | | | | | | 2 | 2 | 2 |
| | 7** | 6 | | | | | 5 | 1 | | | | | | | 6 |
| | 8 | 6 | | 1 | 3 | 2 | | | | | | 1 | 3 | 2 | | |
| | 8 | 6 | | | | 1 | 3 | 2 | | | | | | | | 6 |
| | 10 | 6 | | | | 2 | 4 | | | | | | | 1 | 5 |
| | 10 | 6 | | | 1 | | 2 | 3 | | | | | | 1 | 5 |
| VVC | 7* | 6 | | | 4 | 2 | | | | | 4 | | 2 | | | |
| | 7** | 6 | | | 2 | 1 | 2 | 1 | | 1 | 1 | 1 | | | | 3 |
| | 10 | 6 | | 2 | 2 | 2 | | | | | 2 | 2 | | 2 | | |
| MTRV (SEQ ID NO: 119) | 7* | 6 | | | 3 | 3 | | | | | 4 | | 2 | | | |
| | 7** | 6 | | | 2 | 3 | 1 | | | 3 | 1 | | 2 | | | |
| | 10 | 6 | | 2 | 1 | 2 | 1 | | | 2 | 1 | 1 | | 1 | 1 | |
| | 10 | 6 | | 1 | 2 | 1 | 2 | | | | 3 | | | | | 3 |
| MTR | 7* | 6 | | | 3 | 3 | | | | | | | | 2 | 3 | 1 |
| | 7** | 6 | | 1 | 3 | 1 | 1 | | | 3 | | | | | | 3 |
| | 10 | 6 | | | 2 | 3 | | 1 | | 2 | | | | 1 | 3 | |

TABLE 9

| Peptide tested | LPS dose | n | \multicolumn{7}{c|}{peptide administered twice (t = 2 hours and t = 24 hours 5 mg/kg at high LPS} | | | | | | | |
|---|---|---|---|---|---|---|---|---|---|---|---|---|---|---|---|
| | | | \multicolumn{7}{c|}{effect at t = 24 hours} | \multicolumn{7}{c|}{effect at t = 48 hours} |
| | | | 0 | 1 | 2 | 3 | 4 | 5 | D | 0 | 1 | 2 | 3 | 4 | 5 | D |
| LQG | 10.5 | 5 | | | | | | 5 | | | | | | | | 5 |
| | 11 | 6 | | | | | 6 | | | | | | | | | 6 |
| LQGV (SEQ ID NO: 117) | 10.5 | 5 | | | | | | 5 | | | | | | | | 5 |
| | 11 | 6 | | | | 2 | 4 | | | | | | | 2 | 4 | |
| VLPALP (SEQ ID NO: 140) | 10.5 | 5 | | | | | | 5 | | | | | | | | 5 |
| | 11 | 6 | | | | 2 | 4 | | | | | | 1 | | 6 | |
| VLPALPQ (SEQ ID NO: 143) | 10.5 | 5 | | 1 | 2 | | | 2 | | 3 | | | | | | 2 |
| | 11 | 6 | | | | | 6 | | | | 4 | | | | | 2 |
| | 11 | 6 | | | | | 6 | | | | 2 | 3 | 1 | | | |
| VVC | 10.5 | 5 | 5 | | | | | | | 2 | 3 | | | | | |
| | 11 | 6 | 6 | | | | | | | 2 | 4 | | | | | |
| MTRV (SEQ ID NO: 119) | 10.5 | 5 | | 1 | 1 | 3 | | | | 2 | 3 | | | | | |
| | 11 | 6 | | | 4 | 2 | | | | 6 | | | | | | |
| MTR | 10.5 | 5 | 4 | 1 | | | | | | 5 | | | | | | |
| | 11 | 6 | 6 | | | | | | | 6 | | | | | | |

TABLE 9-continued

| Peptide tested | LPS dose | n | \multicolumn{7}{c|}{peptide administered twice (t = 2 hours and t = 24 hours 5 mg/kg at high LPS} | | | | | | | |
|---|---|---|---|---|---|---|---|---|---|---|---|---|---|---|---|
| | | | \multicolumn{7}{c|}{effect at t = 24 hours} | \multicolumn{7}{c|}{effect at t = 48 hours} |
| | | | 0 | 1 | 2 | 3 | 4 | 5 | D | 0 | 1 | 2 | 3 | 4 | 5 | D |
| AQG | 10.5 | 5 | | 2 | 1 | 2 | | | | | | 2 | 3 | | | |
| | 11 | 6 | | 4 | | 2 | | | | | | 6 | | | | |
| LAG | 10.5 | 5 | | | | | | 5 | | | | | | | | 6 |
| | 11 | 6 | | | | | | 6 | | | | | | | | 6 |
| AQGV (SEQ ID NO: 120) | 10.5 | 6 | | 2 | 3 | | | | | | 5 | | | | | |
| | 11 | 4 | | 2 | 4 | | | | | | 6 | | | | | |
| LAGV (SEQ ID NO: 121) | 10.5 | 5 | | | | 1 | 4 | | | | | | 1 | 4 | | |
| | 11 | 6 | | | 1 | 1 | 3 | 1 | | | | 2 | | 4 | | |

To evaluate the effect of peptide treatment at an early or late point in time of development of shock, mice were treated at two hours or at 24 hours after LPS injection by i.p. injection with test peptide at 5 mg/kg bodyweight. The mice were followed for 84 hours instead of for 48 hours in the earlier experiments. The results are shown in Table 10. Of all tested peptides, only AQGV (SEQ ID NO:120) showed 100% survival and no remaining clinical signs of shock at 84 hours after LPS-treatment when given both early or late in the development of shock.

TABLE 10

Percent of mice surviving LPS-induced sepsis after treatment with a single injection of test peptide (at 5 mg/kg body weight) at two or 24 hours after induction of sepsis by treatment with LPS.

| | \multicolumn{5}{c|}{% Survival in Time (hours)} |
|---|---|---|---|---|---|
| | 0 | 14 | 24 | 48 | 84 |
| \multicolumn{6}{c|}{TREATMENT 2 HOURS AFTER LPS TREATMENT} |
| PBS | 100 | 100 | 100 | 0 | 0 |
| LQG | 100 | 100 | 100 | 0 | 0 |
| LQGV (SEQ ID NO: 117) | 100 | 100 | 100 | 100 | 100 |
| VLPALP (SEQ ID NO: 140) | 100 | 100 | 100 | 100 | 100 |
| VLPALPQ (SEQ ID NO: 143) | 100 | 100 | 100 | 0 | 0 |
| MTR | 100 | 100 | 100 | 100 | 50 |
| MTRV (SEQ ID NO: 119) | 100 | 100 | 100 | 50 | 30 |
| VVC | 100 | 100 | 100 | 80 | 50 |
| AQGV (SEQ ID NO: 120) | 100 | 100 | 100 | 100 | 100 |
| \multicolumn{6}{c|}{TREATMENT 24 HOURS AFTER LPS TREATMENT} |
| PBS | 100 | 100 | 100 | 0 | 0 |
| LQG | 100 | 100 | 100 | 0 | 0 |
| LQGV (SEQ ID NO: 117) | 100 | 100 | 100 | 0 | 0 |
| VLPALP (SEQ ID NO: 140) | 100 | 100 | 100 | 0 | 0 |
| VLPALPQ (SEQ ID NO: 143) | 100 | 100 | 100 | 100 | 100 |
| MTR (SEQ ID NO: 119) | 100 | 100 | 100 | 100 | 100 |
| MTRV | 100 | 100 | 100 | 100 | 100 |
| VVC | 100 | 100 | 100 | 100 | 100 |
| AQGV (SEQ ID NO: 120) | 100 | 100 | 100 | 100 | 100 |

*5 mg/kg BW
n = 10

Comparative trial MTR and AQGV (SEQ ID NO:120), each derived from two sources, all at 5 mg/kg.

TABLE 11

LPS = 10-11 mg/kg
970 = 5 mg/kg LPS compound
971 = 5 mg/kg treatment treatment
Ansynth 12
Ansynth 46

| | No | Sickness Scores | | | | | | Survival % |
|---|---|---|---|---|---|---|---|---|
| | | 0 hours | 2 hours | 22 hours | 26 hours | 42 hours | 48 hours | |
| Group 1A | 1 | 0 | 2 | 4 | 4 | 5 | dead | |
| PBS | 2 | 0 | 2 | 3 | 3 | 5 | dead | |
| | 3 | 0 | 2 | 5 | dead | | | |
| | 4 | 0 | 2 | 3 | 3 | 3 | 2 | |
| | 5 | 0 | 2 | 4 | 4 | dead | | |
| | 6 | 0 | 2 | 5 | 5 | dead | | |
| Group 1B | 1 | 0 | 2 | 4 | 4 | 4 | dead | |
| PBS | 2 | 0 | 2 | 5 | dead | | | |
| | 3 | 0 | 2 | 3 | 3 | 2 | 1 | |
| | 4 | 0 | 2 | 4 | dead | | | |
| | 5 | 0 | 2 | 4 | 4 | 5 | dead | |
| | 6 | 0 | 2 | 5 | 5 | dead | | 17% |
| Group 2 | 1 | 0 | 2 | dead | | | | |
| #970 | 2 | 0 | 2 | 3 | 3 | 5 | dead | |
| Diosynth | 3 | 0 | 2 | 2 | 2 | 2 | 2 | |
| BV MTR | 4 | 0 | 2 | 2 | 2 | 2 | 2 | |
| | 5 | 0 | 2 | 2 | 2 | 4 | dead | |
| | 6 | 0 | 2 | 4 | 5 | dead | | 33% |
| Group 3 | 1 | 0 | 2 | 2 | 1 | 1 | 1 | |
| #Ansynth | 2 | 0 | 2 | 2 | 2 | 2 | 1 | |
| 12 MTR | 3 | 0 | 2 | 4 | 5 | dead | | |
| | 4 | 0 | 2 | 3 | 4 | 4 | dead | |
| | 5 | 0 | 2 | 2 | 3 | 5 | dead | |
| | 6 | 0 | 2 | 2 | 2 | 2 | 2 | 50% |
| Group 4 | 1 | 0 | 2 | 2 | 2 | 2 | 2 | |
| #971 | 2 | 0 | 2 | 3 | 3 | 2 | 1 | |
| Diosynth | 3 | 0 | 2 | 2 | 2 | 2 | 2 | |
| BV | 4 | 0 | 2 | 2 | 2 | 2 | 2 | |
| AQGV | 5 | 0 | 2 | 4 | 5 | dead | | |
| (SEQ ID NO: 120) | 6 | 0 | 2 | 2 | 3 | 2 | 1 | 83% |
| Group 5 | 1 | 0 | 2 | 3 | 3 | 2 | 1 | |
| #Ansynth | 2 | 0 | 2 | 3 | 3 | 3 | 1 | |
| 46 AQGV | 3 | 0 | 2 | 2 | 2 | 1 | 1 | |
| (SEQ ID NO: 120) | 4 | 0 | 2 | 4 | 4 | 5 | dead | |
| | 5 | 0 | 2 | 2 | 2 | 1 | 1 | |
| | 6 | 0 | 2 | 2 | 2 | 1 | 1 | 83% |

Several reports have suggested modulation of the immune system by intact hCG, but such effects of breakdown products have not been reported in the scientific literature. Benner and Khan (*Scand. J. Immunol.* July 2005; 62 Suppl. 1:62-6) studied the possible immunological activity of the in vivo-liberated peptide fragments originating from nicking of the sequence MTRVLQGVLPALPQVVC (SEQ ID NO:113) (residues 41-57) of loop 2 of the beta-subunit of hCG, in lieu of the fact that peptides as small as three to seven amino acids generally are not supposed to have significant biological activity.

We have designed peptides that block completely LPS-induced septic shock in mice, in several cases even when treatment with these peptides is started up to 24 hours after LPS injection. These peptides are also able to inhibit the production of MIF. This finding provides the possibility of therapeutic use of these peptides for the treatment of patients suffering from radiation injury.

Example 7

This example shows the results of experiment with peptide AQGV (SEQ ID NO:120) on Whole Body Irradiation (WBI) of mice with 8.6 Gy, whereby all groups of mice got the first injection three hours after the WBI. The group that got a placebo injection experienced 80% mortality, as predicted in this model. The dose of radiation given (8.6 Gray=8.6 Gy) is known, in this species, to cause about an 80% mortality, so it is called the LD80 (lethal dose for 80%). The deaths starting around Day 10, which is typical for what happens in WBI to animals or humans. By around Day 10, the gut lining is so damaged and leaky from the radiation that bacteria get into the circulation and cause sepsis because of Gastrointestinal (GI) Syndrome, and the bone marrow is so damaged that there is an insufficient number of white blood cells to fight the infection ("Bone Marrow Syndrome"), and death ensues.

Figure 1:
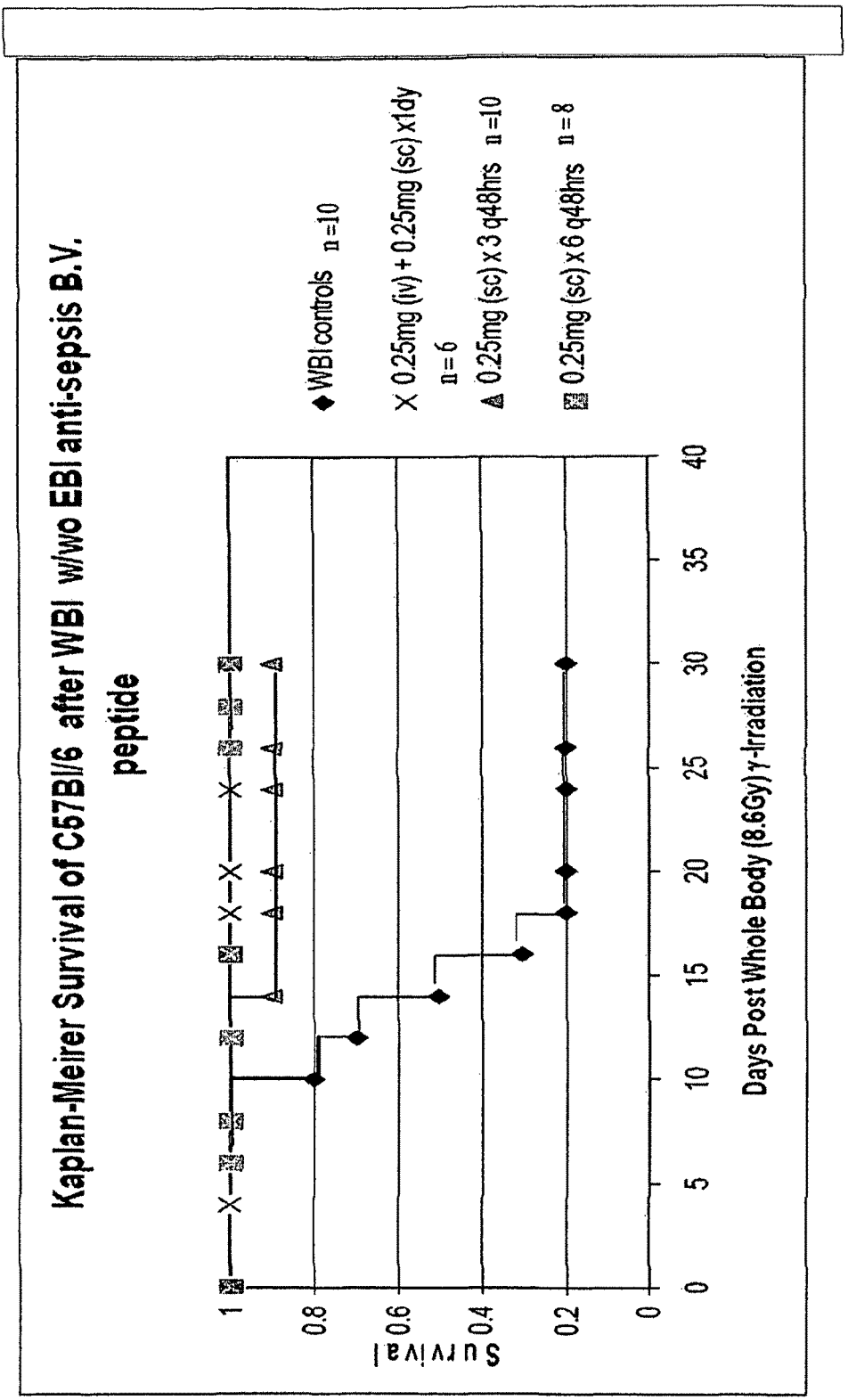
FIG. 1: Whole Body Irradiation of mice treated with AQGV (peptide EA-230).

A first group of peptide-treated mice (group with "x" as the symbol in FIG. 1) got the first injection with AQGV (SEQ ID NO:120) IV, and the second injection subcutaneously (SC) three hours after that first injection. Surprisingly, 100% of these survived. Furthermore, the animals did not show any signs of sickness at all. To an outside observer, they would look like perfectly normal mice; in particular, the peptide-treated mice did not show the GI syndrome.

A second group of mice got its first injection of the peptide via the SC route. Then it got additional SC injections every 48 hours, for a total of three doses (in addition to the first dose), meaning, on Day 3, Day 5, and Day 7. Note that only one of these animals died; others were not showing any symptoms of the GI syndrome.

The third group of mice was identical in procedures to the group with the second group, except that the q48 hour SC injections continued on until a total of six doses had been injected (in addition to the first dose). So the dosing continued on until Day 13. Note that this prolonging of the treatment was associated with complete protection (no mortality whatsoever in this group). The animals in this group showed no signs of sickness; again not showing any symptoms of the GI syndrome.

What we can conclude from this data is that when the animals got two doses of peptide in the first day (with the first one being IV) with AQGV (SEQ ID NO:120), there was complete protection against a highly lethal dose of WBI and, in particular, against the GI syndrome associated with that dose. When the animals got lower-level treatment (SC only), if the treatment was prolonged until the second week, here again, there was complete protection and, in particular, against the GI syndrome associated with the high dose used.

When comparing these results to published information on studies describing the radiation protection activity of a drug code-named ON-01210 that were presented at the 51st Radiation Research Society (April, 2004), it shows that this particular drug ON-01210 (like several other non-peptide drugs that are currently under investigation for radiation exposure) is protective only if it is given pre-radiation exposure. That makes it not very useful for protection against dirty bombs. This particular drug has a sulfhydryl component (4-carboxy-styrl-4-chlorobenzylsulfone) that works as an antioxidant, scavenging the free radicals that are generated as the radiation damages the cells. If it is not present in the body at the time of the radiation exposure, it has no effect whatsoever. In contrast, treating with a peptide according to the invention works after exposure.

Also, when reviewing treatment with other available drugs, all the current data given on such drugs (i.e., on treatment with anabolic steroids) show the need for current non-peptide drugs to being given prior (i.e., 24 hours) to the WBI, later administration has no supportive effect whatsoever on protection against acute radiation injury.

Example 8

DRF Studies

In this example we report on escalating dose studies of Whole Body Irradiation (WBI) with one single exposure given to any particular cohort, and the exposure dose going progressively higher for each subsequent cohort. A single dose of peptide AQGV (SEQ ID NO:120) (10 mg/kg) was administered subcutaneously, but with treatment delayed until three days (72 hours) after the WBI. The test is called the Dose Reduction Factor ("DRF"), which is defined as ratio between the LD50 of the treated group to the LD50 of the control group. The LD50 refers to that dose which is lethal to 50% of the animals tested.

An acceptable DRF ratio is a factor of at least 1.10; but preferred is at least 1.20 or even at least 1.25. To pass the test for DRF 1.20, at Day 30 after WBI, a candidate drug must have an LD50 at a radiation dose that is at least 20% higher (an increase by a factor of 1.20) than the LD50 dose for the control animals. If, e.g., the LD50 for the control animals is 8.2 Gy, then, to pass this test, the LD50 for a candidate drug would have to be at least 20% higher, which in this case would mean a dose of 8.2×1.20=10.4 Gy.

Numbers of animals tested and results in DRF test can be found in Table 12.

TABLE 12

| Dose (Gy) | "n" | The absolute number of animals alive at 30 days post WBI | Percent alive at day 30 | Percent dead at day 30 |
| --- | --- | --- | --- | --- |
| 7.4 | 50 | 45 | 90% | 10% |
| 8 | 100 | 60 | 60% | 40% |
| 8.6 | 120 | 24 | 20% | 80% |
| 9.2 | 30 | 0 | 0% | 100% |
| 8.6 + AQGV (SEQ ID NO: 120) at day 3 | 20 | 20 | 100% | 0% |
| 9.2 + AQGV (SEQ ID NO: 120) at day 3 | 10 | 10 | 100% | 0% |
| 9.8 + AQGV (SEQ ID NO: 120) at day 3 | 10 | 10 | 100% | 0% |
| 10.4 + AQGV (SEQ ID NO: 120) at day 3 | 10 | 4 | 40% | 60% |
| 11.0 + AQGV (SEQ ID NO: 120) at day 3 | 10 | 0 | 0% | 100% |

It is important to discuss the rationale for the decision to delay treatment for 72 hours. In some scenarios of radioactive exposure (e.g., explosion of a nuclear fission device on a cargo ship or a plane crashing into a nuclear reactor near metropolitan centers, etc.), the amount of destruction could be such that it could take several days to get all the victims to treatment centers. Therefore, military scientists (interested in protecting the first responders) and civilian scientists (interested in treating the mass casualties) would naturally want to determine if a candidate drug can do anything to diminish the acute radiation toxicity (GI syndrome, Bone Marrow Syndrome) that will otherwise be fulminant after so long a delay.

Results of DFR Test with AQGV (SEQ ID NO:120)

The radiation dose that kills 50% of the controls turns out to be ~8.2 Gy. Peptide AQGV (SEQ ID NO:120) is so protective that one has to increase the radiation dose by 25% (a factor of 1.25), all the way to ~10.4 Gy, to kill 50% of the animals, and this is with treatment delayed for three (3) days. If the treatment had been given sooner, e.g., at 24 hours or 48 hours, it would have taken an even higher dose of radiation to kill 50% of the animals.

Example 9

To further study anti-cell-cycle activity of various oligopeptides, a proliferation experiment in *Arabidopsis Thaliana* seedlings was performed. The aim was to test a group of 140 oligopeptides of varying length for their effect on plant marker gene expression during rapid growth when avid cell division occurs. Both marker genes are related to the cell-cycle process, high marker activity represents high cell-cycle activity and no marker activity represents no cell-cycle activity and hence, no proliferation. Examples of the effect of oligopeptides in *Arabidopsis Thaliana* cell-cycle analysis is given in FIG. 3.

Method

The peptides were re-suspended in 1× Phosphate Buffer Saline (PBS) pH 8 to a final concentration of 5 mg/ml. The obtained solutions were then divided through 96-well round bottom plates (Corning Incorporated) at 40 microliters per well. Plates were stored before use at −200° C. for four days. Seeds of *Arabidopsis thaliana* ecotype Ws-0 were surface sterilized in 2% commercial bleach (Gloria) for ten minutes and washed five times with sterile MQ water. The seeds were then re-suspended with 0.1% agar and plated on MS20 plates supplemented with 80 mg/l Kanamycin.

The plates were placed at 40° C. for two nights and then transferred to a climate room at 210° C. and a 16/8 hours photoperiod. After four days of growth, the seedlings were transferred to 96-well plates containing the peptide solutions (four seedlings per well) and incubated for four and eight hours.

For this experiment, *Arabidopsis* homozygous seedlings harboring two reporter genes fused to GUS were used. The first reporter gene used was a cell-cycle marker, pCDG (Carmona et al., *The Plant Journal*, 1999, 20(4), 503-508), and the second, an auxin-responsive marker, DR5::GUS (Ulmasov et al., *The Plant Cell*, Vol. 9, 1963-1971). After incubation with the compounds, the seedlings were stained for GUS. The staining reaction was performed in 100 mM sodium phosphate buffer (pH 7.0) that contained 10 mM EDTA, 10% DMSO, 0.1% Triton X-100, 2 mM X-Gluc, 0.5 mM K3Fe(CN)6 and 0.5 mM K4Fe(CN)6 at 370° C. for 16 hours. To stop the GUS reaction and remove chlorophyl, the seedlings were subsequently treated for one hour with 96% ethanol and then stored in 70% ethanol. Stained seedlings were observed under a stereomicroscope and slides were made with seedlings showing an effect of the compound treatment. Seedlings were fixed and cleared in chloral hydrate solution for detailed microscopic observation and photography under a microscope equipped with DIC optics.

Results

Peptides were tested for an effect on marker gene expression on rapidly growing *Arabidopsis* young seedlings. This was monitored by changes on GUS distribution in different organs: root, root-hypocotyl transition zone and cotyledons.

From the 140 compounds tested, a total of 43 showed a clear effect on the expression of both markers tested. Examples of significant changes caused by the tested compounds are shown in detail at the microscopic level for peptides LQGV (SEQ ID NO:117), VVC and DINGFLPAL (SEQ ID NO:115) in FIG. 3. Surprisingly, the effects were clearly related to the length of the various peptides tested. As can be seen in Table 13 below, anti-cell-cycle activity was over-represented in the short peptides, none of the peptides longer than nine amino acids gave reduction of cell-cycle activity. Of the peptides five to nine amino acids in length, about 22% showed reduction, but of the trimers and tetramers tested, more than 50% showed reduction of cell-cycle activity.

TABLE 13

Frequency distribution of peptides tested positive/peptide length as found in cell-cycle test in *Arabidopsis Thaliana*.

| | #AA | | | | | | | | | |
|---|---|---|---|---|---|---|---|---|---|---|
| | 3 | 4 | 5 | 6 | 7 | 8 | 9 | 10 | 12 | 13 | >14 |
| # | 6 | 65 | 9 | 11 | 10 | 2 | 17 | 7 | 3 | 5 | 5 |
| #+ | 3 | 38 | 3 | 3 | 3 | 1 | 1 | 0 | 0 | 0 | 0 |
| %+ | 50% | 58% | 33% | 27% | 30% | 50% | 6% | 0% | 0% | 0% | 0% |

AA = peptide length in amino acids;
# = number tested;
+ = number found positive;
%+ = percentage positive.

Example 10

To further study anti-cell-cycle activity of various oligopeptides, an in vitro experiment in peripheral blood cells of mice stimulated with anti-CD3 was performed. The aim was to test representative oligopeptides for their effect on proliferation during rapid growth induced by CD3 when avid cell division occurs. Mice (n=5) were treated i.p. PBS, Nak4 (LQGV (SEQ ID NO:117)), Nak47 (LAGV (SEQ ID NO:121)), Nak46 (AQGV (SEQ ID NO:120)) provided by Ansynth BV, The Netherlands, or Nak46* (AQGV (SEQ ID NO:120) provided by Diosynth BV, The Netherlands). Mice were treated with 0.5 mg/kg or 5 mg/kg peptide for one hour after which spleens were isolated and spleen cell suspensions were made. Spleen cell suspensions were pooled per group and cultured in vitro (in three-fold) in the presence of PBS or of anti-CD3 antibody and proliferation was tested at 0, 12, 24 and 48 hours after culture. All tested peptides showed a reduction of proliferation (see FIG. 4).

Results from Examples 9 and 10

From cell-cycle studies in plants and in vitro reduction of proliferation studies in peripheral blood cells, useful 3-mer peptides for treatment of radiation injury were identified, VVC, LAG, AQG. Similarly, useful 4-mer peptides for treatment of radiation injury are LQGV (SEQ ID NO:117), QVVC (SEQ ID NO:118), MTRV (SEQ ID NO:119), AQGV (SEQ ID NO:120), LAGV (SEQ ID NO:121), LQAV (SEQ ID NO:122), PGCP (SEQ ID NO:123), VGQL (SEQ ID NO:124), RVLQ (SEQ ID NO:125), EMFQ (SEQ ID NO:126), AVAL (SEQ ID NO:127), FVLS (SEQ ID NO:2), NMWD (SEQ ID NO:3), LCFL (SEQ ID NO:4), FSYA (SEQ ID NO:6), FWVD (SEQ ID NO:7), AFTV (SEQ ID NO:8), LGTL (SEQ ID NO:16), QLLG (SEQ ID NO:18), YAIT (SEQ ID NO:19), APSL (SEQ ID NO:22), ITTL (SEQ ID NO:23), QALG (SEQ ID NO:24), GVLC (SEQ ID NO:26), NLIN (SEQ ID NO:30), SPIE (SEQ ID NO:33), LNTI (SEQ ID NO:36), LHNL (SEQ ID NO:40), CPVQ (SEQ ID NO:128), EVVR (SEQ ID NO:129), MTEV (SEQ ID NO:130), EALE (SEQ ID NO:131), EPPE (SEQ ID NO:132), LGTL (SEQ ID NO:133), VGGI (SEQ ID NO:134), RLPG (SEQ ID NO:135), LQGA (SEQ ID NO:136), LCFL (SEQ ID NO:137). Useful 5-mer peptides for treatment of radiation injury are TLAVE (SEQ ID NO:46), VEGNL (SEQ ID NO:138), LNEAL (SEQ ID NO:139). Useful 6-mer peptides for treatment of radiation injury are VLPALP (SEQ ID NO:140), MGGTWA (SEQ ID NO:44), LTCDDP (SEQ ID NO:54). Useful 7-mer peptides for treatment of radiation injury are VLPAPLQ (SEQ ID NO:141), VCNYRDV (SEQ ID NO:48), CPRGVNP (SEQ ID NO:142). A useful 8-mer peptide for treatment of radiation injury is QPLAPLVG (SEQ ID NO:116) and a useful 9-mer peptide for treatment of radiation injury is DINGFLPAL (SEQ ID NO:115).

REFERENCES

Khan N. A., A. Khan, H. F. Savelkoul, R. Benner. Inhibition of septic shock in mice by an oligopeptide from the beta-chain of human chorionic gonadotropin hormone. *Hum. Immunol.* January 2002; 63(1):1-7.

Benner R., N. A. Khan. Dissection of systems, cell populations and molecules. *Scand. J. Immunol.* July 2005; 62 Suppl 1:62-6.

Cole L. A., A. Kardana, S.-Y. Park, G. D. Braunstein. The deactivation of hCG by nicking and dissociation. *J. Clin. Endocr. Metab.* 1993; 76:704-710.

Alfthan H., U. H. Stenman. Pathophysiological importance of various molecular forms of human choriogonadotropin. *Mol. Cell. Endocrinol.* 1996; 125:107-120.

Kardana A., M. M. Elliott, M. A. Gawinowicz, S. Birken, L. A. Cole. The heterogeneity of human chorionic gonadotropin (hCG). I. Characterization of peptide heterogeneity in 13 individual preparations of hCG. *Endocrinology* 1991; 129:1541-1550.

Cole L. A., A. Kardana, P. Andrade-Gordon, M. A. Gawinowicz, J. C. Morris, E. R. Bergert, J. O'Connor, S. Birken. The heterogeneity of human chorionic gonadotropin (hCG). III. The occurrence and biological and immunological activities of nicked hCG. *Endocrinology*, 1991; 129:1559-1567.

Birken S., Y. Maydelman, M. A. Gawinowicz. Preparation and analysis of the common urinary forms of human chorionic gonadotropin. *Methods* 2000; 21:3-14.

What is claimed is:

1. A method of treating a subject suffering from or believed to be suffering from acute radiation illness, the method comprising:
administering to the subject a pharmaceutical composition comprising:
a peptide consisting of an amino acid sequence selected from the group consisting of VVC, LAG, AQG, LQGV (SEQ ID NO:117), QVVC (SEQ ID NO:118), MTRV (SEQ ID NO:119), LAGV (SEQ ID NO:121), LQAV (SEQ ID NO:122), PGCP (SEQ ID NO:123), VGQL (SEQ ID NO:124), RVLQ (SEQ ID NO:125), EMFQ (SEQ ID NO:55), AVAL (SEQ ID NO:60), FVLS (SEQ ID NO:2), NMWD (SEQ ID NO:3), LCFL (SEQ ID NO:4), FSYA (SEQ ID NO:6), FWVD (SEQ ID NO:7), AFTV (SEQ ID NO:8), LGTL (SEQ ID NO:16), QLLG (SEQ ID NO:18), YAIT (SEQ ID NO:19), APSL (SEQ ID NO:22), ITTL (SEQ ID NO:23), QALG (SEQ ID NO:24), GVLC (SEQ ID NO:26), NLIN (SEQ ID NO:30), SPIE (SEQ ID NO:33), LNTI (SEQ ID NO:36), LHNL (SEQ ID NO:40), CPVQ (SEQ ID NO:128), EVVR (SEQ ID NO:129), MTEV (SEQ ID NO:130), EALE (SEQ ID NO:131), EPPE (SEQ ID NO:132), LGTL (SEQ ID NO:133), VGGI (SEQ ID NO:134), RLPG (SEQ ID NO:135), LQGA (SEQ ID NO:136), LCFL (SEQ ID NO:137), TLAVE (SEQ ID NO:46), VEGNL (SEQ ID NO:138), LNEAL (SEQ ID NO:139), CPRGVNP (SEQ ID NO:142), MGGTWA (SEQ ID NO:44), LTCDDP (SEQ ID NO:54), VCNYRDV (SEQ ID NO:48), QPLAPLVG (SEQ ID NO:116), DINGFLPAL (SEQ ID NO:115) and acceptable salts thereof, and a pharmaceutically acceptable excipient.

2. The method according to claim 1, wherein the radiation illness comprises damage of the lining of the intestinal tract of the subject involving gastrointestinal syndrome.

3. The method according to claim 1, wherein the acute radiation illness is acute irradiation illness.

4. The method according to claim 1, wherein the method of treating comprises subcutaneous or intramuscular injection of the pharmaceutical composition into the subject.

5. The method according to claim 4, wherein the pharmaceutical composition is contained within an autoinjector for injecting the pharmaceutical composition into the subject.

6. The method according to claim 1, wherein the subject is provided with the pharmaceutical composition prior to exposure of the subject to a source of radiation.

7. The method according to claim 1, wherein the subject is provided with the pharmaceutical composition following exposure of the subject to a source of radiation.

8. The method according to claim 1, wherein the pharmaceutical composition comprises a mixture of at least two anti-radiation peptides.

9. The method according to claim 1, wherein the peptide or an acceptable salt thereof is administered to the subject at a dosage of above 1 mg/kg bodyweight of the subject.

* * * * *

SEQUENCE LISTING

```
<160> NUMBER OF SEQ ID NOS: 144

<210> SEQ ID NO 1
<211> LENGTH: 4
<212> TYPE: PRT
<213> ORGANISM: Artificial
<220> FEATURE:
<223> OTHER INFORMATION: CRP-derived peptide
```

-continued

```
<400> SEQUENCE: 1

Leu Thr Ser Leu
1

<210> SEQ ID NO 2
<211> LENGTH: 4
<212> TYPE: PRT
<213> ORGANISM: Artificial
<220> FEATURE:
<223> OTHER INFORMATION: CRP-derived peptide

<400> SEQUENCE: 2

Phe Val Leu Ser
1

<210> SEQ ID NO 3
<211> LENGTH: 4
<212> TYPE: PRT
<213> ORGANISM: Artificial
<220> FEATURE:
<223> OTHER INFORMATION: CRP-derived peptide

<400> SEQUENCE: 3

Asn Met Trp Asp
1

<210> SEQ ID NO 4
<211> LENGTH: 4
<212> TYPE: PRT
<213> ORGANISM: Artificial
<220> FEATURE:
<223> OTHER INFORMATION: CRP-derived peptide

<400> SEQUENCE: 4

Leu Cys Phe Leu
1

<210> SEQ ID NO 5
<211> LENGTH: 4
<212> TYPE: PRT
<213> ORGANISM: Artificial
<220> FEATURE:
<223> OTHER INFORMATION: CRP-derived peptide

<400> SEQUENCE: 5

Met Trp Asp Phe
1

<210> SEQ ID NO 6
<211> LENGTH: 4
<212> TYPE: PRT
<213> ORGANISM: Artificial
<220> FEATURE:
<223> OTHER INFORMATION: CRP-derived peptide

<400> SEQUENCE: 6

Phe Ser Tyr Ala
1

<210> SEQ ID NO 7
<211> LENGTH: 4
<212> TYPE: PRT
<213> ORGANISM: Artificial
<220> FEATURE:
<223> OTHER INFORMATION: CRP-derived peptide
```

```
<400> SEQUENCE: 7

Phe Trp Val Asp
1

<210> SEQ ID NO 8
<211> LENGTH: 4
<212> TYPE: PRT
<213> ORGANISM: Artificial
<220> FEATURE:
<223> OTHER INFORMATION: CRP-derived peptide

<400> SEQUENCE: 8

Ala Phe Thr Val
1

<210> SEQ ID NO 9
<211> LENGTH: 4
<212> TYPE: PRT
<213> ORGANISM: Artificial
<220> FEATURE:
<223> OTHER INFORMATION: CRP-derived peptide

<400> SEQUENCE: 9

Trp Asp Phe Val
1

<210> SEQ ID NO 10
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 10

Gly Leu Leu Gly
1

<210> SEQ ID NO 11
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 11

Thr Ala Pro Ser
1

<210> SEQ ID NO 12
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 12

Val Cys Gln Val
1

<210> SEQ ID NO 13
<211> LENGTH: 4
<212> TYPE: PRT
<213> ORGANISM: Artificial
<220> FEATURE:
<223> OTHER INFORMATION: human beta-catenin-derived peptide
```

```
<400> SEQUENCE: 13

Cys Leu Trp Thr
1

<210> SEQ ID NO 14
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 14

Val His Gln Leu
1

<210> SEQ ID NO 15
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 15

Gly Ala Leu His
1

<210> SEQ ID NO 16
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 16

Leu Gly Thr Leu
1

<210> SEQ ID NO 17
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 17

Thr Leu Val Gln
1

<210> SEQ ID NO 18
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 18

Gln Leu Leu Gly
1

<210> SEQ ID NO 19
<211> LENGTH: 4
<212> TYPE: PRT
<213> ORGANISM: Artificial
<220> FEATURE:
<223> OTHER INFORMATION: human beta-catenin-derived peptide
```

```
<400> SEQUENCE: 19

Tyr Ala Ile Thr
1

<210> SEQ ID NO 20
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 20

Leu Cys Glu Leu
1

<210> SEQ ID NO 21
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 21

Gly Leu Ile Arg
1

<210> SEQ ID NO 22
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 22

Ala Pro Ser Leu
1

<210> SEQ ID NO 23
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 23

Ile Thr Thr Leu
1

<210> SEQ ID NO 24
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 24

Gln Ala Leu Gly
1

<210> SEQ ID NO 25
<211> LENGTH: 4
<212> TYPE: PRT
<213> ORGANISM: Artificial
<220> FEATURE:
<223> OTHER INFORMATION: human beta-catenin-derived peptide
```

```
<400> SEQUENCE: 25

His Pro Pro Ser
1

<210> SEQ ID NO 26
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 26

Gly Val Leu Cys
1

<210> SEQ ID NO 27
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 27

Leu Cys Pro Ala
1

<210> SEQ ID NO 28
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 28

Leu Phe Tyr Ala
1

<210> SEQ ID NO 29
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 29

Asn Ile Met Arg
1

<210> SEQ ID NO 30
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 30

Asn Leu Ile Asn
1

<210> SEQ ID NO 31
<211> LENGTH: 4
<212> TYPE: PRT
<213> ORGANISM: Artificial
<220> FEATURE:
<223> OTHER INFORMATION: human beta-catenin-derived peptide
```

```
<400> SEQUENCE: 31

Leu His Pro Pro
1

<210> SEQ ID NO 32
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 32

Leu Thr Glu Leu
1

<210> SEQ ID NO 33
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 33

Ser Pro Ile Glu
1

<210> SEQ ID NO 34
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 34

Val Gly Gly Ile
1

<210> SEQ ID NO 35
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 35

Gln Leu Leu Tyr
1

<210> SEQ ID NO 36
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 36

Leu Asn Thr Ile
1

<210> SEQ ID NO 37
<211> LENGTH: 4
<212> TYPE: PRT
<213> ORGANISM: Artificial
<220> FEATURE:
<223> OTHER INFORMATION: human beta-catenin-derived peptide
```

```
<400> SEQUENCE: 37

Leu Trp Thr Leu
1

<210> SEQ ID NO 38
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 38

Leu Tyr Ser Pro
1

<210> SEQ ID NO 39
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 39

Tyr Ala Met Thr
1

<210> SEQ ID NO 40
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 40

Leu His Asn Leu
1

<210> SEQ ID NO 41
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 41

Thr Val Leu Arg
1

<210> SEQ ID NO 42
<211> LENGTH: 4
<212> TYPE: PRT
<213> ORGANISM: Artificial
<220> FEATURE:
<223> OTHER INFORMATION: human beta-catenin-derived peptide

<400> SEQUENCE: 42

Leu Phe Tyr Ala
1

<210> SEQ ID NO 43
<211> LENGTH: 9
<212> TYPE: PRT
<213> ORGANISM: Artificial
<220> FEATURE:
<223> OTHER INFORMATION: beta-hCG-derived peptide
```

```
<400> SEQUENCE: 43

Gly Leu Leu Leu Leu Leu Leu Ser
1               5

<210> SEQ ID NO 44
<211> LENGTH: 6
<212> TYPE: PRT
<213> ORGANISM: Artificial
<220> FEATURE:
<223> OTHER INFORMATION: beta-hCG-derived peptide

<400> SEQUENCE: 44

Met Gly Gly Thr Trp Ala
1               5

<210> SEQ ID NO 45
<211> LENGTH: 4
<212> TYPE: PRT
<213> ORGANISM: Artificial
<220> FEATURE:
<223> OTHER INFORMATION: beta-hCG-derived peptide

<400> SEQUENCE: 45

Thr Trp Ala Ser
1

<210> SEQ ID NO 46
<211> LENGTH: 5
<212> TYPE: PRT
<213> ORGANISM: Artificial
<220> FEATURE:
<223> OTHER INFORMATION: beta-hCG-derived peptide

<400> SEQUENCE: 46

Thr Leu Ala Val Glu
1               5

<210> SEQ ID NO 47
<211> LENGTH: 4
<212> TYPE: PRT
<213> ORGANISM: Artificial
<220> FEATURE:
<223> OTHER INFORMATION: beta-hCG-derived peptide

<400> SEQUENCE: 47

Arg Val Leu Gln
1

<210> SEQ ID NO 48
<211> LENGTH: 7
<212> TYPE: PRT
<213> ORGANISM: Artificial
<220> FEATURE:
<223> OTHER INFORMATION: beta-hCG-derived peptide

<400> SEQUENCE: 48

Val Cys Asn Tyr Arg Asp Val
1               5

<210> SEQ ID NO 49
<211> LENGTH: 4
<212> TYPE: PRT
<213> ORGANISM: Artificial
<220> FEATURE:
<223> OTHER INFORMATION: beta-hCG-derived peptide
```

```
<400> SEQUENCE: 49

Phe Glu Ser Ile
1

<210> SEQ ID NO 50
<211> LENGTH: 4
<212> TYPE: PRT
<213> ORGANISM: Artificial
<220> FEATURE:
<223> OTHER INFORMATION: beta-hCG-derived peptide

<400> SEQUENCE: 50

Arg Leu Pro Gly
1

<210> SEQ ID NO 51
<211> LENGTH: 4
<212> TYPE: PRT
<213> ORGANISM: Artificial
<220> FEATURE:
<223> OTHER INFORMATION: beta-hCG-derived peptide

<400> SEQUENCE: 51

Pro Arg Gly Val
1

<210> SEQ ID NO 52
<211> LENGTH: 5
<212> TYPE: PRT
<213> ORGANISM: Artificial
<220> FEATURE:
<223> OTHER INFORMATION: beta-hCG-derived peptide

<400> SEQUENCE: 52

Asn Pro Val Val Ser
1               5

<210> SEQ ID NO 53
<211> LENGTH: 6
<212> TYPE: PRT
<213> ORGANISM: Artificial
<220> FEATURE:
<223> OTHER INFORMATION: beta-hCG-derived peptide

<400> SEQUENCE: 53

Tyr Ala Val Ala Leu Ser
1               5

<210> SEQ ID NO 54
<211> LENGTH: 6
<212> TYPE: PRT
<213> ORGANISM: Artificial
<220> FEATURE:
<223> OTHER INFORMATION: beta-hCG-derived peptide

<400> SEQUENCE: 54

Leu Thr Cys Asp Asp Pro
1               5

<210> SEQ ID NO 55
<211> LENGTH: 4
<212> TYPE: PRT
<213> ORGANISM: Artificial
<220> FEATURE:
<223> OTHER INFORMATION: beta-hCG-derived peptide
```

-continued

```
<400> SEQUENCE: 55

Glu Met Phe Gln
1

<210> SEQ ID NO 56
<211> LENGTH: 4
<212> TYPE: PRT
<213> ORGANISM: Artificial
<220> FEATURE:
<223> OTHER INFORMATION: beta-hCG-derived peptide

<400> SEQUENCE: 56

Pro Val Val Ser
1

<210> SEQ ID NO 57
<211> LENGTH: 4
<212> TYPE: PRT
<213> ORGANISM: Artificial
<220> FEATURE:
<223> OTHER INFORMATION: beta-hCG-derived peptide

<400> SEQUENCE: 57

Val Ser Tyr Ala
1

<210> SEQ ID NO 58
<211> LENGTH: 4
<212> TYPE: PRT
<213> ORGANISM: Artificial
<220> FEATURE:
<223> OTHER INFORMATION: beta-hCG-derived peptide

<400> SEQUENCE: 58

Gly Val Leu Pro
1

<210> SEQ ID NO 59
<211> LENGTH: 4
<212> TYPE: PRT
<213> ORGANISM: Artificial
<220> FEATURE:
<223> OTHER INFORMATION: beta-hCG-derived peptide

<400> SEQUENCE: 59

Phe Gln Gly Leu
1

<210> SEQ ID NO 60
<211> LENGTH: 4
<212> TYPE: PRT
<213> ORGANISM: Artificial
<220> FEATURE:
<223> OTHER INFORMATION: beta-hCG-derived peptide

<400> SEQUENCE: 60

Ala Val Ala Leu
1

<210> SEQ ID NO 61
<211> LENGTH: 4
<212> TYPE: PRT
<213> ORGANISM: Artificial
<220> FEATURE:
<223> OTHER INFORMATION: Bruton's tyrosine kinase-derived peptide
```

<400> SEQUENCE: 61

Leu Ser Asn Ile
1

<210> SEQ ID NO 62
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 62

Tyr Val Phe Ser
1

<210> SEQ ID NO 63
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 63

Leu Tyr Gly Val
1

<210> SEQ ID NO 64
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 64

Tyr Val Val Cys
1

<210> SEQ ID NO 65
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 65

Phe Ile Val Arg
1

<210> SEQ ID NO 66
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 66

Asn Ile Leu Asp
1

<210> SEQ ID NO 67
<211> LENGTH: 4
<212> TYPE: PRT
<213> ORGANISM: Artificial
<220> FEATURE:
<223> OTHER INFORMATION: Bruton's tyrosine kinase-derived peptide

```
<400> SEQUENCE: 67

Thr Ile Met Tyr
1

<210> SEQ ID NO 68
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 68

Leu Glu Ser Ile
1

<210> SEQ ID NO 69
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 69

Phe Leu Leu Thr
1

<210> SEQ ID NO 70
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 70

Val Phe Ser Pro
1

<210> SEQ ID NO 71
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 71

Phe Ile Leu Glu
1

<210> SEQ ID NO 72
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 72

Thr Phe Leu Lys
1

<210> SEQ ID NO 73
<211> LENGTH: 4
<212> TYPE: PRT
<213> ORGANISM: Artificial
<220> FEATURE:
<223> OTHER INFORMATION: Bruton's tyrosine kinase-derived peptide
```

```
<400> SEQUENCE: 73

Phe Trp Ile Asp
1

<210> SEQ ID NO 74
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 74

Met Trp Glu Ile
1

<210> SEQ ID NO 75
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 75

Gln Leu Leu Glu
1

<210> SEQ ID NO 76
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 76

Pro Cys Phe Trp
1

<210> SEQ ID NO 77
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 77

Val His Lys Leu
1

<210> SEQ ID NO 78
<211> LENGTH: 4
<212> TYPE: PRT
<213> ORGANISM: Artificial
<220> FEATURE:
<223> OTHER INFORMATION: Bruton's tyrosine kinase-derived peptide

<400> SEQUENCE: 78

Tyr Val Phe Ser
1

<210> SEQ ID NO 79
<211> LENGTH: 4
<212> TYPE: PRT
<213> ORGANISM: Artificial
<220> FEATURE:
<223> OTHER INFORMATION: Bruton's tyrosine kinase-derived peptide
```

```
<400> SEQUENCE: 79

Ile Tyr Ser Leu
1

<210> SEQ ID NO 80
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 80

Phe Lys Gly Ala
1

<210> SEQ ID NO 81
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 81

Phe Phe Gly Leu
1

<210> SEQ ID NO 82
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 82

Gly Ile Ala Gln
1

<210> SEQ ID NO 83
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 83

Leu Gly Cys Leu
1

<210> SEQ ID NO 84
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 84

Tyr Trp Ile Tyr
1

<210> SEQ ID NO 85
<211> LENGTH: 4
<212> TYPE: PRT
<213> ORGANISM: Artificial
<220> FEATURE:
<223> OTHER INFORMATION: matrix metalloproteinase-2-derived peptide
```

```
<400> SEQUENCE: 85

Ala Trp Asn Ala
1

<210> SEQ ID NO 86
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 86

Ala Arg Gly Ala
1

<210> SEQ ID NO 87
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 87

Pro Phe Arg Phe
1

<210> SEQ ID NO 88
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 88

Ala Pro Ser Pro
1

<210> SEQ ID NO 89
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 89

Cys Leu Leu Ser
1

<210> SEQ ID NO 90
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 90

Gly Leu Pro Gln
1

<210> SEQ ID NO 91
<211> LENGTH: 4
<212> TYPE: PRT
<213> ORGANISM: Artificial
<220> FEATURE:
<223> OTHER INFORMATION: matrix metalloproteinase-2-derived peptide
```

```
<400> SEQUENCE: 91

Thr Phe Trp Pro
1

<210> SEQ ID NO 92
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 92

Ala Tyr Tyr Leu
1

<210> SEQ ID NO 93
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 93

Phe Trp Pro Glu
1

<210> SEQ ID NO 94
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 94

Cys Leu Leu Gly
1

<210> SEQ ID NO 95
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 95

Phe Leu Trp Cys
1

<210> SEQ ID NO 96
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 96

Arg Ile Ile Gly
1

<210> SEQ ID NO 97
<211> LENGTH: 4
<212> TYPE: PRT
<213> ORGANISM: Artificial
<220> FEATURE:
<223> OTHER INFORMATION: matrix metalloproteinase-2-derived peptide
```

```
<400> SEQUENCE: 97

Trp Ser Asp Val
1

<210> SEQ ID NO 98
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 98

Pro Ile Ile Lys
1

<210> SEQ ID NO 99
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 99

Gly Leu Pro Pro
1

<210> SEQ ID NO 100
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 100

Arg Ala Leu Cys
1

<210> SEQ ID NO 101
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 101

Leu Asn Thr Phe
1

<210> SEQ ID NO 102
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 102

Leu Ser His Ala
1

<210> SEQ ID NO 103
<211> LENGTH: 4
<212> TYPE: PRT
<213> ORGANISM: Artificial
<220> FEATURE:
<223> OTHER INFORMATION: matrix metalloproteinase-2-derived peptide
```

```
<400> SEQUENCE: 103

Ala Thr Phe Trp
1

<210> SEQ ID NO 104
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 104

Pro Ser Pro Ile
1

<210> SEQ ID NO 105
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 105

Ala His Glu Phe
1

<210> SEQ ID NO 106
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 106

Trp Arg Thr Val
1

<210> SEQ ID NO 107
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 107

Phe Val Leu Lys
1

<210> SEQ ID NO 108
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 108

Val Gln Tyr Leu
1

<210> SEQ ID NO 109
<211> LENGTH: 4
<212> TYPE: PRT
<213> ORGANISM: Artificial
<220> FEATURE:
<223> OTHER INFORMATION: matrix metalloproteinase-2-derived peptide
```

```
<400> SEQUENCE: 109

Lys Phe Phe Gly
1

<210> SEQ ID NO 110
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 110

Phe Pro Phe Arg
1

<210> SEQ ID NO 111
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 111

Ile Tyr Ser Ala
1

<210> SEQ ID NO 112
<211> LENGTH: 4
<212> TYPE: PRT
<213> ORGANISM: Artificial
<220> FEATURE:
<223> OTHER INFORMATION: matrix metalloproteinase-2-derived peptide

<400> SEQUENCE: 112

Phe Asp Gly Ile
1

<210> SEQ ID NO 113
<211> LENGTH: 17
<212> TYPE: PRT
<213> ORGANISM: Artificial
<220> FEATURE:
<223> OTHER INFORMATION: PEPTIDE

<400> SEQUENCE: 113

Met Thr Arg Val Leu Gln Gly Val Leu Pro Ala Leu Pro Gln Val Val
1               5                   10                  15

Cys

<210> SEQ ID NO 114
<211> LENGTH: 13
<212> TYPE: PRT
<213> ORGANISM: Artificial
<220> FEATURE:
<223> OTHER INFORMATION: PEPTIDE

<400> SEQUENCE: 114

Leu Pro Gly Cys Pro Arg Gly Val Asn Pro Val Val Ser
1               5                   10

<210> SEQ ID NO 115
<211> LENGTH: 9
<212> TYPE: PRT
<213> ORGANISM: Artificial
<220> FEATURE:
<223> OTHER INFORMATION: PEPTIDE
```

```
<400> SEQUENCE: 115

Asp Ile Asn Gly Phe Leu Pro Ala Leu
1               5

<210> SEQ ID NO 116
<211> LENGTH: 8
<212> TYPE: PRT
<213> ORGANISM: Artificial
<220> FEATURE:
<223> OTHER INFORMATION: PEPTIDE

<400> SEQUENCE: 116

Gln Pro Leu Ala Pro Leu Val Gly
1               5

<210> SEQ ID NO 117
<211> LENGTH: 4
<212> TYPE: PRT
<213> ORGANISM: Artificial
<220> FEATURE:
<223> OTHER INFORMATION: tetramer peptide

<400> SEQUENCE: 117

Leu Gln Gly Val
1

<210> SEQ ID NO 118
<211> LENGTH: 4
<212> TYPE: PRT
<213> ORGANISM: Artificial
<220> FEATURE:
<223> OTHER INFORMATION: tetramer peptide

<400> SEQUENCE: 118

Gln Val Val Cys
1

<210> SEQ ID NO 119
<211> LENGTH: 4
<212> TYPE: PRT
<213> ORGANISM: Artificial
<220> FEATURE:
<223> OTHER INFORMATION: tetramer peptide

<400> SEQUENCE: 119

Met Thr Arg Val
1

<210> SEQ ID NO 120
<211> LENGTH: 4
<212> TYPE: PRT
<213> ORGANISM: Artificial
<220> FEATURE:
<223> OTHER INFORMATION: tetramer peptide

<400> SEQUENCE: 120

Ala Gln Gly Val
1

<210> SEQ ID NO 121
<211> LENGTH: 4
<212> TYPE: PRT
<213> ORGANISM: Artificial
<220> FEATURE:
<223> OTHER INFORMATION: tetramer peptide
```

```
<400> SEQUENCE: 121

Leu Ala Gly Val
1

<210> SEQ ID NO 122
<211> LENGTH: 4
<212> TYPE: PRT
<213> ORGANISM: Artificial
<220> FEATURE:
<223> OTHER INFORMATION: tetramer peptide

<400> SEQUENCE: 122

Leu Gln Ala Val
1

<210> SEQ ID NO 123
<211> LENGTH: 4
<212> TYPE: PRT
<213> ORGANISM: Artificial
<220> FEATURE:
<223> OTHER INFORMATION: tetramer peptide

<400> SEQUENCE: 123

Pro Gly Cys Pro
1

<210> SEQ ID NO 124
<211> LENGTH: 4
<212> TYPE: PRT
<213> ORGANISM: Artificial
<220> FEATURE:
<223> OTHER INFORMATION: tetramer peptide

<400> SEQUENCE: 124

Val Gly Gln Leu
1

<210> SEQ ID NO 125
<211> LENGTH: 4
<212> TYPE: PRT
<213> ORGANISM: Artificial
<220> FEATURE:
<223> OTHER INFORMATION: tetramer peptide

<400> SEQUENCE: 125

Arg Val Leu Gln
1

<210> SEQ ID NO 126
<211> LENGTH: 4
<212> TYPE: PRT
<213> ORGANISM: Artificial
<220> FEATURE:
<223> OTHER INFORMATION: tetramer peptide

<400> SEQUENCE: 126

Glu Met Phe Gln
1

<210> SEQ ID NO 127
<211> LENGTH: 4
<212> TYPE: PRT
<213> ORGANISM: Artificial
<220> FEATURE:
<223> OTHER INFORMATION: tetramer peptide
```

```
<400> SEQUENCE: 127

Ala Val Ala Leu
1

<210> SEQ ID NO 128
<211> LENGTH: 4
<212> TYPE: PRT
<213> ORGANISM: Artificial
<220> FEATURE:
<223> OTHER INFORMATION: tetramer peptide

<400> SEQUENCE: 128

Cys Pro Val Gln
1

<210> SEQ ID NO 129
<211> LENGTH: 4
<212> TYPE: PRT
<213> ORGANISM: Artificial
<220> FEATURE:
<223> OTHER INFORMATION: tetramer peptide

<400> SEQUENCE: 129

Glu Val Val Arg
1

<210> SEQ ID NO 130
<211> LENGTH: 4
<212> TYPE: PRT
<213> ORGANISM: Artificial
<220> FEATURE:
<223> OTHER INFORMATION: tetramer peptide

<400> SEQUENCE: 130

Met Thr Glu Val
1

<210> SEQ ID NO 131
<211> LENGTH: 4
<212> TYPE: PRT
<213> ORGANISM: Artificial
<220> FEATURE:
<223> OTHER INFORMATION: tetramer peptide

<400> SEQUENCE: 131

Glu Ala Leu Glu
1

<210> SEQ ID NO 132
<211> LENGTH: 4
<212> TYPE: PRT
<213> ORGANISM: Artificial
<220> FEATURE:
<223> OTHER INFORMATION: tetramer peptide

<400> SEQUENCE: 132

Glu Pro Pro Glu
1

<210> SEQ ID NO 133
<211> LENGTH: 4
<212> TYPE: PRT
<213> ORGANISM: Artificial
<220> FEATURE:
<223> OTHER INFORMATION: tetramer peptide
```

```
<400> SEQUENCE: 133

Leu Gly Thr Leu
1

<210> SEQ ID NO 134
<211> LENGTH: 4
<212> TYPE: PRT
<213> ORGANISM: Artificial
<220> FEATURE:
<223> OTHER INFORMATION: tetramer peptide

<400> SEQUENCE: 134

Val Gly Gly Ile
1

<210> SEQ ID NO 135
<211> LENGTH: 4
<212> TYPE: PRT
<213> ORGANISM: Artificial
<220> FEATURE:
<223> OTHER INFORMATION: tetramer peptide

<400> SEQUENCE: 135

Arg Leu Pro Gly
1

<210> SEQ ID NO 136
<211> LENGTH: 4
<212> TYPE: PRT
<213> ORGANISM: Artificial
<220> FEATURE:
<223> OTHER INFORMATION: tetramer peptide

<400> SEQUENCE: 136

Leu Gln Gly Ala
1

<210> SEQ ID NO 137
<211> LENGTH: 4
<212> TYPE: PRT
<213> ORGANISM: Artificial
<220> FEATURE:
<223> OTHER INFORMATION: tetramer peptide

<400> SEQUENCE: 137

Leu Cys Phe Leu
1

<210> SEQ ID NO 138
<211> LENGTH: 5
<212> TYPE: PRT
<213> ORGANISM: Artificial
<220> FEATURE:
<223> OTHER INFORMATION: pentamer peptide

<400> SEQUENCE: 138

Val Glu Gly Asn Leu
1               5

<210> SEQ ID NO 139
<211> LENGTH: 5
<212> TYPE: PRT
<213> ORGANISM: Artificial
<220> FEATURE:
<223> OTHER INFORMATION: pentamer peptide
```

```
<400> SEQUENCE: 139

Leu Asn Glu Ala Leu
1               5

<210> SEQ ID NO 140
<211> LENGTH: 6
<212> TYPE: PRT
<213> ORGANISM: Artificial
<220> FEATURE:
<223> OTHER INFORMATION: hexamer peptide

<400> SEQUENCE: 140

Val Leu Pro Ala Leu Pro
1               5

<210> SEQ ID NO 141
<211> LENGTH: 7
<212> TYPE: PRT
<213> ORGANISM: Artificial
<220> FEATURE:
<223> OTHER INFORMATION: septamer peptide

<400> SEQUENCE: 141

Val Leu Pro Ala Pro Leu Gln
1               5

<210> SEQ ID NO 142
<211> LENGTH: 7
<212> TYPE: PRT
<213> ORGANISM: Artificial
<220> FEATURE:
<223> OTHER INFORMATION: septamer peptide

<400> SEQUENCE: 142

Cys Pro Arg Gly Val Asn Pro
1               5

<210> SEQ ID NO 143
<211> LENGTH: 7
<212> TYPE: PRT
<213> ORGANISM: Artificial
<220> FEATURE:
<223> OTHER INFORMATION: septamer peptide

<400> SEQUENCE: 143

Val Leu Pro Ala Leu Pro Gln
1               5

<210> SEQ ID NO 144
<211> LENGTH: 4
<212> TYPE: PRT
<213> ORGANISM: Artificial
<220> FEATURE:
<223> OTHER INFORMATION: tetramer peptide

<400> SEQUENCE: 144

Leu Pro Gly Cys
1
```